US010799456B2

(12) United States Patent
Ho et al.

(10) Patent No.: US 10,799,456 B2
(45) Date of Patent: Oct. 13, 2020

(54) MULTIPLE DRUG LIPID NANOPARTICLE COMPOSITION AND RELATED METHODS FOR EXTENDED DRUG LEVELS IN BLOOD AND LYMPH TISSUE

(71) Applicant: University of Washington, Seattle, WA (US)

(72) Inventors: Rodney J. Y. Ho, Seattle, WA (US); Jennifer Iwamoto, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/735,118

(22) PCT Filed: Jun. 15, 2016

(86) PCT No.: PCT/US2016/037651
§ 371 (c)(1),
(2) Date: Dec. 8, 2017

(87) PCT Pub. No.: WO2016/205384
PCT Pub. Date: Dec. 22, 2016

(65) Prior Publication Data
US 2019/0350853 A1 Nov. 21, 2019

Related U.S. Application Data

(60) Provisional application No. 62/175,565, filed on Jun. 15, 2015.

(51) Int. Cl.
*A61K 9/127* (2006.01)
*A61K 9/14* (2006.01)
(Continued)

(52) U.S. Cl.
CPC ............... *A61K 9/127* (2013.01); *A61K 9/14* (2013.01); *A61K 9/5123* (2013.01);
(Continued)

(58) Field of Classification Search
CPC .................................................. A61K 9/127
See application file for complete search history.

(56) References Cited

U.S. PATENT DOCUMENTS 4,957,735 A   9/1990  Huang
6,645,528 B1 * 11/2003  Straub ............... A61K 9/1611
                                                    424/489

(Continued)

FOREIGN PATENT DOCUMENTS

WO  1988/006443 A1   9/1988
WO  2006/130943 A1  12/2006

(Continued)

OTHER PUBLICATIONS

Aji Alex, M.R., et al., "Lopinavir Loaded Solid Lipid Nanoparticles (SLN) for Intestinal Lymphatic Targeting," European Journal of Pharmaceutical Sciences 42(1-2):11-18, Jan. 2011.

(Continued)

*Primary Examiner* — Benjamin J Packard
(74) *Attorney, Agent, or Firm* — Christensen O'Connor Johnson Kindness PLLC

(57) ABSTRACT

Provided are multi-drug lipid nanoparticles that stably incorporate multiple small molecule drugs with divergent hydrophobic and water solubility characteristics and related methods of making and using the same, The disclosed compositions and methods provide for enhanced stability of lipid nanoparticle drug formulations that can reliably provide drugs addressing different mechanistic targets with prolonged presence in the body for more efficacious treatment and avoidance of single drug resistance.

21 Claims, 19 Drawing Sheets

(51) Int. Cl.
| | |
|---|---|
| A61K 9/51 | (2006.01) |
| A61K 31/427 | (2006.01) |
| A61K 31/513 | (2006.01) |
| A61K 31/536 | (2006.01) |
| A61K 31/5365 | (2006.01) |
| A61K 31/675 | (2006.01) |
| A61K 31/7072 | (2006.01) |
| A61K 47/24 | (2006.01) |

(52) U.S. Cl.
CPC .......... *A61K 31/427* (2013.01); *A61K 31/513* (2013.01); *A61K 31/536* (2013.01); *A61K 31/5365* (2013.01); *A61K 31/675* (2013.01); *A61K 31/7072* (2013.01); *A61K 47/24* (2013.01)

(56) References Cited

U.S. PATENT DOCUMENTS

| | | |
|---|---|---|
| 8,846,096 B2 | 9/2014 | Destache |
| 2011/0200665 A1 | 8/2011 | Mei et al. |
| 2012/0087857 A1* | 4/2012 | Ho .................. A61K 49/1824 424/1.11 |
| 2013/0085146 A1 | 4/2013 | Ho et al. |
| 2013/0149381 A1* | 6/2013 | Lopez Campos .... A61K 9/5123 424/489 |
| 2014/0294932 A1 | 10/2014 | Kim et al. |
| 2014/0308363 A1 | 10/2014 | Zale |
| 2014/0348900 A1 | 11/2014 | Zhu |

FOREIGN PATENT DOCUMENTS

| | | |
|---|---|---|
| WO | 2014/015027 A1 | 1/2014 |
| WO | 2014/074952 A1 | 5/2014 |
| WO | 2015/066535 A1 | 5/2015 |

OTHER PUBLICATIONS

Alberts, B., et al., "Molecular Biology of the Cell," 5th ed., Garland Science, New York, 2002, 1732 pages.

Ambrose, Z., et al., "Suppression of Viremia and Evolution of Human Immunodeficiency Virus Type 1 Drug Resistance in a Macaque Model for Antiretroviral Therapy," Journal of Virology 81(22):12145-12155, Nov. 2007.

Antoniou, T., et al., "Tenofovir: A Nucleotide Analog for the Management of Human Immunodeficiency Virus Infection," Pharmacotherapy 23(1):29-43, Jan. 2003.

Böyum, A., "Isolation of Mononuclear Cells and Granulocytes From Human Blood. Isolation of Monuclear Cells by One Centrifugation, and of Granulocytes by Combining Centrifugation and Sedimentation at 1 g," Scandinavian Journal of Clinical and Laboratory Investigation 21(Suppl. 97):77-89, 1 page, 1968.

Bozic, I., et al., "Evolutionary Dynamics of Cancer in Response to Targeted Combination Therapy," eLife 2:e00747, Jun. 2013, 15 pages.

Buehler, D.C., et al., "Bioengineered Vaults: Self-Assembling Protein Shell-Lipophilic Core Nanoparticles for Drug Delivery," ACS Nano 8(8):7723-7732, Aug. 2014.

Bui, T., et al., "Novel Gd Nanoparticles Enhance Vascular Contrast for High-Resolution Magnetic Resonance Imaging," PLoS One 5(9):e13082, Sep. 2010, 7 pages.

Cavert, W., et al., "Kinetics of Response in Lymphoid Tissues to Antiretroviral Therapy of HIV-1 Infection," Science 276(5314):960-964, May 1997.

Cheng, T., et al., "Computation of Octanol-Water Partition Coefficients by Guiding an Additive Model With Knowledge," Journal of Chemical Information and Modeling 47(6):2140-2148, Nov.-Dec. 2007.

Choi, S.-U., et al., "pH-Dependent Interactions of Indinavir and Lipids in Nanoparticles and Their Ability to Entrap a Solute," Journal of Pharmaceutical Sciences 97(2):931-943, Feb. 2008.

Chun, T.W., et al., "Re-Emergence of HIV After Stopping Therapy," Nature 401(6756):874-875, Oct. 1999.

Cicconi, P., et al., "Insights Into Reasons for Discontinuation According to Year of Starting First Regimen of Highly Active Antiretroviral Therapy in a Cohort of Antiretroviral-Naive Patients," HIV Medicine 11(2):104-113, Feb. 2010.

Cohen, C., et al., "Comparison of Atazanavir With Lopinavir/Ritonavir in Patients With Prior Protease Inhibitor Failure: A Randomized Multinational Trial," Current Medical Research and Opinion 21(10):1683-1692, Oct. 2005.

Date, A.A., et al., Parasitic Diseases: Liposomes and Polymeric Nanoparticles Versus Lipid Nanoparticles. Advanced Drug Delivery Reviews 59(6):505-521, Jul. 2007.

DeVita, V.A., Jr., et al., "Combination Versus Single Agent Chemotherapy: A Review of the Basis for Selection of Drug Treatment of Cancer," Cancer 35(1):98-110, Jan. 1975.

Dittert, L.W., et al., "Phase Solubility Technique in Studying the Formation of Complex Salts of Triamterene," Journal of Pharmaceutical Sciences 53(11):1325-1328, Nov. 1964.

Duan, J., et al., "Evaluation of Atazanavir and Darunavir Interactions With Lipids for Developing pH-Responsive Anti-HIV Drug Combination Nanoparticles," Journal of Pharmaceutical Sciences 103(8):2520-2529, Aug. 2014.

Dumay, E., et al., "Technological Aspects and Potential Applications of (Ultra) High-Pressure Homogenisation," Trends in Food Science & Technology 31(1):13-26, May 2013.

Elorza, B., et al., "Comparison of Particle Size and Encapsulation Parameters of Three Liposomal Preparations," Journal of Microencapsulation 10(2):237-248, Apr.-Jun. 1993.

Eloy, J.O., et al., "Liposomes as Carriers of Hydrophilic Small Molecule Drugs: Strategies to Enhance Encapsulation and Delivery," Colloids and Surfaces B: Biointerfaces 123:345-363, Nov. 2014.

Endsley, A.N., and R.J. Ho, "Design and Characterization of Novel Peptide-Coated Lipid Nanoparticles for Targeting Anti-HIV Drug to CD4 Expressing Cells," AAPS Journal 14(2):225-235, Jun. 2012.

Endsley A.N., and R.J. Ho, "Enhanced Anti-HIV Efficacy of Indinavir After Inclusion in CD4-Targeted Lipid Nanoparticles," Journal of Acquired Immune Deficiency Syndromes 61(4):417-424, Dec. 2012.

Fletcher, C.V., et al., "Persistent HIV-1 Replication is Associated With Lower Antiretroviral Drug Concentrations in Lymphatic Tissues," Proceedings of the National Academy of Sciences of the USA (PNAS) 111(6):2307-2312, Feb. 2014.

Freeling, J.P., and R.J. Ho, "Anti-HIV Drug Particles May Overcome Lymphatic Drug Insufficiency and Associated HIV Persistence," Proceedings of the National Academy of Sciences of the USA (PNAS) 111(25):E2512-E2513, Jun. 2014.

Freeling, J.P., et al., "Anti-HIV Drug-Combination Nanoparticles Enhance Plasma Drug Exposure Duration as Well as Triple-Drug Combination Levels in Cells Within Lymph Nodes and Blood in Primates," AIDS Research and Human Hum Retroviruses 31(1):107-114, Jan. 2015.

Freeling, J.P., et al., "Long-Acting Three-Drug Combination Anti-HIV Nanoparticles Enhance Drug Exposure in Primate Plasma and Cells Within Lymph Nodes and Blood," AIDS 28(17):2625-2627, Nov. 2014.

Gallicano, K., "Antiretroviral-Drug Concentrations in Semen," Antimicrobial Agents and Chemotherapy 44(4):1117-1118, Apr. 2000.

Gaur, P.K., et al., "Enhanced Oral Bioavailability of Efavirenz by Solid Lipid Nanoparticles: In Vitro Drug Release and Pharmacokinetics Studies," BioMed Research International, vol. 2014, Article ID 363404, 2014, 9 pages.

Gopee, N.V., et al., "Migration of Intradermally Injected Quantum Dots to Sentinel Organs in Mice," Toxicological Sciences 98(1):249-257, Jul. 2007. (Author Manuscript provided, PMCID: PMC3471152, available in PMC Oct. 15, 2012, 18 pages.).

"Guidelines for the Use of Antiretroviral Agents in HIV-1-Infected Adults and Adolescents," HHS Panel on Antiretroviral Guidelines for Adults and Adolescents—A Working Group of the Office of AIDS Research Advisory Council (OARAC), Mar. 2012, 266 pages.

Gunaseelan, S., et al., "Surface Modifications of Nanocarriers for Effective Intracellular Delivery of Anti-HIV Drugs," Advanced Drug Delivery Reviews 62(4-5):518-531, Mar. 2010.

(56) References Cited

OTHER PUBLICATIONS

Günthard, H.F., et al., "Antiretroviral Treatment of Adult HIV Infection: 2014 Recommendations of the International Antiviral Society—USA Panel," 312(4):410-425, Jul. 2014.

Günthard, H.F., et al., "Residual Human Immunodeficiency Virus (HIV) Type 1 RNA and DNA in Lymph Nodes and HIV RNA in Genital Secretions and in Cerebrospinal Fluid After Suppression of Viremia for 2 Years," Journal of Infectious Diseases 183(9):1318-1327, May 2001.

Guo, S., et al., "Unmodified Drug Used as a Material to Construct Nanoparticles: Delivery of Cisplatin for Enhanced Anti-Cancer Therapy," Journal of Controlled Release 174:137-142, Jan. 2014.

Hall, H.I., et al., "Differences in Human Immunodeficiency Virus Care and Treatment Among Subpopulations in the United States," JAMA Internal Medicine 173(14):1337-1344, Jul. 2013.

Hammer, S.M., et al., "A Controlled Trial of Two Nucleoside Analogues Plus Indinavir in Persons With Human Immunodeficiency Virus Infection and CD4 Cell Counts of 200 Per Cubic Millimeter or Less. AIDS Clinical Trials Group 320 Study Team," New England Journal of Medicine 337(11):725-733, Sep. 1997.

Heath, T.J., et al., "Afferent Pathways of Lymph Flow Within the Popliteal Node in Sheep," Journal of Anatomy 149:65-75, Dec. 1986.

Ho, R.J.Y., "Advanced Drug Delivery," in R.J. Ho et al. (eds.), "Biotechnology and Biopharmaceuticals: Transforming Proteins and Genes Into Drugs," 2d ed., 2014, John Wiley & Sons, Inc., New Jersey, pp. 427-469.

Horiike, M., et al., "Lymph Nodes Harbor Viral Reservoirs That Cause Rebound of Plasma Viremia in SIV-Infected Macaques Upon Cessation of Combined Antiretroviral Therapy," Virology 423(2):107-118, Feb. 2011.

Hsu, A., et al., "Ritonavir: Clinical Pharmacokinetics and Interactions With Other Anti-HIV Agents," Clinical Pharmacokinetics 35(4):275-291, Oct. 1998.

Jacobson, K., and D. Papahadjopoulos, "Phase Transitions and Phase Separations in Phospholipid Membranes Induced by Changes in Temperature, pH, and Concentration of Bivalent Cations," Biochemistry 14(1):152-161, Jan. 1975.

Kashuba, A.D., et al., "Antiretroviral-Drug Concentrations in Semen: Implications for Sexual Transmission of Human Immunodeficiency Virus Type 1," Antimicrobial Agents and Chemotherapy 43(8)1817-1826, Aug. 1999.

Kaur, C.D., et al. "Lymphatic Targeting of Zidovudine Using Surface-Engineered Liposomes," Journal of Drug Targeting 16(10):798-805, Dec. 2008.

Kim, S.-H., et al., "Adherence to Antiretroviral Therapy in Adolescents Living With HIV: Systematic Review and Meta-Analysis," AIDS 28(13):1945-1956, Aug. 2014.

Kinman, L., et al., "Lipid-Drug Association Enhanced HIV-1 Protease Inhibitor Indinavir Localization in Lymphoid Tissues and Viral Load Reduction: A Proof of Concept Study in HIV-2287-Infected Macaques," Journal of Acquired Immune Deficiency Syndromes 34(4):387-397, Dec. 2003.

Kinman, L., et al., "Optimization of Lipid-Indinavir Complexes for Localization in Lymphoid Tissues of HIV-Infected Macaques," Journal of Acquired Immune Deficiency Syndromes 42(2):155-161, Jun. 2006.

Kline, C., et al., "Persistence of Viral Reservoirs in Multiple Tissues after Antiretroviral Therapy Suppression in a Macaque RT-SHIV Model," PLoS One 8(12):e84275, Dec. 2013, 15 pages.

Koehn, J., and R.J. Ho, "Novel Liquid Chromatography-Tandem Mass Spectrometry Method for Simultaneous Detection of Anti-HIV Drugs Lopinavir, Ritonavir and Tenofovir in Plasma," Antimicrobial Agents and Chemotherapy 58(5):2675-2680, May 2014.

Komarova, N.L., and D. Wodarz, "Drug Resistance in Cancer: Principles of Emergence and Prevention," Proceedings of the National Academy of Sciences of the USA (PNAS) 102(27):9714-9719, Jul. 2005.

International Preliminary Report on Patentability dated Dec. 19, 2017, issued in corresponding International Application No. PCT/US2016/037651, filed Jun. 15, 2016, 14 pages.

Kuo, Y.-C., and C.Y. Chung, "Solid Lipid Nanoparticles Comprising Internal Compritol 888 ATO, Tripalmitin and Cacao Butter for Encapsulating and Releasing Stavudine, Delavirdine and Saquinavir," Colloids and Surfaces B: Biointerfaces 88(2):682-690, Dec. 2011.

Lafeuillade, A., et al., "Residual Human Immunodeficiency Virus Type 1 RNA in Lymphoid Tissue of Patients With Sustained Plasma RNA of <200 Copies/mL," Journal of Infectious Diseases 177(1):235-238, Jan. 1998.

Lentz, B.R., "Use of Fluorescent Probes to Monitor Molecular Order and Motions Within Liposome Bilayers," Chemistry and Physics of Lipids 64(1-3):99-116, Sep. 1993.

Lentz, B.R., et al., "Fluorescence Depolarization Studies of Phase Transitions and Fluidity in Phospholipid Bilayers. 1. Single Component Phosphatidylcholine Liposomes," Biochemistry 15(20):4521-4528, Oct. 1976.

Lentz, B.R., et al., "Fluorescence Depolarization Studies of Phase Transitions and Fluidity in Phospholipid Bilayers. 2 Two-Component Phosphatidylcholine Liposomes," Biochemistry 15(20):4529-4537, Oct. 1976.

Lv, H., et al., "Toxicity of Cationic Lipids and Cationic Polymers in Gene Delivery," Journal of Controlled Release 114(1):100-109, Aug. 2006.

Mabrey, S., and J.M. Sturtevant, "Investigation of Phase Transitions of Lipids and Lipid Mixtures by Sensitivity Differential Scanning Calorimetry," Proceedings of the National Academy of Sciences of the USA (PNAS) 73(11):3862-3866, Nov. 1976.

Madruga, J.V., et al., "Efficacy and Safety of Darunavir-Ritonavir Compared With That of Lopinavir-Ritonavir at 48 Weeks in Treatment-Experienced, HIV-Infected Patients in Titan: A Randomised Controlled Phase III Trial," The Lancet 370(9581):49-58, Jul. 2007.

Martínez, E., et al., "Lymphoid Tissue Viral Burden and Duration of Viral Suppression in Plasma," AIDS 15(12):1477-1482, Aug. 2001.

Mills, A.M., et al., "Once-Daily Darunavir/Ritonavir vs. Lopinavir/Ritonavir in Treatment-Naive, HIV-1-Infected Patients: 96-Week Analysis," AIDS 23(13):1679-1688, Aug. 2009.

Molina, J.M., et al., "Once-Daily Atazanavir/Ritonavir Versus Twice-Daily Lopinavir/Ritonavir, Each in Combination With Tenofovir and Emtricitabine, for Management of Antiretroviral-Naive HIV-1-Infected Patients: 48 Week Efficacy and Safety Results of the CASTLE Study," The Lancet 372(9639):646-655, Aug. 2008.

Nii, T., and F. Ishii, "Encapsulation Efficiency of Water-Soluble Drug Insoluble Drugs in Liposomes Prepared by the Microencapsulation Vesicle Method," International Journal of Pharmaceutics 298(1):198-205, Jul. 2005.

Notermans, D.W., et al., "Decrease of HIV-1 RNA Levels in Lymphoid Tissue and Peripheral Blood During Treatment With Ritonavir, Lamivudine and Zidovudine. Ritonavir/3TC/ZDV Study Group," AIDS 12(2):167-173, Jan. 1998.

Nowacek, A.S., et al., "Nanoformulated Antiretroviral Drug Combinations Extend Drug Release and Antiretroviral Responses in HIV-1-Infected Macrophages: Implications for NeuroAIDS Therapeutics," Journal of Neuroimmune Pharacology 5(4):592-601, Dec. 2010.

Oussoren, C., et al., "Lymphatic Uptake and Biodistribution of Liposomes After Subcutaneous Injection. II. Influence of Liposomal Size, Lipid Composition and Lipid Dose," Biochim et Biophysica Acta 1328(2):261-272, Sep. 1997.

Palella, F.J., Jr., et al., "HIV Outpatient Study Investigators. 1998. Declining Morbidity and Mortality Among Patients With Advanced Human Immunodeficiency Virus Infection," New England Journal of Medicine 338(13):853-860, Mar. 1998.

Pantaleo, G., et al., "HIV Infection is Active and Progressive in Lymphoid Tissue During the Clinically Latent Stage of Disease," Nature 362(6418):355-358, Mar. 1993.

Paquin, P., "Technological Properties of High Pressure Homogenizers: The Effect of Fat Globules, Milk Proteins, and Polysaccharides," International Dairy Journal 9(3-6):329-335, Mar.-Jun. 1999.

Parboosing, R., et al. "Nanotechnology and the Treatment of HIV Infection," Viruses 4(4):488-520, Apr. 2012.

(56) References Cited

OTHER PUBLICATIONS

Paterson, D.L., et al., "Adherence to protease inhibitor therapy and outcomes in patients with HIV infection," Annals of Internal Medicine 133(1):21-30, Jul. 2000.

Pau, A.K., and J.M. George, "Antiretroviral Therapy: Current Drugs," Infectious Disease Clinics of North America 28(3):371-402, Sep. 2014.

Pérez-Elías, M.J., "Atazanavir: Simplicity and Convenience in Different Scenarios," Expert Opinion on Pharmacotherapy 8(5):689-700, Apr. 2007.

Piliero, P.J., "Pharmacokinetic Properties of Nucleoside/Nucleotide Reverse Transcriptase Inhibitors," Journal of Acquired Immune Deficiency Syndromes 37(Suppl. 1):S2-S12, Sep. 2004.

Pomerantz, R.J., "Residual HIV-1 Infection During Antiretroviral Therapy: The Challenge of Viral Persistence," AIDS 15(10):1201-1211, Jul. 2001.

Ramana, L.N., et al., "Stealth Anti-CD4 Conjugated Immunoliposomes With Dual Antiretroviral Drugs —Modern Trojan Horses to Combat HIV," European Journal of Pharmaceutics and Biopharmaceutics 89:300-311, Jan. 2015.

Ravi, P.R., et al., "A Hybrid Design to Optimize Preparation of Lopinavir Loaded Solid Lipid Nanoparticles and Comparative Pharmacokinetic Evaluation With Marketed Lopinavir/Ritonavir Coformulation," Journal of Pharmacology and Pharmacotherapeutics 66(7):912-926, Jul. 2014.

Robison, L.S., et al., "Short-Term Discontinuation of HAART Regimens More Common in Vulnerable Patient Populations," AIDS Research and Human Retroviruses 24(11):1347-1355, Nov. 2008.

Ross, E.L., et al., "The Clinical Role and Cost-Effectiveness of Long-Acting Antiretroviral Therapy," Clinical Infectious Diseases 60(7):1102-1110, Apr. 2015.

Schacker, T., et al., "Rapid Accumulation of Human Immunodeficiency Virus (HIV) in Lymphatic Tissue Reservoirs During Acute and Early HIV Infection: Implications for Timing of Antiretroviral Therapy," Journal of Infectious Diseases 181(1):354-357, Jan. 2000.

Senior, J.H., et al., "Interaction of Positively-Charged Liposomes With Blood: Implications for Their Application In Vivo," Biochim et Biophysica Acta (BBA)—Biomembranes 1070(1):173-179, Nov. 1991.

Shegokar, R., and K.K. Singh, et al., "Stavudine Entrapped Lipid Nanoparticles for Targeting Lymphatic HIV Reservoirs," Die Pharmazie 66(4):264-271, Apr. 2011.

Shibata, A., et al., "Polymeric Nanoparticles Containing Combination Antiretroviral Drugs for HIV Type 1 Treatment," AIDS Research and Human Retroviruses 29(5):746-754, May 2013.

Siliciano, J.D., et al., "Long-Term Follow-Up Studies Confirm the Stability of the Latent Reservoir for HIV-1 in Resting CD4+ T Cells," Nature Medicine 9(6):727-728, Jun. 2003.

Solas, C., et al., "Discrepancies Between Protease Inhibitor Concentrations and Viral Load in Reservoirs and Sanctuary Sites in Human Immunodeficiency Virus-Infected Patients," Antimicrobial Agents and Chemotherapy 47(1):238-243, Jan. 2003.

Storch, C.H., et al., "Comparison of the Inhibitory Activity of Anti-HIV Drugs on P-Glycoprotein," Biochemical Pharmacology 73(10):1573-1581, May 2007.

Straubinger, R.M., et al., "pH-Sensitive Liposomes Mediate Cytoplasmic Delivery of Encapsulated Macromolecules," FEBS Letters 179(1):148-154, Jan. 1985.

Szoka, F., Jr., and D. Papahadjopoulos, "Procedure for Preparation of Liposomes With Large Internal Aqueous Space and High Capture by Reverse-Phase Evaporation," Proceedings of the National Academy of Sciences of the USA (PNAS) 75(9):4194-4198, Sep. 1978.

Vittinghoff, E., et al., "Combination Antiretroviral Therapy and Recent Declines in AIDS Incidence and Mortality," Journal of Infectious Diseases 179(3):717-720, Mar. 1999.

Wang, R., et al., "Calculating Partition Coefficient by Atom-Additive Method," Perspectives in Drug Discovery and Design 19(1):47-66, Sep. 2000.

Wei, X., et al., "Cationic Nanocarriers Induce Cell Necrosis Through Impairment of $Na^+$/$K^+$-ATPase and Cause Subsequent Inflammatory Response," Cell Research 25(2):237-253, Feb. 2015.

Williams, J., et al., "Long-Acting Parenteral Nanoformulated Antiretroviral Therapy: Interest and Attitudes of HIV-Infected Patients," Nanomedicine (Lond) 8(11):1807-1813, Nov. 2013. (Author Manuscript provided, PMCID: PMC3987826, available in PMC Sep. 1, 2014, 14 pages.).

Wong, J.K., et al., "Reduction of HIV-1 in Blood and Lymph Nodes Following Potent Antiretroviral Therapy and the Virologic Correlates of Treatment Failure," Proceedings of the National Academy of Sciences of the USA (PNAS) 94(23):12574-12579, Nov. 1997.

World Health Organization, "Consolidated Guidelines on the Use of Antiretroviral Drugs for Treating and Preventing HIV Infection. Recommendations for a Public Health Approach," Jun. 2013, 272 pages.

Xu, X., et al., "Predicting Hydrophilic Drug Encapsulation Inside Unilamellar Liposomes," International Journal of Pharmaceutics 423(2):410-418, Feb. 2012.

Zidan, A.S., et al., "Formulation and Transport Properties of Tenofovir Loaded Liposomes Through Caco-2 Cell Model," Journal of Liposome Research 23(4)318-326, Dec. 2013.

Endsley, A.N., and R.J.Y. Ho, "Enhanced Anti-HIV Efficacy of Indinavir After Inclusion in CD4 Targeted Lipid Nanoparticles," Journal of Acquired Immune Deficiency Syndrome 61(4):417-424, Dec. 2012. (Author Manuscript provided, PMCID:PMC3551348, available in PMC Sep. 1, 2013, 17 pages.).

Freeling, J.P., and R.J.Y, Ho, "Anti-HIV Drug Particles May Overcome Lymphatic Drug Insufficiency and Associated HIV Persistance," Proceedings of the National Academy of Sciences of the USA (PNAS) 111(25):E2512-E2513, Jun. 2014.

Freeling, J.P., et al., "Anti-HIV Drug-Combination Nanoparticles Enhance Plasma Drug Exposure Duration as Well as Triple-Drug Combination Levels in Cells Within Lymph Nodes and Blood in Primates," AIDS Research and Human Retroviruses 31(1):107-114, Jan. 2015.

International Search Report and Written Opinion dated Sep. 2, 2016, issued in corresponding International Application No. PCT/US2016/37651, filed Jun. 15, 2016, 18 pages.

Lin, Y.-K., et al., "Combination of Calcipotriol and Methotrexate in Nanostructured Lipid Carriers for Topical Delivery," International Journal of Nanomedicine 5:117-128, Mar. 2010.

\* cited by examiner

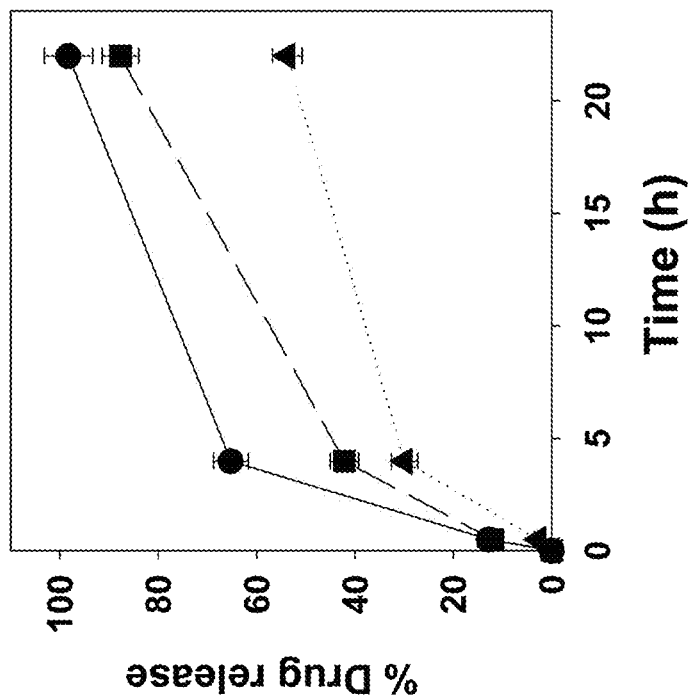
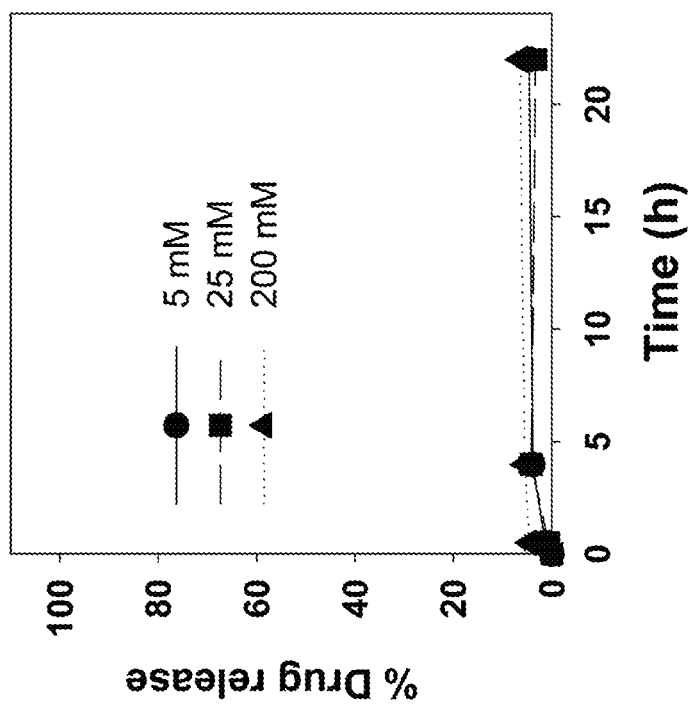
FIG. 3A
FIG. 3B

MULTIPLE DRUG LIPID NANOPARTICLE COMPOSITION AND RELATED METHODS FOR EXTENDED DRUG LEVELS IN BLOOD AND LYMPH TISSUE

CROSS-REFERENCE(S) TO RELATED APPLICATION(S)

This application claims the benefit of U.S. Provisional Application No. 62/175,565, filed Jun. 15, 2015, which is incorporated herein by reference in its entirety.

STATEMENT OF GOVERNMENT LICENSE RIGHTS

This invention was made with government support under Grant Nos. AI077390, AI120176, P51 OD010425, RR000166, RR025014, and TR000423, awarded by the National Institutes of Health. The government has certain rights in the invention.

BACKGROUND

Multi-drug combination therapy has become the standard-of-care for the treatment of diseases, such as caused by infection with Human Immunodeficiency Virus (HIV), and mounting evidence suggests its superiority over mono-drug therapy for the treatment of cancer. Specific to HIV infections, combined antiretroviral therapy (cART) consists of a daily regimen of multiple orally-administered antiretroviral drugs with different viral targets, and its benefits in terms of decreasing drug resistance and increasing therapeutic efficacy are well-established. However, due to challenges with noncompliance and associated viral relapse in patients on contemporary cART, there is urgent need for the development of long-acting anti-HIV drug technologies that can deliver multidrug therapy on a weekly or less frequent basis. Even with the implementation of single oral tablets or capsules containing multiple drugs as standard cART to ease pill burden, each drug in its free form naturally has a different pharmacokinetic profile, creating a challenge in maintaining effective plasma drug concentrations of each drug in concert to optimally suppress HIV without promoting resistance. Additionally, oral combination drugs penetrate poorly into lymph nodes and other lymphoid tissues, resulting in intracellular lymphatic drug concentrations that are low and inconsistent. This drug insufficiency has been linked to residual virus in patients on cART, even if they have low or no detectable virus in blood, which can lead to resurgence of viral levels.

Even with seemingly similar lipids or lipidic excipients used in drug-nanoparticle formulations, the methods of preparation and the resultant drug-excipients interactions can produce distinct pharmaceutical products with unique pharmacological and toxicological as well as distribution in the target or elimination tissues in the body. Standard procedures for incorporating drugs in enclosed membranes, for example in liposomes, are well-known. However, while liposomes and other enclosed membranes have been proposed as universal carriers for lipid soluble drugs (incorporated into the lipid shell) and water soluble drugs (encapsulated inside the spherical interior), incorporation and encapsulation of multiple drugs has been challenging.

Even if a drug is successfully associated with lipid particles, the resulting particles are often not sufficiently stable for product development. Liposome encapsulation of hydrophilic compounds, which include nucleoside analogue reverse transcriptase inhibitors (RTIs) such as tenofovir (TFV), lamivudine (3TC), and emtricitabine (FTC), which are key components of first-line cART, has proven particularly difficult. Encapsulation of small hydrophilic molecules in traditional liposomes with neutral charge is generally very low, often less than a few percentage points, due to the large amount of external aqueous space relative to the entrapped internal aqueous compartment of small unilamellar vesicles. Attempts to increase the capture of TFV require modification of the membrane content with a positively charged fatty acid. Not only are fatty acids readily removed from liposome membranes by proteins in serum, thus rendering the liposome carrier unstable and ineffective, but the positively charged cationic particles also interact with erythrocytes and other cells in vivo, leading to particle instability and cellular toxicity. Indeed, issues of toxicity associated with positively charged lipids have been a major barrier to clinical application of cationic non-viral vectors17.

Even for hydrophobic HIV drugs, which should more readily incorporate into lipid membranes, optimization studies with different lipid compositions yield incomplete and uneven degrees of two HIV drugs incorporated in liposomes. In addition, these liposomes, which even include polyethylene glycol modification to improve stability, readily release the drugs when incubated in only 10% serum, with approximately 80% of drug released within the first hour of incubation. The rapid destabilization of liposome-bound drug renders these particles ineffective for transit of drug from the injection site to target tissues. While solid polymeric particles can incorporate multiple hydrophobic drugs with as high as 81% efficiency, these particles are even larger than liposomes and lack an aqueous compartment, limiting their utility in accommodating multi-drug combinations. Additionally, these large polymeric drug carriers and smaller quantum dots often become trapped at the local site of injection and released slowly rather than transiting as a single drug-particle unit to the lymphoid tissues and cells.

A number of variation of and alternatives to standard liposome assembly procedures have been reported. For example, in reverse evaporation vesicle (REV), multilamellar vesicle, unilamellar vesicle, ethanol injection methods of liposome preparation are used. These preparations could provide high degree of incorporation of a single drug molecule, particularly for lipid soluble drugs. However, the ability to capture the water soluble hydrophilic drug in solution is variable and depends on the volume trapped and charge of drug molecule within liposomal enclosed membrane environment.

Intra-liposomal precipitation of doxorubicin-sulfate provides a method for high efficiency drug loading in the liposomes based on the ability of liposomal membrane to entrap charged molecules, such as $(NH_4)_2SO_4$, and membrane permeability of doxorubicin-HCl. However, this process, referred to as remote loading, is only suitable of limited number of drugs that are permeable and with counter ions that exhibit low solubility. Unfortunately, not all the drugs are suitable for remote loading into liposomes.

To increase encapsulation efficiency of liposomes and lipid-drug nanoparticles in pharmaceutical scale, others have used microencapsulation vehicle methods with either a single or double emulsion approaches with limited success. For example, a microemulsion approach produces varying degrees of reproducible drug levels for incorporation and requires removal of residual organic solvent from water at the final step, which could be difficult and could pose toxicity risk if removal process is incomplete. With single agent incorporation, the drug of interest must be added in an organic (oil) phase (for hydrophobic drug) or a water phase (for water soluble hydrophilic drug). This procedure is difficult to incorporate multiple drugs, particularly those that exhibit different physical characteristics—hydrophobic drug and hydrophilic drugs. A variation of the microemulsion approach is the double emulsion method, whereby a drug and a precipitant such as KCl are placed in two separate water in oil (o/w/o) emulsions with lipidic excipient and a surfactant. Upon mixing of the two o/w/o emulsions, the drug-KCl particles are formed as nano-drug precipitates. These nano-precipitates with a monolayer of lipidic coats are subjected to a second step of coating in organic or w/o emulsion of lipids such as cholesterol and DOTAP. This produces very low efficiency of nanoparticle drug incorporation. For example, for tenofovir (also referred to as PMPA), the final % drug association is less than 3%. Moreover, this approach is designed for a signal drug nanoparticle formation. While the drug loading, based on lipid to drug ratio may be high, the percent of drug wastage, based on the fraction of drug associated from start-to-finish is low.

To improve incorporation of water-soluble drugs that carry a charge, positively charged lipids, such as 1,2-di-palmitoyl-3-trimethylammonium-propane (DPTAP), have been included in the lipid membrane for electrostatic interaction. Unfortunately, positive charge can pose toxicity risk in animals and resulting particle sizes (larger than 100 nm diameter) are more susceptible to rapid clearance and elimination from the body. Similarly, incorporation of a fatty acid, stearylamine (SA), that carries a positive charge in the phosphatidylcholine lipid can increase the association of hydrophilic drugs such as TFV to 70% with large particles up to ~2000 nm in diameter. However, the positively charged particles have positive zeta potentials of 53-93 mV and exhibit mitochondrial toxicity by the same order. Therefore, compositions incorporating charged lipids to facilitate the incorporation of hydrophilic drugs are unlikely to be suitable for clinical development.

Despite the advances in the art, there remains a need for methods to efficiently and inexpensively incorporate multiple, structurally distinct drugs into a single drug delivery vehicle that provides for stable delivery to the intended tissues and targets within the body. In the context of HIV treatment, there remains a need for a drug delivery vehicle that is capable of sustaining drug concentrations in plasma and delivering drug to sites of viral persistence in lymphatic tissue. The present disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a multi-drug lipid nanoparticle. The multi-drug lipid nanoparticle comprises:
 a first small molecule agent with a log P at 25° C. greater than 1;
 a second small molecule agent with a log P at 25° C. less than 0;
 a first amphiphilic excipient, wherein the first amphiphilic excipient is a lipid comprising a hydrophilic domain with a molecular weight less than 300 grams/mol; and
 a second amphiphilic excipient comprising a hydrophilic domain with a molecular weight greater than 500 grams/mol.

In another aspect, the disclosure provides a method of preparing a multi-drug lipid nanoparticle. The method of this aspect comprises:
 dissolving in an organic solvent a first small molecule agent with a log P at 25° C. greater than 1, a first amphiphilic excipient wherein the first amphiphilic excipient is a lipid comprising a hydrophilic domain with a molecular weight less than 300 grams/mol, and second amphiphilic excipient comprising a hydrophilic domain with a molecular weight greater than 500 grams/mol, to provide an organic solvent solution, wherein the organic solvent comprises a subcomponent that is miscible with water;
 dissolving in an aqueous solvent a second small molecule agent with a log P at 25° C. less than 0 to provide an aqueous solvent solution;
 mixing the organic solvent solution and the aqueous solvent solution to provide a mixed solvent solution;
 removing the mixed solvents from the mixed solvent solution to provide a dehydrated product comprising the first small molecule agent, the first amphiphilic excipient, the second amphiphilic excipient, and the second small molecule agent; and
 rehydrating the dehydrated product in an aqueous solution to provide a solution with multi-drug lipid nanoparticles.

In another aspect, the disclosure provides a method of preparing a multi-drug lipid nanoparticle. The method of this aspect comprises:
 dissolving in a miscible solvent comprising an organic component and an aqueous component at a ratio of between about 20:1 and about 40:1 (v/v):
  a first small molecule agent with a log P at 25° C. greater than 1,
  a second small molecule agent with a log P at 25° C. less than 0,
  a first amphiphilic excipient wherein the first amphiphilic excipient is a lipid comprising a hydrophilic domain with a molecular weight less than 300 grams/mol, and
  a second amphiphilic excipient comprising a hydrophilic domain with a molecular weight greater than 500 grams/mol,
 removing the miscible solvent to provide a dehydrated product comprising the first small molecule agent, the second small molecule agent, the first amphiphilic excipient, and the second amphiphilic excipient;
 heating the dehydrated product to a first temperature that is at least 3° C. above a gel-to-liquid phase transition temperature of the amphiphilic excipients; and
 rehydrating the dehydrated product in an aqueous solution to provide a solution with multi-drug lipid nanoparticles.

The disclosure also encompasses any multi-drug lipid nanoparticles produced by the methods disclosed herein.

In another aspect, the disclosure provides pharmaceutical formulations comprising the multi-drug lipid nanoparticles disclosed herein.

In another aspect, the disclosure provides a method of treating subject infected with HIV, comprising administering an effective amount of the multi-drug lipid nanoparticles or formulations disclosed herein.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A is a schematic representation of an embodiment of the method referred to herein as the "mixed dual solvent" method. FIG. 1B is a schematic representation of an embodiment of the method referred to herein as the "single, miscible solvent" method.

FIGS. 3A and 3B graphically illustrate the concentration- and time-dependent atazanavir and darunavir release from lipid-drug nanoparticles. The release of atazanavir (FIG. 3A) and darunavir (FIG. 3B) from lipid-drug nanoparticles at 5 mM (●), 25 mM (■), and 200 mM (▲) were monitored at 25° C. Data are expressed as mean±SD % drug release of triplicate samples.

DETAILED DESCRIPTION

Figure 1A:
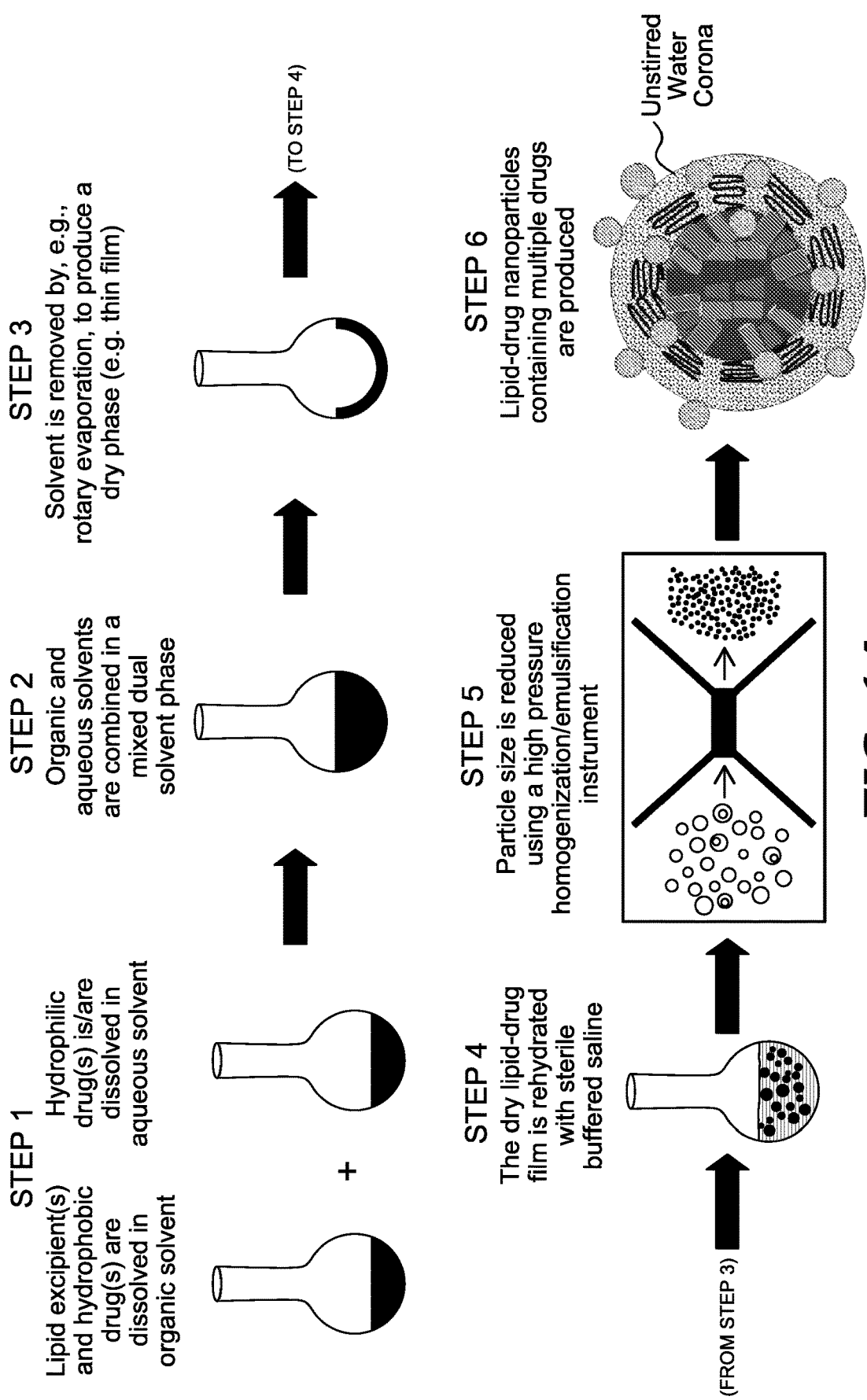
FIGS. 1A and 1B are schematic illustrations of exemplary methods for production of a multi-drug combination nanoparticles stabilized with lipid excipients.

This disclosure provides a new, elegant, and clinically useful method for the production of multi-drug, lipid-stabilized nanoparticles. This method results in novel lipid nanoparticles that incorporate drug compounds with different structural characteristics into a single delivery vehicle that results in not only sustained but also enhanced plasma and intracellular drug concentrations in vivo for all associated drugs. Use of the disclosed methods and resulting multi-drug lipid nanoparticle compositions provides the potential to overcome drug insufficiency by providing extended-release pharmacokinetic profiles for multiple drugs simultaneously at individual target sites. For anti-viral applications, the disclosed methods and compositions can overcome residual infections in tissues and avoid the potential for development of resistance to single drug regimens.

While our studies so far have focused on anti-HIV drug combinations, the versatile methods and compositions disclosed herein can be readily applied for the production of multi-drug therapeutics to treat cancer and other disease.

As described in more detail in the Examples below, the inventors developed new methodologies to produce novel lipid nanoparticles vehicles that can incorporate high levels of small molecule drug agents with widely variant structural characteristics, namely different agents that are hydrophilic and hydrophobic. The disclosed methods can be applied to a wide variety of small molecule drugs. The resulting multi-drug lipid nanoparticles, thus, conveniently serve as a singular vehicle that can produce surprisingly high and extended levels of all incorporated drugs in the plasma and tissues of a subject. Furthermore, the disclosed multi-drug lipid nanoparticles have the beneficial characteristics of avoiding toxicity issues associated with positively charged lipidic excipients (as described above) and exhibit remarkably stable storage characteristics. Furthermore, the methodology to assemble the multi-drug lipid nanoparticles is reproducible, efficient, readily scalable, and avoids the need for costly removal of unincorporated drug compositions, which is typically required for formulation safety. In the context of anti-HIV formulations, the methods provide for novel compositions that permit combinations of relevant combined formulations including high levels of hydrophilic agents that are critical for anti-HIV cART regimens. Sustained plasma and lymphoid tissue drug levels provided by the disclosed multi-drug lipid nanoparticles allows for decreased dosage frequencies, e.g., on the scale of weeks, to overcome issues of non-compliance seen with current daily oral medications.

Integral to the disclosed approach is the inventors' successful design and implementation of a unique solvent approach that permits the simultaneous combination and mixture of hydrophilic and hydrophobic components during lipid nanoparticle assembly. Many organic solvents useful for formation of lipidic nanoparticles are not miscible with water, which heretofore has presented the above described challenges in incorporating hydrophilic drug agents into lipid nanoparticles. However, the inventors found that combining such water immiscible organic solvents with water miscible organic solvents, such as alcohols, allows for the additional incorporation of limited amounts of aqueous solutions that include hydrophilic drug agents while maintaining a substantially single phase. The capacity to incorporate the aqueous solution and its components is provided by, and ultimately limited by, the capacity of the water miscible organic solvent to be water saturated. The resulting single phase solution allows for the complete mixture all components for the multi-drug lipid nanoparticles, both hydrophilic and hydrophobic. Dehydration removes the solvents and forces close association of all of the diverse components. This process reduces physical expulsion between the drugs, whether hydrophobic or hydrophilic, from lipidic excipients. The close contact also overcomes any need to add positive charge lipid excipients to increase drug association to particles, and reduce the positive charge related toxicity risk. Subsequent rehydration of the homogenized mixture of components in aqueous buffer results in nanosized lipid particles that incorporate higher total drug-to-lipid ratio than traditional liposomes, including both hydrophobic and hydrophilic drug agents, while being devoid of harmful residual detergents or solvents. The larger particles can be subjected to size reduction by sonication, extrusion trough filters or mechanical processes such as emulsifier or microfluidizer to result in a final uniform size, for example, from 20 nm-100 nm, to optimize for stability and avoid clearance in vivo.

One exemplary approach referred to herein as the "mixed dual solvent" method, as described in more detail below in Examples 1-4. See also FIG. 1A, which schematically illustrates an exemplary methodology. In this approach, the excipients (lipid or otherwise) and hydrophobic drug agents are dissolved in an organic solvent with a water miscible component and water immiscible component. Separately, the hydrophilic drug agent(s) is/are mixed in an aqueous solvent. Because the organic solution has the capacity for water saturation due to the water miscible organic component, the organic solution and aqueous solution are mixed together to form a mixed dual solvent phase. While low levels of initial emulsion might occur, the mixed dual solvent eventually forms a single phase with complete mixture of the multi-drug lipid nanoparticles. The actual multi-drug lipid nanoparticles are formed after the mixed solvent is removed by drying and the dry phase is rehydrated.

Figure 1B:
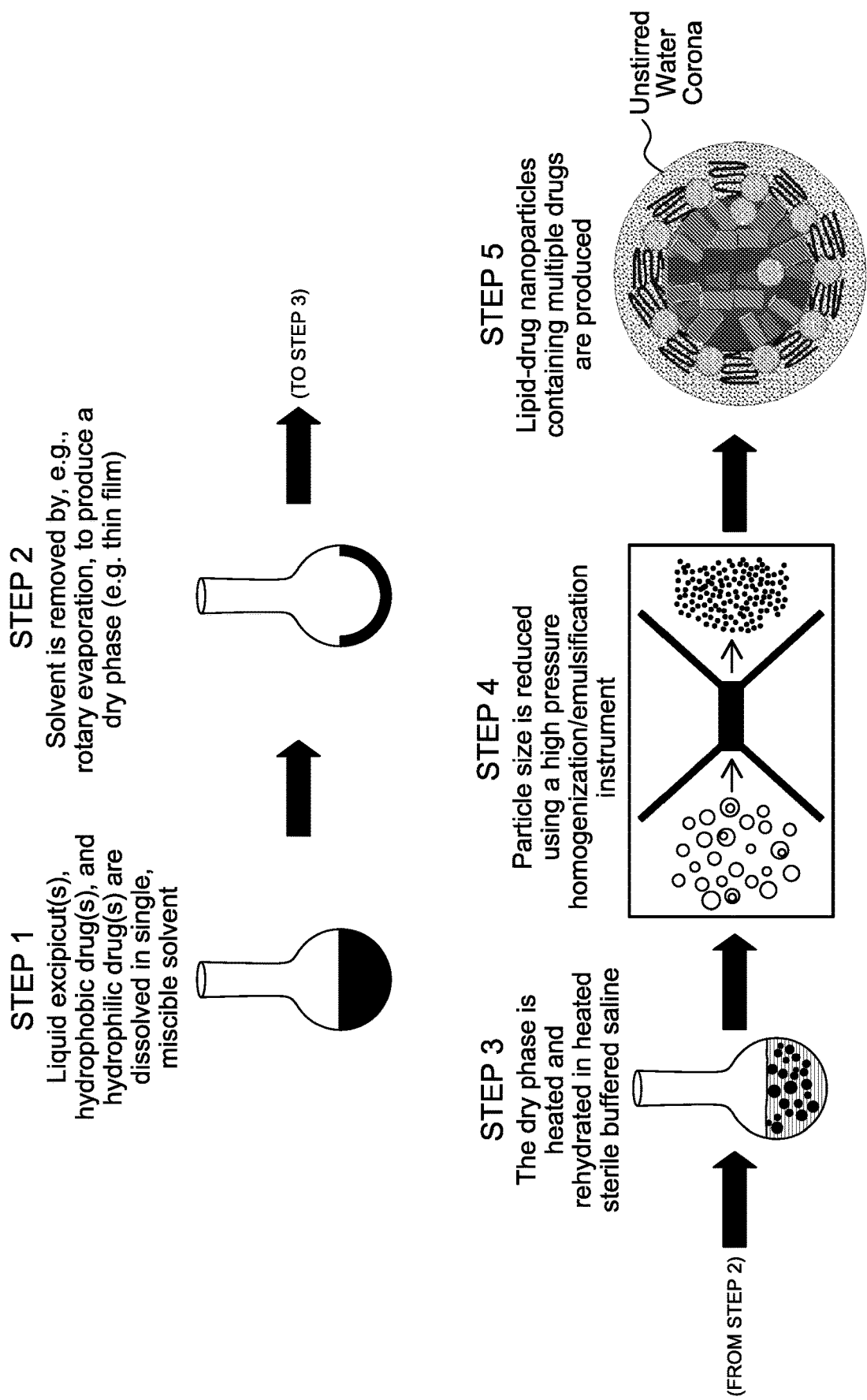

An alternative exemplary approach referred to herein as the "single, miscible solvent" method, is described in Example 5. See also FIG. 1B, which schematically illustrates an exemplary methodology. In this alternative, a single, miscible solvent is provided, which contains a water immiscible organic component, a water miscible organic component, and an minority aqueous component. As above, the ability to remain miscible (i.e., have the water be fully mixed without phase separation) is limited by the amount of water in the solution and the capacity of the water miscible organic component to become saturated with water. Once created, all of the components for the multi-drug lipid nanoparticles can be fully and thoroughly mixed in the same solution. The solvent is completely removed to provide a dry product that is homogenous and completely mixed. The dry product is rehydrated in aqueous buffer to form the lipid nanoparticles loaded with high levels of both hydrophilic and hydrophobic drug agents.

Overall, this novel approach requires fewer steps, is scalable, results in a high yield of nanoparticles with high drug association rates of multiple drugs even one exhibiting extreme differences of hydrophobic or hydrophilic characteristics. In addition, the final product is aqueous buffer and devoid of harmful solvents or positively charged excipients, which is amenable to most pharmaceutical applications. Finally, removal of un-associated fraction of water soluble drug is not necessary. Ultimately, the disclosed process significantly reduces the risk of contaminations due to multiple filtration or solvent removal, and further reduces costly wastage of removing un-associated drugs.

In view of the foregoing, in one aspect the disclosure provides a multi-drug lipid nanoparticle. The multi-drug lipid nanoparticle comprises a first small molecule agent with a log P at 25° C. greater than 1; a second small molecule agent with a log P at 25° C. less than 0; a first amphiphilic excipient, wherein the first amphiphilic excipient is a lipid comprising a hydrophilic domain with a molecular weight less than 300 grams/mol; and a second amphiphilic excipient comprising a hydrophilic domain with a molecular weight greater than 500 grams/mol.

As described herein, the disclosed multi-drug lipid nanoparticle can advantageously incorporate both hydrophilic and hydrophobic therapeutic agents to provide an effective vehicle for the specific combination. Hydrophobic/lipophilic, or substantially water-insoluble, pharmacologically active agents can be any bioactive agent having limited solubility in aqueous or hydrophilic environments. For example, the solubility in water of these agents at 20-25° C. can be less than about 5, 2, 1, 0.5, 0.2, 0.1, 0.05, 0.02, or 0.01 mg/mL. Hydrophilic, or substantially water-soluble, pharmacologically active agents can be any bioactive agent having high solubility in aqueous or hydrophilic environments. For example, the solubility in water of these agents at 20-25° C. can be more than about 5, 10, 20, 30, 40, 50, 75, 100, or more mg/mL.

The character of hydrophilic and hydrophobic therapeutic agents appropriate as candidate therapeutic agents that be incorporated into the lipid nanoparticle formulations as of the disclosure include therapeutic agents defined by their octanol/water partition coefficient X log P (Wang et al., Chem. Inf. Comput. Sci., 1997, 37, 615-621, incorporated herein by reference in its entirety). In the practice of the invention, therapeutic small molecule agents with log P greater than 1.0 are excellent candidates for incorporation into the nanoparticles of the invention as a hydrophobic (or lipophilic) agent. Examples of such anti-HIV agents are listed below in Table 18. Thus, as used herein, the terms "hydrophobic," "lipophilic," and "substantially water-insoluble" refer to therapeutic small molecule agents having an octanol/water partition coefficient log P greater than 1.0. In some embodiments, the log P for useful hydrophobic small molecule agents is greater than about 1.5, 2, 2.5, 3, 3.5, 4, 4.5, 5, 5.5, and 6. In the practice of the invention, therapeutic small molecule agents with a negative log P are excellent candidates for incorporation into the nanoparticles of the invention as a hydrophobic (or lipophilic) agent. Examples of such anti-HIV agents are listed below in Table 19. Thus, as used herein, the terms "hydrophilic" and "substantially water-soluble" refer to therapeutic small molecule agents having an octanol/water partition coefficient log P greater less than zero. In some embodiments, the log P for useful hydrophobic small molecule agents is less than about −0.25, −0.5, −0.75, −1.0, −1.25, −1.5, −1.75, −2.0, −2.5, −3.0, and −3.5.

In some embodiments, the log P is determined at about 25° C.

As used herein, the term "small molecule agent" refers to therapeutic molecules that with a molecular weight of about 1500 grams per mole or less. For example, the any small molecule agent can have a molecular weight of about 1500, 1250, 1000, 900, 800, 700, 600, 500, 400, 300, 200 g/mol or less.

Exemplary anti-HIV small molecule agents are listed in Tables 18-21, although it will be appreciated that the disclosed nanoparticles encompass any small molecule to address other diseases, conditions, or infections. In some embodiments, the first small molecule agent is selected from the group consisting of rilpivirine (RPV) or a prodrug thereof, efavirenz (EFV) or a prodrug thereof, dolutegravir (DTG) or a prodrug thereof, indinavir (IDV) or a prodrug thereof, atazanavir (ATV) or a prodrug thereof, ritonavir (RTV) or a prodrug thereof, lopinavir (LPV) or a prodrug thereof, and the like. In some embodiments, the second small molecule agent is selected from the group consisting of tenofovir (TNF) or a prodrug thereof, emtricitabine (FTC) or a prodrug thereof, lamivudine (3TC) or a prodrug thereof, raltegravir (RAL) or a prodrug thereof, zidovudine or a prodrug thereof, and the like. Persons of ordinary skill in the art can readily recognize prodrugs of relevant therapeutic small molecule agents. Additionally, persons of ordinary skill in the art will readily appreciate that small molecule agents are not limited by specific structures and can readily identify qualifying candidates for practice in the disclosed lipid nanoparticles and related methods.

In some embodiments, the multi-drug lipid nanoparticle has a mole ratio of total small molecule agents, including first and second small molecule agents, to excipients, including first and second amphiphilic excipients, of at least 1:10. In some embodiments, the mole ratio of total small molecule agents to total amphiphilic excipients is 1:10, 1:9. 1:8, 1:7, 1:6, 1:5, 1:4, 1:3, or greater. In some embodiments, the mole ratio of total small molecule agents to total amphiphilic lipid excipients is 1:10, 1:9. 1:8, 1:7, 1:6, 1:5, 1:4, 1:3, or greater. In this regard, as described in more detail herein, the multi-drug lipid nanoparticles produced by the dual mixed solvent method were characterized by a small molecule drug to lipid excipient ratio of about 1:8 to about 1:3. The multi-drug lipid nanoparticles produced by the single, miscible solvent method were characterized by a small molecule drug to lipid excipient ratio of about 1:3. Both of these ranges indicate a significantly higher drug incorporation over typical liposome formulations, which do not exceed a drug to lipid ratio of 1:10 and are often much lower.

The disclosed multi-drug lipid nanoparticles can encompass any relevant range of relative concentrations of first and second small molecule agents as determined by the intended use of the multi-drug lipid nanoparticles. To illustrate, the multi-drug lipid nanoparticles can have a mole ratio of first small molecule agent to second small molecule agent between about 1:20 to about 20:1, such as 1:9, 1:18, 1:17, 1:16, 1:15, 1:14, 1:13, 1:2, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, and the like.

The disclosed multi-drug lipid nanoparticles typically will have at least two different types of amphiphilic excipients. The first amphiphilic excipient is a lipid molecule that comprises a small hydrophilic domain. This type typically provides the majority of the structure of the lipid nanoparticle. The small hydrophilic domain assists the orienting the multiple lipid excipients into generally spherical structures when presented with an aqueous environment. The small hydrophilic domain typically has a molecular weight less than about 300 grams/mol. In some embodiments the small hydrophilic domain has a molecular weight less than about 275, 250, 225, 200, 175, 150, 125, 100, and 75 grams/mol.

In some embodiments, the first amphiphilic excipient can be selected from the following types: phospholipids, sphingolipids, cholesterol and steroid derivatives, bile acids and derivatives, cardilipin, acyl-glycerides and derivatives, glycolipids, acyl-peptides, and fatty acids. The phospholipid can be selected from the following types: distearoyl phosphatidylcholine (DSPC); dipalmitoyl phosphatidylcholine; dimysristoyl phosphatidylcholine; dioleoyl phosphatidylcholine; trans-esterified phospholipids derived from eggs, soybean, flaxseed, and the like; phosphatidylethanolamines; phosphatidylglycerol; phosphatidylserine; and phosphatidic acids.

In some embodiments, the first amphiphilic excipient is a fatty acid or fatty acid derivative, as understood in the art. In some embodiments, the fatty acid has an ionized carboxylic acid when at neutral pH.

In some embodiments, the phospholipid is selected from 1-palmitoyl-2-oleoyl-sn-glycero-3-phosphocholine (POPC), dipalmitoylphosphatidylcholine (DPPC), 1,2-dimyristoyl-sn-glycero-3-phosphocholine (DMPC), and the like.

In some embodiments, the first amphiphilic excipient is or comprises steric acid or oleic acid.

In some embodiments, the first amphiphilic excipient comprises at least a first fatty acid tail domain that has at least 14 carbons. In some embodiments, the first amphiphilic excipient further comprises a second fatty acid tail domain that has at least 14 carbons. In some embodiments, at least the first fatty acid tail domain, and optionally the second fatty acid tail domain, comprises 14, 16, 18, 20, and 22 carbon atoms. The first fatty acid tail domain can be completely saturated (i.e., with the maximum number of hydrogens and no double carbon to carbon bonds) or be unsaturated (i.e., have any number of carbon to carbon double bonds). In some embodiments, the first fatty acid tail domain has one or no carbon to carbon bonds. In some embodiments, the first fatty acid tail domain has one, two, three or more carbon to carbon double bonds. In some embodiments, the first amphiphilic excipient comprises at least a first fatty acid tail domain and a second fatty acid tail domain, wherein at least one of the first and second fatty acid tail domains have one or no carbon to carbon double bonds. In one embodiment, the first amphiphilic excipient comprises at least a first fatty acid tail domain and a second fatty acid tail domain, wherein both the first and second fatty acid tail domains have one or no carbon to carbon double bonds. In one embodiment, at least one of the first and second fatty acid tail domains has no carbon to carbon double bonds (i.e., is completely saturated). In one embodiment, both the first and second fatty acid tail domains have no carbon to carbon double bonds (i.e., are completely saturated).

The first amphiphilic excipient can be characterized by a gel-to-liquid phase transition temperature, which is the temperature at which aggregations (e.g., nanoparticles) of the excipients begin to disaggregate and transition into liquid solution. The disclosed multi-drug lipid nanoparticles typically incorporate first amphiphilic excipient with gel-to-liquid phase transition temperature of at least 37° C. In some embodiments, the gel-to-liquid phase transition temperature exceeds 40° C., 45° C., 50° C., 55° C., 60° C., 65° C., or 70° C. (or any intermediate temperature therein). In some embodiments, the gel-to-liquid phase transition temperature can also be determined for the combined excipients of the lipid nanoparticle (i.e., including also at least consideration of the identity and amount of the second amphiphilic excipient).

Figures 8A, 8B, 8C:
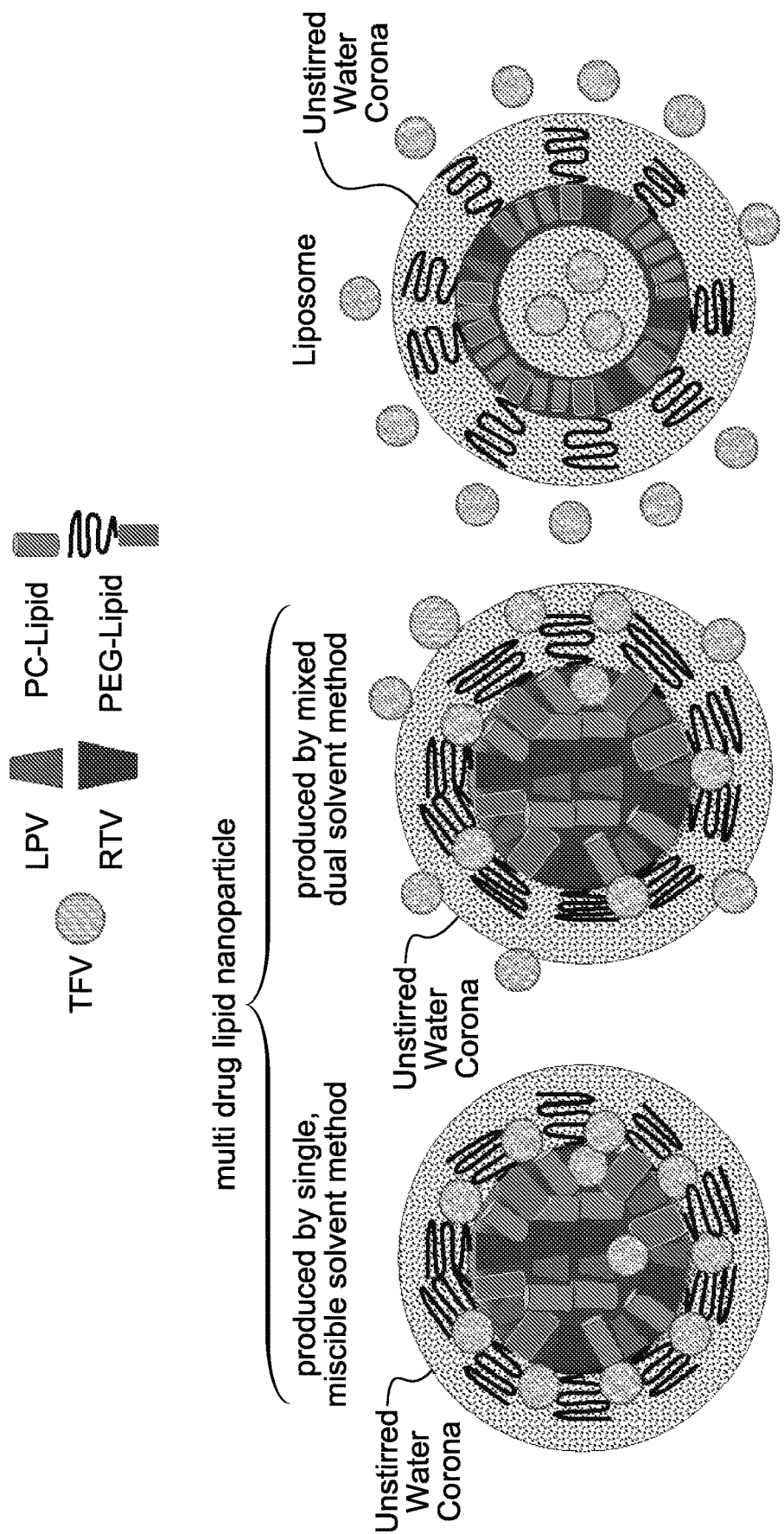
FIGS. 8A-8C schematically illustrate physical characteristics of the multi-drug lipid nanoparticles produced by the disclosed single, miscible solvent method (FIG. 8A) and the mixed dual solvent method (FIG. 8B), as well as typical liposomes (FIG. 8C). The illustrated PEGylated lipids retain hydrophilic drugs present during assembly, but upon formation repel or inhibit incorporation of further agents into the formed unstirred corona. This high rate of tight association of hydrophilic drugs in FIG. 8A require well-mixed drug agents and excipients and complete dehydration prior to rehydration to form the drug lipid nanoparticles. The use of mixed, dual solvent method appears (FIG. 8B) to result in a comparatively looser association of hydrophilic drug agents. As a result, under the sheer force of sucrose gradient centrifugation, the % drug association is greatly reduced to about 7-20% as opposed to 78-85%. The typical liposome's ability to encapsulate hydrophilic drug is much lower and limited by the repulsion or unstirred water (hydration) shell (FIG. 8C). Thus hydrophilic drug such as tenofovir (TFV) is around 3-5% association, a value similar to those reported by other with similar lipid compositions.

The second amphiphilic excipient comprises a large hydrophilic domain, relative to the first amphiphilic excipient. As the second amphiphilic excipient integrated into the lipid nanoparticle, the large hydrophilic domain typically extends beyond the hydrophobic components (e.g., mostly lipid region) into the extraparticle space. The structure of the hydrophobic domain can be quite variable and thus do not limit the scope of the disclosed nanoparticles. These structures create a corona region, as illustrated in FIGS. 8A and 8B, which create a structural refuge area for stable association of hydrophilic small molecule agents to the nanoparticle. The small hydrophilic domain of the second excipient typically has a molecular weight greater than about 500 grams/mol. In some embodiments the large hydrophilic domain has a molecular weight greater than about 500, 750, 1000, 1500, 2000, 2500, 3000, 5000, 7500, 10,000, 15,000, 20,000, 50,000, 100,000, 500,000, 1,000,000, or more grams/mol (or any intermediate molecular weight therein). Selection of an excipient with a particular hydrophilic domain can be informed by the amount of structural refuge intended to be provided to the hydrophilic small molecule agent (which can also be influenced by the relative amount of second excipient.)

In some embodiments, the first amphiphilic excipient can be selected from the following types: glycoproteins, glycolipids, polyalkylene oxide-containing polymers, and polyalkylene oxide-containing lipids. In some embodiments, the polyalkylene oxide-containing lipid is selected from the following types: polyoxyethylene-containing lipids and polyoxypropylene-containing lipids. In some embodiments, the polyoxyethylene-containing lipid is a phospholipid functionalized with polyethylene glycol, wherein the polyethylene glycol has a number average molecular weight from about 500 to about 20,000 g/mol, such as 500, 750, 1000, 1500, 2000, 2500, 3000, 5000, 7500, 10,000, 15,000, 20,000 g/mol (or any intermediate molecular weight therein). In some further embodiments the phospholipid functionalized with polyethylene glycol is N-(carbonyl-methoxypolyethyleneglycol-2000)-1,2-distearoyl-sn-glycero-3-phosphoethanolamine (mPEG-2000-DSPE).

In some embodiments, the polyalkylene oxide-containing lipid is a phospholipid comprising at least a first fatty acid tail domain that has at least 14 carbons. The phospholipid can further comprise a second fatty acid tail domain that also has at least 14 carbons. The discussion above regarding embodiments of the first amphiphilic excipient with respect to embodiments of first and second fatty acid tails having 14 or more carbons and/or being saturated or containing double carbon to carbon bonds is equally applicable to the fatty acid tail(s) of the phospholipid of the second amphiphilic excipient and is not repeated here to avoid further repetition.

The disclosed multi-drug lipid nanoparticles typically have greater number of first defined lipid excipient molecules compared to second excipient molecules. For example, the multi-drug lipid nanoparticle can has a mole ratio of the first amphiphilic excipient to the second amphiphilic excipient of about 2:1 to about 20:1 or higher, such as 2:1, 5:1, 7:1, 10:1, 13:1, 15:1, 18:1, or 20:1 or higher (or any intermediate ration encompassed therein). For example, as described in the below examples, stable multi-drug lipid nanoparticles were assembled with high levels of drug association that had a mole ratio of the first amphiphilic excipient to the second amphiphilic excipient (i.e., ratio of DSPC:DSPE-mPEG$_{2000}$) of about 4:1 and 9:1.

The resulting multi-drug lipid nanoparticles are substantially spherical, meaning that measurements of diameter from different points on the surface through a center point to the opposite side will not vary by more than 50% or less, and preferably will not vary by more than 25% or less. In some embodiments, the multi-drug lipid nanoparticle has a diameter (or average diameter if multiple measurements are taken) of about 20 nm to about 200 nm. In some embodiments, the multi-drug lipid nanoparticle has a diameter or average diameter of about 20 nm to about 150 nm, about 20 nm to about 125 nm, about 20 nm to about 100 nm, about 30 nm to about 90 nm, about 40 nm to about 60 nm, or any intermediate diameter or range of diameters encompassed therein.

As indicated above, the multi-drug lipid nanoparticle has a corona around the exterior surface formed, at least in part, by the hydrophilic domains of the first amphiphilic excipient. The corona is formed by the hydrophilic domains of the second amphiphilic excipients which provide structure in which the hydrophilic small molecule agents can be stably entrapped during assembly and dehydration steps. The corona is hydrophilic in that water and other hydrophilic molecules can reside in the corona. However, due to structural constraints, it is difficult to enter the hydrophilic corona region from an outside aqueous environment once formed. Thus, the hydrophilic domains of the second amphiphilic excipient can repulse molecules from entering the hydrophilic corona. In some embodiments, the hydrophilic corona has a thickness of about 2 nm to about 15 nm when observed in an isotonic buffer (e.g., physiological tonicity) and at physiological pH and 25° C. In some embodiments, the corona has a thickness of about 2, 3, 4, 5, 6, 7, 8, 9, 10, 11, 12, 13, 14, or 15 nm. This corona thickness can be obtained or designed by the choice of hydrophilic domain on the second lipid excipient.

The multi-drug lipid nanoparticle is not a liposome. Liposomes are defined by having a lamellar bilayer of amphiphilic lipids.

In some embodiments, the multi-drug lipid nanoparticle does not have a solid core. Such solid cores, for example, can comprise metal particulates and the like, which are coated with lipids and the like.

As described herein the multi-drug lipid nanoparticles produced according to the present disclosure and encompassed in the present invention have enhanced properties, including a stable and surprisingly high association rate of different small molecule agents. Accordingly, in some embodiments, the multi-drug lipid nanoparticle is characterized by having at least about 70%, such as 70%, 75%, 80%, 85%, or more, of the first small molecule agent(s) remaining associated with the nanoparticle after 24 hours at pH 7.4 and 25° C. In some embodiments, the multi-drug lipid nanoparticle is characterized by having at least 7%, such as about 7%, 8%, 9%, 10%, 15%, 20%, 25%, 30%, 35%, 40%, 45%, 50%, 55%, 60%, 65%, 70%, 75%, 80%, 85%, or more of the second small molecule agent(s) remains associated with the nanoparticle after 24 hours at pH 7.4 and 25° C. As described in more detail below, the method of lipid nanopore assembly can affect the structure of the resulting lipid nanoparticle and, thus, affects the ability to retain associated hydrophilic (i.e., second) small molecule agents. In this regard, nanoparticles produced from the single, miscible solvent method can retain approximately 75% or more of the hydrophilic drugs used during the assembly process (see Table 21), and the disclosed lipid nanoparticles are quite stable during long term storage. In some embodiments, at least about 70%, such as about 75%, 80%, 85%, or more, of the combined first and second small molecule agents remains associated with the nanoparticle after 8 months at pH 7.4 and 4° C. In some embodiments, at least about 60%, such as 70%, 75%, 80% or more, of the combined first and second small molecule agents remains associated with the multi-drug lipid nanoparticle after 8 months at pH 7.4 and 4° C.

In some embodiments, at least 70%, such as about 75%, 80%, 85%, or more, of the small molecule agents remains associated with the nanoparticle when the nanoparticle is subjected to a sucrose gradient test. In some embodiments, at least 70%, such as about 75%, 80%, 85%, or more, of the second (i.e., hydrophilic) small molecule agents remains associated with the nanoparticle when the nanoparticle is subjected to a sucrose gradient test. The sucrose gradient test to determine this characteristic is described in Example 5. Briefly, the sucrose gradient test comprises subjecting the multi-drug lipid nanoparticle to a continuous 5%-20% sucrose gradient and applying a centrifugal force of 200,000 g for 4 hours. The unassociated small molecules separate and float to the less dense fractions, whereas the associated small molecule agents sediment with the stable lipid nanoparticles in the denser gradients. The relative amounts of the unassociated and associated small molecule reagents can be quantified and, thus, compared.

As described below, the multi-drug lipid nanoparticles can exhibit pH-responsiveness in that amounts of associated small molecule agents are increasingly released from the lipid nanoparticles as the pH is reduced. Thus, there is an advantage of drug products being delivered primarily upon uptake of the lipid nanoparticles by cells by endocytosis and exposure to decreased pH within the cells' lysosomal vesicles, for example. This preserves a much higher proportion of administered drugs for delivery to actual intended targets instead of providing merely an initial systemic spike followed by immediate clearance.

In some embodiments, the disclosed multi-drug lipid nanoparticle confers extended plasma concentration of the first small molecule agent and second small molecule agent after administration to a mammalian subject as compared to the administration of the same amount of free small molecule agents to the mammalian subject. For example, upon administration of an amount effective to influence the state of a disease or infection, the amounts of the first small molecule agent and second small molecule agent remain detectable in the plasma or lymphoid tissue for a period of time exceeding 3, 4, 5, 6, 7, 8, 9, 10, 11, 12, 13, 14, 15, 16, 17, 18, 19, 20 or more days. This is in contrast to the presence of the first small molecule agent and second small molecule agent when administered in free form (i.e., not associated with a lipid nanoparticle formulation), which often falls below detectable levels within one or two days.

As described herein, the extended presence in the plasma and lymphoid tissue is advantageous for maintaining exposure of pathogens or other disease targets to the small molecule therapeutic agents. Furthermore, the combination of multiple small molecule agents into a single, stable vehicle ensures that both (or all) of the therapeutic agents interact with their intended targets simultaneously and with relevant, effective levels to facilitate efficient multi-drug combination therapy such as cART. Accordingly, the disclosed multi-drug lipid nanoparticles enhance or increase the efficacy and/or potency of the small molecule agents incorporated therein relative to the potency/efficacy of the small molecule agents in free form or in a form where each is formulated in separate delivery vehicles.

It will be appreciated that the disclosed multi-drug lipid nanoparticles can further comprise any relevant components to enhance or direct functionality. For example, it is within the skill of skilled artisans to routinely incorporate detectable labels for purposes of providing imaging functionality. Furthermore, the multi-drug lipid nanoparticles can further comprise targeting molecules, such as receptors, lectins, antibodies, and functional fragments or derivatives thereof. For example, for antibodies this can encompass single chain antibodies (e.g., single chain variable fragment (scFv), single-chain Fab fragment (scFab), VHH fragment, VNAR, or nanobody), bispecific antibodies, Fab fragments, or an F(ab)2 fragments). These can facilitate the directed delivery of the associated small molecule therapeutic agents to targets of interest that have unique antigens specifically recognized by the targeting molecules. Moreover, the multi-drug lipid nanoparticles can further comprise other binding partners (e.g., biotin, streptavidin) to assist conjugation or linking with other functional structures. Such exemplary additional components can be integrated or conjugated to the disclosed lipid nanoparticles using techniques familiar in the art.

In another aspect, the disclosure provides pharmaceutical compositions comprising the multi-drug lipid nanoparticles disclosed herein. The pharmaceutical compositions can include a pharmaceutically acceptable aqueous carrier as understood in the art. In In another aspect, the disclosure provides a pharmaceutical composition comprising the multi-drug lipid nanoparticles disclosed herein. However, in this aspect multi-drug lipid nanoparticles are provided in a dry form, such as powder, which can be reconstituted with a sterile saline buffer prior to administration. Embodiments of the dry powder form include a first small molecule agent with a log P at 25° C. greater than 1; a second small molecule agent with a log P at 25° C. less than 0; a first amphiphilic excipient, wherein the first amphiphilic excipient is a lipid comprising a hydrophilic domain with a molecular weight less than 300 grams/mol; and a second amphiphilic excipient comprising a hydrophilic domain with a molecular weight greater than 500 grams/mol.

In yet another aspect, the disclosure provides a kit comprising the formulation disclosed herein. In some embodiments, the kit also comprises a reconstitution buffer and written indicia directing reconstitution and administration procedures.

In another aspect, the disclosure provides a method of preparing a multi-drug lipid nanoparticle. The method of this aspect is also referred to herein as the mixed dual solvent method. This method comprises dissolving in an organic solvent a first small molecule agent with a log P at 25° C. greater than 1, a first amphiphilic excipient wherein the first amphiphilic excipient is a lipid comprising a hydrophilic domain with a molecular weight less than 300 grams/mol, and second amphiphilic excipient comprising a hydrophilic domain with a molecular weight greater than 500 grams/mol, to provide an organic solvent solution. The method also comprises dissolving in an aqueous solvent a second small molecule agent with a log P at 25° C. less than 0 to provide an aqueous solvent solution. The organic solvent solution and the aqueous solvent solution are mixed to provide a mixed solvent solution. Next, the mixed solvents are removed from the mixed solvent solution to provide a dehydrated product comprising the first small molecule agent, the first amphiphilic excipient, the second amphiphilic excipient, and the second small molecule agent. The dehydrated product is rehydrated in an aqueous solution to provide a solution with multi-drug lipid nanoparticles.

The organic solvent comprises a subcomponent that is miscible with water. In some embodiments, the organic solvent comprises another subcomponent that is immiscible with water. Miscibility refers to the ability to mix with water or another aqueous solution without forming and emulsion (i.e., separation of phases). Water miscibility, when it exists, is typically limited by the amount of water included in the solution. Thus, a person of ordinary skill in the art will readily appreciate that the relative amount of aqueous solvent in a mixed solution must be limited.

In some embodiments, the organic solvent solution and the aqueous solvent solution are mixed at a ratio of at least about 20:1 (v/v). In some embodiments, the organic solvent solution and the aqueous solvent solution are mixed at a ratio of at least about 20:1, 21:1, 22:1, 23:1, 24:1, 25:1, 26:1, 27:1, 28:1, 29:1, 30:1, 35:1, 40:1, 60:1, or more (v/v) (or any intermediate ratio encompassed therein).

Organic solvents known to be generally miscible with water are known and include acetic acid, acetone, acetonitrile, dimethylformamide, dimethyl sulfoxide, dioxin, ethanol, methanol, propanol (and other alcohols), and tetrahydrufuran. In one embodiment, the water-miscible subcomponent of the organic solvent is an alcohol. In further embodiments, the alcohol is selected from methanol, ethanol, propanol, hexanol, and decanol. In another embodiment, the water-miscible subcomponent of the organic solvent is acetonitrile.

In some embodiments, the organic solvent consists of the water-miscible subcomponent. However, in other embodiments, the organic solvent also comprises a subcomponent that is water immiscible. In this sense, in isolation, this subcomponent would not mix with water or an aqueous solution without forming separate phases. However, only with the co-mixing with the water miscible component, described above, can this water immiscible component be combined in a single phase with the water or aqueous solution. Organic solvents known to be generally immiscible with water are known and include benzene, butyl alcohol, carbon tetrachloride, chloroform, cyclohexane, cylcopentane, dichloroethane, dichloromethane, ethyl acetate, diethyl ether, heptane, hexane, methylethyl ketone, octane, pentane, di-propyl ether, tetrachloroethane, toluene, trichloroethane, and xylene. In some embodiments, the water immiscible subcomponent is selected from chloroform, hexane, decane, methylene chloride, and a combination thereof.

In some embodiments, the water-immiscible subcomponent is chloroform and the water-miscible subcomponent is an alcohol, such as any one of methanol, ethanol, propanol, hexanol, and decanol.

In some embodiments, the ratio of water immiscible subcomponent to water miscible subcomponent (v/v) of the organic solvent is from about 1:1 to about 4:1. In some embodiments, the ratio is about 7:5 (i.e., 1.4:1) to about 4:1. In some embodiments, the ratio is about 2:1 to about 3:1. In one embodiment described in more detail below, the ratio of water immiscible subcomponent to water miscible subcomponent (v/v) of the organic solvent is 65:35 (i.e., 13:7) for chloroform to an alcohol.

The aqueous solvent can be any appropriate solvent in which to dissolve the hydrophilic small molecule of choice. Examples include aqueous solvents comprising $NaHCO_3$, phosphate, borate, citrate, glycine, or a combination thereof, but need not be so limited.

The mixed organic and aqueous solvents can be removed from the mixed solvent solution using evaporation, such as facilitated by application of vacuum-facilitated by vacuum desiccation. Other techniques for drying or removing solvents are known and are encompassed by the disclosed method. In some embodiments, the dehydrated product is substantially dried, wherein trace levels (e.g., less than 3% of the original volume) of solvent remains. In some embodiments the dehydrated product is completely or nearly completely dried.

In some embodiments of the method, the dehydrated product is rehydrated in the aqueous solution at a temperature that is at least at about 3° C. above a gel-to-liquid phase temperature of the amphiphilic excipients. As indicated above, the gel-to-liquid phase temperature is the temperature at which aggregations (e.g., nanoparticles) of the excipients begin to disaggregate and transition into liquid solution. The gel-to-liquid phase transition temperature can be determined by structural properties of the first amphiphilic excipient, or alternatively by combined excipients of the lipid nanoparticle (i.e., including at least consideration of the identities and amounts of the amphiphilic excipients). In some embodiments, the dehydrated product is rehydrated in the aqueous solution at a temperature that is at least at about 3° C., 4° C., 5° C., 6° C., 7° C., 8° C., 9° C., 10° C., 15° C., 20° C. or more (or any intermediate temperature encompassed therein) above a gel-to-liquid phase temperature of the amphiphilic excipient(s). In some embodiments, depending on the excipients used, the method comprises maintaining the temperature of the aqueous solution during mixing at least at 40° C., 45° C., 50° C., 55° C., 60° C., 65° C., 70° C., or higher (or any intermediate temperature encompassed therein).

In some embodiments, the mixed solvent phase has a mole ratio of small molecule agents to excipients that is at least about 1:10. In some embodiments, the resulting multi-drug lipid nanoparticle has a mole ratio of small molecule agents to excipients that is at least about 1:10. Other characteristics described above for the disclosed multi-drug lipid nanoparticles are applicable to the multi-drug lipid nanoparticles produced by this disclosed method.

In another aspect, the disclosure provides a method of preparing a multi-drug lipid nanoparticle. The method of this aspect is also referred to herein as the single, miscible solvent method. This method comprises dissolving in a miscible solvent the following: a first small molecule agent with a log P at 25° C. greater than 1, a second small molecule agent with a log P at 25° C. less than 0, a first amphiphilic excipient wherein the first amphiphilic excipient is a lipid comprising a hydrophilic domain with a molecular weight less than 300 grams/mol, and a second amphiphilic excipient comprising a hydrophilic domain with a molecular weight greater than 500 grams/mol. The miscible solvent is removed to provide a dehydrated product comprising the first small molecule agent, the second small molecule agent, the first amphiphilic excipient, and the second amphiphilic excipient. The dehydrated product is heated to a first temperature that is at least 3° C. above a gel-to-liquid phase transition temperature of the amphiphilic excipients. The dehydrated product is rehydrated in an aqueous solution to provide a solution with multi-drug lipid nanoparticles.

In some embodiments, the miscible solvent comprises an organic component and an aqueous component at a ratio of between about 20:1 and about 40:1 (v/v), such as about 20:122:1, 25:1, 27:1, 30:1, 32:1, 35:1, 37:1, and 40:1 (or any intermediate ratio encompassed therein). In some embodiments, the organic component of the miscible solvent comprises a subcomponent that is miscible with water. In additional embodiments, the organic component of the miscible solvent also comprises a subcomponent that is immiscible with water. The above descriptions of the water-miscible and water-immiscible subcomponents, and relative ratios thereof in the organic solvent are applicable to the organic subcomponents, and ratios thereof, in the organic component of the miscible solvent of this aspect and are not repeated here.

In some embodiments, the water-immiscible subcomponent is chloroform and the water-miscible subcomponent is an alcohol, such as any one of methanol, ethanol, propanol, hexanol, and decanol.

The above description of the aqueous solvent is applicable to the aqueous subcomponent of the miscible solvent and is not repeated here.

In some embodiments, removing the miscible solvent comprises evaporating, desiccating under reduced pressure, spray drying, or a combination thereof. Other techniques for drying or removing solvents are known and are encompassed by the disclosed method. In some embodiments, the dehydrated product is substantially dried, wherein trace levels (e.g., less than 3% of the original volume) of solvent remains. In some embodiments the dehydrated product is completely or nearly completely dried.

In some embodiments, the first temperature is at least at about 3° C., 4° C., 5° C., 6° C., 7° C., 8° C., 9° C., 10° C., 15° C., 20 or more (or any intermediate temperature encompassed therein) above a gel-to-liquid phase temperature of the amphiphilic excipient(s).

In some embodiments, the aqueous solution is maintained at least at the first temperature during the rehydrating step. As indicated, the first temperature is at least about 3° C. above a gel-to-liquid phase temperature of the amphiphilic excipient(s). In some embodiments, depending on the excipients used, the method comprises maintaining the temperature of the dehydrated product and/or the aqueous solution during mixing at least at 40° C., 45° C., 50° C., 55° C., 60° C., 65° C., 70° C., or higher (or any intermediate temperature encompassed therein). In one embodiment, the rehydrating step comprises gradually combining the dehydrated product and the aqueous solution at about the first temperature, and maintaining the fully combined dehydrated product and aqueous solution at a second temperature that is at least the first temperature for at least about 1 hour.

The resulting multiple drug lipid nanoparticles can have an average mole ratio of small molecule agent to excipient of at least about 1:5, such as about 1:4, 1:3 or more. In another embodiment, at least about 70% of the first small molecule agent and at least about 70% of the first small molecule agent are stably associated with the resulting multiple drug lipid nanoparticles at neutral pH. Other characteristics described above for the disclosed multi-drug lipid nanoparticles are applicable to the multi-drug lipid nanoparticles produced by this disclosed method.

Furthermore, the above disclosed method aspects can further comprise, or be characterized by, additional features.

In some embodiments, the methods further comprise agitating the aqueous solution comprising multiple drug lipid nanoparticles to reduce the size of the multiple drug lipid nanoparticles. The agitation step can comprise applying sonication, extrusion through one or more filters, or mechanical or hydrodynamic sheering disruption. Such agitating step can result in multiple drug lipid nanoparticles where at least 90% by number of the lipid nanoparticles have a diameter of about 20 nm to about 200 nm. Thus, the average diameter can be about 20 nm to about 150 nm, about 20 nm to about 125 nm, about 20 nm to about 100 nm, about 30 nm to about 90 nm, about 40 nm to about 60 nm, or any intermediate diameter or range of diameters encompassed therein.

Structural and functional aspects regarding the multi-drug lipid nanoparticles described in other aspects or sections of this disclosure, for example regarding the corona, component first small molecules, component second small molecules, the component first amphiphilic excipient, the second amphiphilic excipient, and their respective log P values and hydrophilic domains, the relative ratios of the component parts (e.g., small molecule agents and excipients), and the like, are applicable to the multi-drug lipid nanoparticle produced by the method, and are not repeated here.

In another aspect, the disclosure encompasses any multi-drug lipid nanoparticle produced by the disclosed methods.

As described below, the inventors demonstrated the utility and efficacy of the assembly methods to produce multi-drug lipid nanoparticles that incorporate both hydrophilic and hydrophobic small molecule agents that are approved for use against HIV infection. Accordingly, in another aspect, the disclosure provides a method of treating subject infected with HIV, comprising administering an effective amount of the multi-drug lipid nanoparticles disclosed herein or administering an effective amount of a pharmaceutical composition disclosed herein. As used herein, the term "treating" refers to slowing, reducing, or preventing viral replication, and/or ameliorating symptoms associated with viral infection.

The administration can be to any mammal that can harbor HIV. Administration can be through any appropriate route that provides systemic delivery of the multi-drug lipid nanoparticles, for example subcutaneous (SC), intravenous (IV), or intramuscular (IM).

In some embodiments, the viral burden is detectably lowered in the lymph tissue of the subject. In some embodiments, the disclosed multi-drug lipid nanoparticle confers extended plasma concentration of the first small molecule agent and second small molecule agent after administration to a mammalian subject as compared to the administration of the same amount of free small molecule agents to the mammalian subject. For example, upon administration of an amount effective to influence the state of a disease or infection, the amounts of the first small molecule agent and second small molecule agent remain detectable in the plasma or lymphoid tissue for a period of time exceeding 3, 4, 5, 6, 7, 8, 9, 10, 11, 12, 13, 14, 15, 16, 17, 18, 19, 20 or more days.

As described herein, the extended presence in the plasma and lymphoid tissue is advantageous for maintaining exposure of the virus to the small molecule therapeutic agents. Furthermore, the combination of multiple small molecule agents into a single, stable vehicle ensures that both (or all) of the therapeutic agents interact with their intended targets simultaneously and with relevant, effective levels to facilitate efficient multi-drug combination therapy such as cART. Accordingly, the disclosed multi-drug lipid nanoparticles enhance or increase the efficacy and/or potency of the small molecule agents incorporated therein relative to the potency/efficacy of the small molecule agents in free form or in a form where each is formulated in separate delivery vehicles.

The present disclosure also encompasses methods of treating other diseases and infections by incorporating appropriate multiple small molecule agents (e.g., combining hydrophilic and hydrophobic small molecule agents, as described) that target to distinct mechanisms influencing the indicated disease or infective pathogens.

Unless specifically defined herein, all terms used herein have the same meaning as they would to one skilled in the art of the present invention. Publications cited herein and the subject matter for which they are cited are hereby specifically incorporated by reference in their entireties.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

EXAMPLES

The following examples are intended to illustrate, but not limit, the disclosed invention.

Example 1

This example describes the evaluation of Atazanavir and Darunavir interactions with lipids for developing pH-responsive anti-HIV drug combination nanoparticles.

Abstract

We evaluated two human immunodeficiency virus (HIV) protease inhibitors, atazanavir (ATV) and darunavir (DRV), for pH-dependent solubility, lipid binding, and drug release from lipid nanoparticles (LNPs). Both atazanavir and darunavir incorporated into lipid nanoparticles composed of pegylated and non-pegylated phospholipids with nearly 100% efficiency, but only atazanavir lipid nanoparticles formed stable lipid-drug particles and exhibited pH-dependent drug release. Darunavir lipid nanoparticles were unstable and formed mixed micelles at low drug-lipid concentrations, and thus are not suitable for lipid-drug particle development. When atazanavir lipid nanoparticles were prepared with ritonavir (RTV), a metabolic and cellular membrane exporter inhibitor, and tenofovir (TFV), an HIV reverse transcriptase inhibitor, stable, scalable, and reproducible anti-HIV drug combination lipid nanoparticles were produced. Drug incorporation efficiencies of 85.5±8.2, 85.1±7.1, and 6.1±0.8% for atazanavir, ritonavir, and tenofovir, respectively, were achieved. Preliminary primate pharmacokinetic studies with these pH-responsive anti-HIV drug combination lipid nanoparticles administered subcutaneously produced detectable plasma concentrations that lasted for 7 days for all three drugs. These anti-HIV lipid nanoparticles could be developed as a long-acting targeted antiretroviral therapy.

Introduction

Highly active antiretroviral therapy (HAART), introduced in the late 1990s and targeted to multiple viral proteins, clears human immunodeficiency virus (HIV) in the blood and has resulted in significant improvement in the quality of life and life-expectancy in HIV infected patients. Although oral HAART therapy is very effective in clearing HIV from the blood, residual virus persists in lymph nodes and other lymphoid tissues even with high drug doses. We previously described that in HIV infected patients on the oral anti-HIV drug indinavir, intracellular drug concentrations in mononuclear cells of lymph nodes exhibited levels that were one-third of those found in blood mononuclear cells. These data were recently confirmed in a prospective clinical study in 12 HIV infected patients, where it was found that lymph node intracellular drug levels for two HIV drugs (atazanavir, ATV, and darunavir, DRV) were as much as 99% lower than those in blood. These lower intracellular drug levels in lymph nodes correlated with residual virus in the patients.

Previously, we systematically developed pH-sensitive indinavir lipid nanoparticles and demonstrated that they preferentially localize in lymph nodes and lymphoid tissues when given subcutaneously. In HIV-infected primates, we reported that these lipid-indinavir complexes enhanced indinavir concentrations in lymph nodes throughout the body with drug levels up to 22.7-fold higher than in plasma. These studies showed significant plasma virus load reductions and reversal of CD4+ T cell decline. No enhancement in lymph nodes drug accumulation or clinical impact was seen in control primates treated with free drug.

However, for clinical translation, a combination of anti-HIV drugs—more than indinavir monotherapy—is necessary to address potential drug resistance. Recent acquired immunodeficiency syndrome (AIDS) treatment guidelines recommend a number of drug combinations, most of which include at least two or three different anti-HIV drugs. Among the protease inhibitors used in HAART, a number of newer anti-HIV drugs that exhibit 10-100-fold higher antiviral potency and a lower rate of drug resistance are now available. ATV and DRV are new generation protease inhibitors typically used in combination with ritonavir (RTV), another protease inhibitor, and tenofovir (TFV), a reverse transcriptase inhibitor.

Therefore, the aim of this research was to characterize the lipid-drug interactions of the new protease inhibitors ATV and DRV with respect to membrane binding, degree of incorporation, stability, and pH-dependent release of drugs. These studies provide the basis for developing pH-responsive anti-HIV drug combination lipid nanoparticles composed of polyethylene glycol polymer modified lipid and phospholipid mixture that are stable and can be scaled with high incorporation efficiency of protease inhibitors for primate study. Our results indicate that both ATV and DRV bind to lipid and incorporate predominantly into lipid membrane, but only ATV-lipid nanoparticles (ATV-LNPs) are stable and exhibit pH sensitivity. Thus, ATV-containing nanoparticles are suitable for further development of anti-HIV drug combination lipid nanoparticles containing ATV, RTV, and TFV.

Materials and Methods

Materials 1,2-distearoyl-sn-glycero-3-phosphocholine (DSPC) and 1,2-distearoyl-sn-glycero-3-phosphoethanolamine-N-[poly (ethylene glycol)2000] (DSPE-mPEG$_{2000}$) (both GMP-grade) were purchased from Genzyme Pharmaceuticals (>99% purity; Cambridge, Mass.). Atazanavir (C38H52N6O7, ATV), darunavir (C27H37N3O7S, DRV), ritonavir (C37H48N6O5S2, RTV), and tenofovir (C9H14N5O4P, TFV) reference standards were provided by the National Institutes of Health (NIH) AIDS Research and Reference Reagent Program. Some later samples were purchased from Waterstonetech LLC (Carmel, Ind.) and verified with a reference compound. Cyheptamide was purchased from Sigma-Aldrich (St. Louis, Mo.). 1,6-diphenyl-1,3,5-hexatriene (DPH) was obtained from Invitrogen (Eugene, Oreg.). Other reagents were of analytical grade or higher.

Determination of Atazanavir and Darunavir Distribution Coefficient in Octanol and Buffer The octanol-buffer drug distribution coefficient at room temperature was determined by a small-scale, shake-flask method described by Dittert L W, et al. Phase Solubility Technique in Studying the Formation of Complex Salts of Triamterene. *Journal of pharmaceutical sciences.* 1964; 53:1325-1328. Briefly, phosphate-buffered saline (PBS) at pH 3, 5, and 7.4 was used as the aqueous phase. 0.2 mg/mL of ATV or DRV was dissolved in octanol, added to an equal volume of PBS, and vortexed for 10 min. The mixture was centrifuged at 14,000 rpm (18,078 g) (Beckman Coulter™ Microfuge® 18 centrifuge, Beckman Coulter Inc., Brea, Calif.) to separate octanol and the aqueous phase. The drug concentration in the two phases was determined with high-performance liquid chromatography tandem mass spectrometry (HPLC/MS/MS). The distribution coefficient was calculated as the ratio of the drug concentration in the octanol phase to the drug concentration in the aqueous phase. Triplicate samples were used at each pH.

Lipid-Drug Nanoparticle Preparation Lipid-drug nanoparticles were prepared as described previously in Kinman L, et al. Optimization of lipid-indinavir complexes for localization in lymphoid tissues of HIV-infected macaques. *J Acquir Immune Defic Syndr.* 2006; 42(2):155-161; Choi S U, et al. pH-dependent interactions of indinavir and lipids in nanoparticles and their ability to entrap a solute. *Journal of pharmaceutical sciences.* 2008; 97(2):931-943; and Endsley A N and Ho R J. Design and characterization of novel peptide-coated lipid nanoparticles for targeting anti-HIV drug to CD4 expressing cells. *The AAPS journal.* 2012; 14(2):225-235, each incorporated herein by reference in its entirety. Briefly, DSPC and DSPE-mPEG2000 lipids (8:2, mol/mol) and ATV, DRV, and RTV were dissolved in chloroform in a glass tube, then dried under nitrogen gas until a uniform lipid-drug film was formed. Residual solvent was removed overnight by vacuum desiccation. The dried lipid-drug film was then rehydrated with 0.9% NaCl containing 20 mM sodium bicarbonate (pH 7.4). The lipid-drug samples were allowed to hydrate at 60° C. for 2 h. Then samples were sonicated (laboratory scale) or homogenized (preclinical scale) to achieve a homogenous suspension.

For small-scale preparation of lipid nanoparticles, 200 μL samples were sonicated using a bath-type sonicator (Avanti® Polar Lipids Inc., Alabaster, Ala.) until the sample was transparent. For large-scale preparation, 45 mL hydrated lipid-drug mixtures were homogenized for 15 cycles with an Avestin EmulsiFlex-05 (Avestin Inc., Ottawa Ontario, Canada) operating at 5,000-6,000 psi. Osmolality of the final preparation was measured with a VAPRO™ 5520 vapor pressure osmometer (Wescor Inc., Logan, Utah). Lipid-drug nanoparticles and liposome control samples were stored at 4-8° C.

Drug Incorporation Efficiency

The percentage of ATV, DRV, RTV, and TFV incorporated into lipid-drug nanoparticles was determined using a dialysis method. Briefly, a 50 μL aliquot of the lipid-drug nanoparticle preparation was transferred into a dialysis membrane (MW cut-off=6,000-8,000; Spectra/Por® 6, Spectrum Laboratories Inc., Rancho Dominguez, Calif.) and dialyzed in 1,000 mL buffer at pH 7.4 to separate free drug from nanoparticle-incorporated drug. The incorporation efficiency was calculated as the ratio of the amount of incorporated drug over the total amount of drug loaded multiplied by 100%.

Particle Size Analysis

The mean particle size of lipid-drug nanoparticles and liposome control was determined by photon correlation spectroscopy (PCS) using a NICOMP™ 380ZLS instrument (NICOMP Particle Sizing Systems, Santa Barbara, Calif.). Lipid nanoparticle formulations were diluted to 0.25 mM in saline buffer for size measurement (0.4 mL final volume), and evaluated at a 90° angle using a 5 mW HeNe laser (X, =632.8 nm). Samples were diluted with the same buffer to an identical final volume to analyze concentration effects. The light scattering data were analyzed based on intensity-weight NICOMP size distribution and expressed as a mean±SD.

Fluorescence Anisotropy Study to Measure the Membrane Fluidity

To evaluate the change in membrane fluidity due to drug insertion into the lipid membrane, 0.1% 1,6-diphenyl-1,3,5-hexatriene (DPH) was used as an intra-membrane probe.[18,20] Briefly, to incorporate DPH into the lipid membrane, 2 μL of 2 mM DPH in tetrahydrofuran was added to the lipid nanoparticle suspension with or without drug. The final preparation was incubated at 60° C. (above the 55° C. DSPC phase transition temperature) for 30 min, then slowly cooled to room temperature over 15 min. Lipid nanoparticles containing DPH (drug-loaded and empty) were added to a cuvet that was warmed to 45° C. and then gradually increased to 65° C. by 1-2° C. increments. A water-jacketed cuvette holder connected to a circulating water bath (PolyScience, model 1162, Niles, Ill.) was used to control the temperature within the cuvette, which was measured by a digital thermometer. The cuvette was allowed to equilibrate for 10 min before taking each temperature reading. The fluorescence intensities, both parallel and perpendicular to the emission light, were measured continuously with a F-4500 fluorescence spectrometer (Hitachi, Minato-ku, Tokyo, Japan) set at kex/em=360/430 nm; both excitation and emission slits were 5 nm. Fluorescence anisotropy response, r, was calculated by the equation:

$$r = \frac{I_{VV} - I_{VH}}{I_{VV} + 2I_{VH}}$$

where IVV and IVH are the fluorescence intensities recorded with a polarizer oriented parallel and perpendicular to the plane of polarization of the excitation beam.

The fluorescence anisotropy response versus temperature curve was generated by non-linear regression using SigmaPlot software (11.0 version, Systat Software, Inc., San Jose, Calif.). The mid-point of phase transition temperature ($T_C$) was estimated based on the following equation:

$$y = \min + \frac{\max - \min}{1 + \left(\frac{x}{T_c}\right)^{-Hillslope}}$$

where y is fluorescence anisotropy, x represents temperature (° C.), min is the minimum response, max is the maximum response, $T_C$ is the temperature value midway between the min and max parameters, and Hillslope is the slope at $T_C$.

Determination of Drug Release from Lipid-Drug Nanoparticles

Time and pH-dependent drug release from lipid-drug nanoparticles were determined using a dialysis method similar to that described above. Briefly, a 50 μL aliquot of the lipid-drug nanoparticle preparation was transferred into a dialysis membrane (MW cut-off=6,000-8,000; Spectra/Por® 6, Spectrum Laboratories Inc., Rancho Dominguez, Calif.) and dialyzed in 1,000 mL buffer at pH 3, 4, 5, 6, or 7.4 to evaluate pH-dependent drug release and separate free drug from nanoparticle-incorporated drug. The initial and final drug concentration were determined by HPLC/MS/MS (method described below) to estimate the percentage of drug release.

Plasma-Time Course of Anti-HIV Drug Combination Lipid Nanoparticles in Primates

Macaques (*Macaca nemestrina*, male, 2.9-5.0 kg) were used for the pharmacokinetic study, according to the Washington National Primate Research Center guidelines. All animal procedures were performed under an approved protocol reviewed by the University of Washington Institutional Animal Care and Use Committee.

Two young adult male macaques were given a single 20 mL subcutaneously injection of lipid nanoparticles, containing a combination of ATV, RTV, and TFV at a dose of 25 mg/kg ATV (35 μmol/kg), 12.8 mg/kg RTV (18 μmol/kg), and 15.3 mg/kg TFV (53 μmol/kg). Venous blood samples were collected from a femoral vein at 0, 0.5, 1, 3, 5, 8, 24, 48, 120, and 168 hours (7 days). 2 mL of plasma was immediately isolated from the blood by 10 min of centrifugation at 1,200 rpm (252 g) (Jouan CR 312 centrifuge, Jouan Inc., Winchester, Va.). ATV, RTV, and TFV in the plasma were extracted in duplicate and analyzed with a liquid chromatography-mass spectrometry assay with a validated reverse phase HPLC/MS/MS method, similar to that of lopinavir (LPV), RTV, and TFV. Koehn J and Ho R J. A Novel LC/MS/MS Method for Simultaneous Detection of anti-HIV Drugs Lopinavir, Ritonavir and Tenofovir in Plasma. *Antimicrobial agents and chemotherapy.* 2014.

The linear trapezoidal method was used to calculate the area under the plasma drug concentration-time curve (AUC) for ATV, RTV, and TFV during the time course, which was close to 168 h post-dosing. According to the reported ATV, RTV, and TFV plasma half-life (product label), and our preliminary data in primates administered with these drugs (data not shown), ATV, RTV, and TFV were mostly cleared from the blood after 8 h. Therefore, to delineate the impact of free drug versus lipid-bound drug, we analyzed the AUC for three continuous periods: 0-8 h, 8-168 h, and 0-168 h.

Analysis of Multiple Anti-HIV Drugs by HPLC/MS/MS

All drugs in buffer and plasma were analyzed using a validated HPLC/MS/MS analytical method, capable of analyzing ATV, DRV, LPV, RTV, and TFV. The one-step analysis for LPV, RTV, and TFV was published previously. Koehn J and Ho R J. A Novel LC/MS/MS Method for Simultaneous Detection of anti-HIV Drugs Lopinavir, Ritonavir and Tenofovir in Plasma. *Antimicrobial agents and chemotherapy.* 2014. Briefly, the HPLC system was outfitted with a Shimadzu 20AD HPLC (Shimadzu Scientific Instruments, Inc., Pleasanton, Calif.). ATV, RTV, and TFV were separated on a reverse phase Synergi™ column (100×2.0 mm2; 4 μm POLAR-RP 80 Å, Phenomenex Inc., Torrance, Calif.) and were detected with an quadrupole tandem mass spectrometer, MS/MS (AB SCIEX 3200 QTRAP®, Framingham, Mass.). An aliquot of internal standard, cyhepamide, was added to the plasma samples at a final concentration of 50 ng/mL. 5 μL of sample (with internal standard) was injected onto the column, and eluted at a flow rate of 0.35 mL/min with a mobile phase containing acetonitrile and water with 0.1% acetic acid, with a 3-100% gradient. Multiple reaction monitoring (MRM) was used to detect transition ions from a specific precursor ion to product ion. The analytes were detected using the following m/z transitions: 705.5/168.2 for ATV, 548.3/392.3 for DRV, 721.3/296.1 for RTV, 288.1/176 for TFV, and 238.1/193.2 for cyheptamide.

while ATV and DRV are both lipophilic (Log D of ~3 or higher at neutral pH), only ATV exhibits a progressive increase in Log D with increasing pH.

TABLE 1

Molecular structure and pH-dependent hydrophobicity of atazanavir and darunavir

| Hydrophobicity | pH | Atazanavir (ATV) | Darunavir (DRV) |
|---|---|---|---|
| Log D (measured)[a] | 3 | 3.40 ± 0.31 | 2.98 ± 0.02 |
|  | 5 | 4.66 ± 0.27 | 2.80 ± 0.02 |
|  | 7.4 | 5.77 ± 0.03 | 2.84 ± 0.07 |
| XLogP3-AA (estimate)[b] |  | 5.6 | 2.9 |
| pKa[c] |  | 4.42, 11.92 | 2.39, 13.59 |

[a]Distribution coefficient, log D, was measured as described in Materials and Methods for each pH value and presented as a mean ± SD of triplicates.
[b]Theoretical estimates were derived from the PubChem database (ref: online at pubchem.ncbi.nlm.nij.gov and sioc-ccbg.ac.cn/software/xlogp3).
[c]Drug bank data, estimated by ChemAxon (online at drugbank.ca/drugs/DB01072 for ATV; drugbank.ca/drugs/DB01264 for DRV)

Statistical Analysis

The student t-test was used when control and test samples were analyzed. For determination of differences for multiple groups with varying lipid-drug concentrations, analysis of variance (ANOVA) was used. A p-value of less than 0.05 is considered statistically significant.

Results

Characterization of Atazanavir and Darunavir and their Ability to Form Lipid Nanoparticles In addition to lipophilicity, the degree of drug ionization at different pH could play a role in the ability of a drug to associate or bind to lipids. A number of predictive tools are available to estimate drug lipophilicity as a log value of the octanol-water partition coefficient (Log P) at neutral pH, typically expressed as XLog P. However, XLog P for ATV and DRV does not address the effects of varying pH. Therefore, we evaluated these values for ATV and DRV at pH 3, 5, and 7.4, and expressed them as Log D (octanol-buffer distribution coefficient) estimates. As shown in Table 1, while ATV and DRV have similar Log D values at pH 3-3.40 versus 2.98—only ATV, but not DRV, exhibited a pH-dependent Log D value. Log D for ATV increased with increasing pH with a value of 4.66 at pH 5, and 5.77 at pH 7.4. For DRV, Log D values for pH 5 and 7.4 were 2.80 and 2.84, respectively; no significant pH-dependent change in Log D was detectable. In comparison, the predicted XLogP3-AA values for ATV and DRV were 5.6 and 2.9, respectively, consistent with the observed Log D value for pH 7.4 stated above. Collectively, these data indicate that To determine whether there is a difference in the degree and manner in which the two hydrophobic drugs ATV and DRV incorporate into lipids, each compound was dissolved together with lipids in organic solvent composed of chloroform. After solvent removal and hydration in buffer, followed by particle size reduction, drug incorporation efficiency, particle size, and particle-size stability in varying concentrations were assessed. To keep lipid composition constant, we used lipids composed of DSPC and DSPE-mPEG2000 (8:2, mol/mol). This composition has been shown to be biocompatible and proven effective for anti-HV drug incorporation and cell uptake. We found that in the absence of lipids in the mixture, both ATV and DRV formed precipitates, and failed to form drug suspension. When ATV and DRV were mixed with lipids, no drug precipitation was observed, which allowed for determining drug incorporation into lipid nanoparticles. As shown in Table 2, we found that in all lipid-to-drug molar ratios (5:1, 8:1, and 20:1) tested, both ATV and DRV almost completely incorporated into lipid-drug nanoparticles. ATV incorporation efficiency was nearly 100% (range 96.2-97.4%) regardless of the lipid-to-drug molar ratio, while DRV incorporation efficiency appeared to decline with increasing drug density. DRV exhibited 8.5-6.3% lower incorporation efficiency at lipid-to-drug molar ratio 5:1 and 8:1, compared to that at lipid-to-drug molar ratio 20:1 (96.6% at 20:1, 94.4% at 8:1, and 88.1% at 5:1 lipid-to-drug molar ratio).

TABLE 2

Effect of the lipid-to-drug ratio on the degree of drug incorporation into lipid-drug nanoparticles and the particle size

| Lipid-drug nanoparticles[a] | lipid:drug (mol/mol) | Incorporation efficiency (%)[b] | Particle size[c] (nm) |
|---|---|---|---|
| Control (no drug) | 1:0 | — | 35.4 ± 4.4 |
| Atazanavir (ATV) | 20:1 | 97.4 ± 1.8 | 34.6 ± 3.1 |
|  | 8:1 | 96.2 ± 3.8 | 56.3 ± 4.1 |
|  | 5:1 | 96.5 ± 2.6 | 68.2 ± 7.1 |
| Darunavir (DRV) | 20:1 | 96.6 ± 4.8 | 35.6 ± 3.7 |
|  | 8:1 | 94.4 ± 2.8 | 35.6 ± 3.9 |
|  | 5:1 | 88.1 ± 3.8 | 33.6 ± 3.1 |

[a]Lipid-drug nanoparticles containing ATV or DRV with different lipid-to-drug molar ratios were prepared as described in Materials and Methods.
[b]Drug incorporation efficiency was determined based on % of drug bound to particles after removal of free, unincorporated drugs; data were expressed as mean ± SD of 4 replicates.
[c]Lipid-drug particle diameters were determined using PCS and the data were expressed as mean ± SD of 4 replicates.

We next determined the impact of varying lipid-to-drug molar ratios on the size (in diameter) of these lipid-drug nanoparticles. As shown in Table 2, the size of DRV-lipid nanoparticles (DRV-LNPs) did not change significantly with increasing lipid-to-drug molar ratio. The size of all the DRV-LNPs was approximately 33.6-35.6 nm, and this value was very similar to that of control lipid nanoparticles without drug (d~35.4±4.4 nm) (p>0.05). In contrast, the diameter of ATV-LNPs increased from 34.6±3.1 nm to 68.2±7.1 nm with increasing drug density (or decreasing lipid-to-drug ratio) (p<0.01; Table 2).

Taken together, these data indicate that ATV, but not DRV, exhibited pH-dependent hydrophobicity. While both ATV and DRV can incorporate almost completely into lipid nanoparticles composed of DSPC and DSPE-mPEG2000, incorporation efficiency declined with increasing drug density only for DRV, but not for ATV. Based on these data, we fixed the lipid-to-drug molar ratio at 8:1 for ATV and DRV to assess in subsequent studies how both of these drugs at different concentrations affected membrane fluidity and stability.

Figure 2:
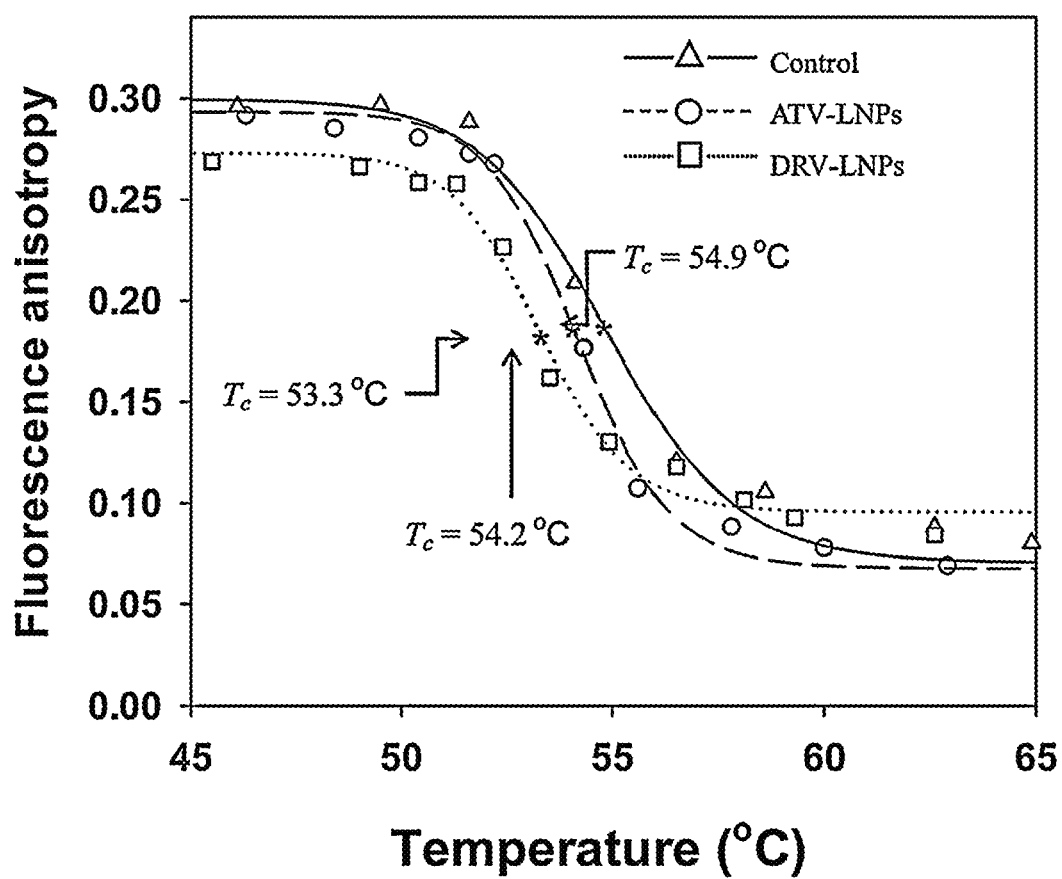
FIG. 2 graphically illustrates the effect of atazanavir (ATV) and darunavir (DRV) on lipid phase transition behavior. The influence of anti-HIV drugs atazanavir (ATV: ○) or darunavir (DRV: □) on lipid phase transition behavior was monitored by fluorescence anisotropy using the membrane polarity probe DPH. DPH anisotropy data were plotted against temperature (° C.). The lipid mixture without drug was also evaluated as a control (Δ). The data were fitted with a nonlinear regression model as described in Materials and Methods. The mid-point representing the phase transition temperature ($T_C$) for each lipid-drug composition and control was estimated. The estimated $T_C$ for control, ATV, and DRV lipid mixture was 54.9, 54.2, and 53.3° C., respectively.

Effects of Atazanavir and Darunavir on Membrane Fluidity: A Measurement of Lipid-Drug Interactions To characterize the interaction between drug and lipid, and drug effects on membrane fluidity, we used DPH as a fluorescence polarization probe. As a planar and hydrophobic fluorescent molecule, DPH inserted within the hydrophobic domain of the phospholipid bilayer is sensitive to changes in phase behavior, which are denoted by a change in the degree of DPH polarization and fluorescence intensity. DPH has been used successfully in several reports to study the order of membrane bilayers with fluorescence anisotropy. If a drug was bound and incorporated within lipids, a change in lipid membrane disorder induced by the drug should be detected. Therefore, we monitored fluorescence anisotropy of DPH in DSPC and DSPE-mPEG2000 lipid membrane with and without drug as a function of temperature. FIG. 2 shows, with increasing temperature, the fluorescence anisotropy for control lipid nanoparticles and lipid nanoparticles with ATV or DRV (at an 8:1 lipid-to-drug molar ratio). The mid-point of phase transition temperature ($T_C$) is also depicted.

As shown in FIG. 2, the incorporation of DRV into lipid bilayers decreased the polarization of DPH in lipid nanoparticles compared to that of drug-free lipid control. In contrast, incorporation of ATV exhibited less influence on the membrane order, as the fluorescence anisotropy values were similar to those of the lipid control. However, both ATV and DRV reduced the phase transition temperature to different degrees. With a fixed lipid-to-drug molar ratio of 8:1, DRV reduced the $T_C$ by 1.6° C., while ATV reduced $T_C$ only 0.7° C. ($T_C$=54.9, 54.2, 53.3° C. for control LNPs, ATV-LNPs, and DRV-LNPs, respectively; FIG. 2). The 54.9° C. $T_C$ value of control LNPs without drug was similar to 55° C. $T_C$ reported for DSPC. Collectively, these data indicate that both ATV and DRV can bind and incorporate into the lipid bilayer, altering the membrane fluidity and reducing the phase transition temperature.

Stability of Atazanavir and Darunavir Binding with Lipid and Concentration-Dependent Effects on Lipid-Drug Nanoparticles Although ATV and DRV bind to lipid and influence lipid structural behaviors, the stability of this binding interaction was important in developing a stable lipid-drug nanoparticle formulation. To address this question, we first tested particle-size stability under varying concentrations before determining the time-dependent drug release profile.

Our initial data indicated that ATV can bind stably into the lipid bilayer, while DRV binding was somewhat unstable. If drug molecules cannot bind stably with lipids, insoluble drug molecules could cause particle aggregation, dissociate from lipid as drug precipitates, or reorganize into smaller particles such as mixed micelles or micelles. After formation of ATV-LNPs and DRV-LNPs, we did not detect any drug precipitate, which was not typically observed with both ATV and DRV free drug in physiological buffer under identical conditions. As formation of mixed micelle or micelle structures are concentration-dependent and become apparent in low lipid-drug concentrations, lipid nanoparticles containing ATV or DRV along with control nanoparticles (without drugs) were diluted successively and a change in their diameters was monitored by PCS. The initial lipid concentrations were identical (200 mM) for the preparations, and they were diluted to a range of concentrations between 0.01-10 mM. As shown in Table 3, dilution of lipid-drug nanoparticles did not have a significant effect on the hydrodynamic diameter of ATV-LNPs. However, for DRV-LNPs, particle diameters appeared to get progressively smaller with decreasing lipid-drug concentrations (Table 3). When the concentration of DRV-LNPs was lower than 1 mM, the particle diameter declined to 8.9-14.3 nm from an initial 33.9±3.8 nm (p<0.01). The smaller diameters of these particles are in the range of mixed micelles and micelles. In contrast, the diameter of ATV-LNPs was not altered by dilution. As expected, dilution had no effect on the diameter of the control lipid nanoparticles (liposomes) without drugs (Table 3).

TABLE 3

Effect of concentration on apparent size of lipid-drug nanoparticles[a]

| Lipid concentration (mM) | Particle size (nm)[b] | | |
|---|---|---|---|
|  | Control | ATV-LNPs | DRV-LNPs |
| 10 | 36.2 ± 7.4 | 46.3 ± 5.7 | 33.9 ± 3.8 |
| 5 | 36.3 ± 6.7 | 53.6 ± 5.2 | 38.6 ± 5.1 |
| 1 | 34.0 ± 4.5 | 49.6 ± 3.6 | 13.8 ± 2.6 |
| 0.25 | 32.1 ± 4.6 | 43.7 ± 3.2 | 14.3 ± 1.0 |
| 0.05 | 33.1 ± 4.5 | 37.2 ± 2.8 | 10.3 ± 1.3 |
| 0.01 | 32.4 ± 4.5 | 37.8 ± 2.7 | 8.9 ± 1.0 |

[a]Lipid-drug nanoparticles containing ATV or DRV with a fixed lipid-to-drug molar ratio (8:1) or control (without drug) were prepared as described in Materials and Methods.
[b]The apparent size of particles at indicated concentrations and dilution were measured by PCS and the particle diameters were expressed as mean ± SD of 4 replicates.

The concentration dependent effects on DRV-LNPs were further confirmed by preparing DRV-LNPs at different initial concentrations to determine drug incorporation efficiency. We found that drug incorporation efficiencies for DRV at 5 and 0.5 mM lipid were 95% and 58%, respectively, compared to 96% and 97%, respectively, for ATV.

Next, as a part of stability studies, we determined the time-course of drug release from ATV-LNPs and DRV-LNPs. These drug release studies were performed on 5, 25, and 200 mM lipid-drug preparations and evaluated the percentage of drug released after 24 h at pH 7.4. Over this time period, we did not find any appreciable fraction of drug release from ATV-LNPs (FIG. 3A). In contrast, for DRV-LNPs, nearly 100% of DRV was released in 5 and 25 mM dilutions, and 53% drug release was detected in the 200 mM preparation. Instability of DRV-LNPs was also apparent by 4 h, at which time 65.21%, 42.14%, and 29.99% of DRV was released from 5, 25, and 200 mM DRV-LNPs, respectively (FIG. 3B).

Taken together, these data indicate that while DRV and ATV are equally effective in their ability to incorporate into lipid nanoparticles, only ATV integration in the lipid bilayer produces a stable structure that is not susceptible to dilution or rapid drug release. DRV-LNPs are less stable and are subject to a concentration-dependent increase in drug release rate and particle size reduction. Therefore, for subsequent experiments, we used ATV-LNPs for pH-dependent drug release characterization, as well as for constructing combination drug particles for formulation scale up and preliminary primate studies.

pH-Dependent Release of Atazanavir from Lipid Nanoparticles

Figure 4:
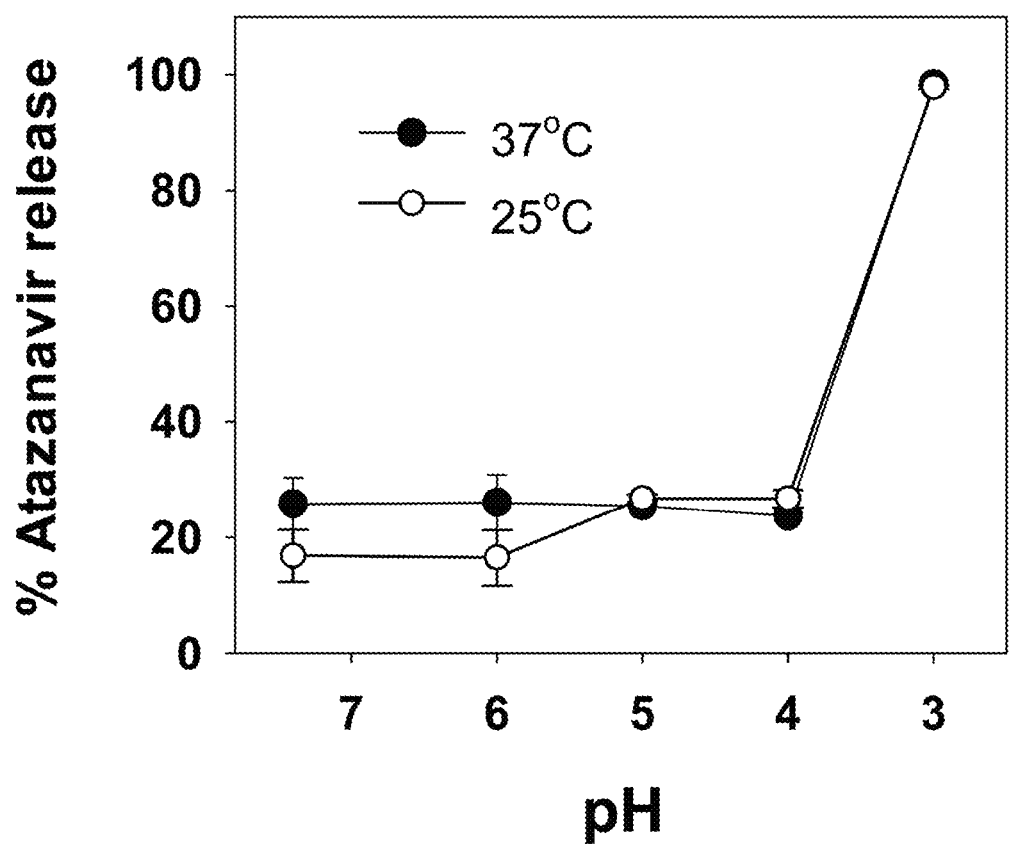
FIG. 4 graphically illustrates the pH-dependent atazanavir release from atazanavir lipid nanoparticles (ATV-LNPs). The percentage of total atazanavir in ATV-LNPs released after exposure to the indicated pH were measured at either 25° C. (○) and 37° C. (●). Data for each pH and temperature are expressed as mean±SD % total atazanavir release of triplicate samples.
Figure 5B:
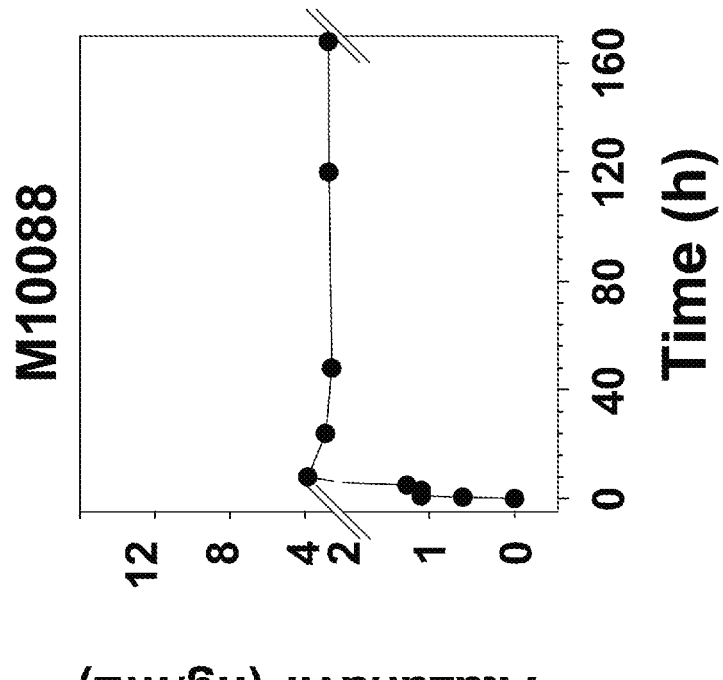
FIG. 5A-5F graphically illustrate the time-course of plasma drug concentrations in two primates administered with anti-HIV lipid nanoparticles containing three drugs, atazanavir (ATV), ritonavir (RTV) and tenofovir (TFV) in combination. Two primates, M11016 (FIGS. 5A, 5C, 5E) and M10088 (FIGS. 5B, 5D, 5F), were given anti-HIV lipid nanoparticles containing ATV, RTV, and TFV (25, 12.8, 15.3 mg/kg, respectively) subcutaneously. The plasma drug concentration at indicated time points was determined for ATV (FIGS. 5A, 5B), RTV (FIGS. 5C, 5D), and TFV (FIGS. 5E, 5F).
Figure 5A:
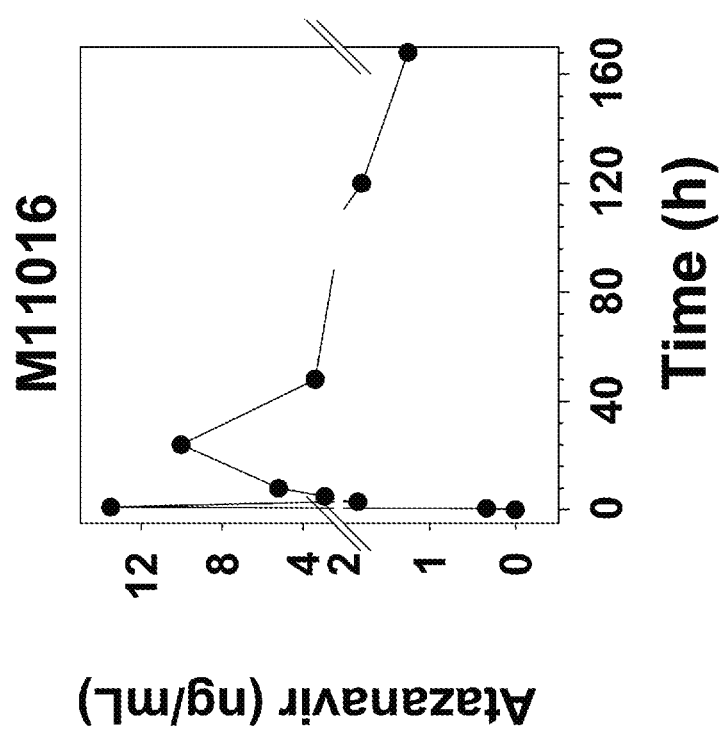
Figure 5D:
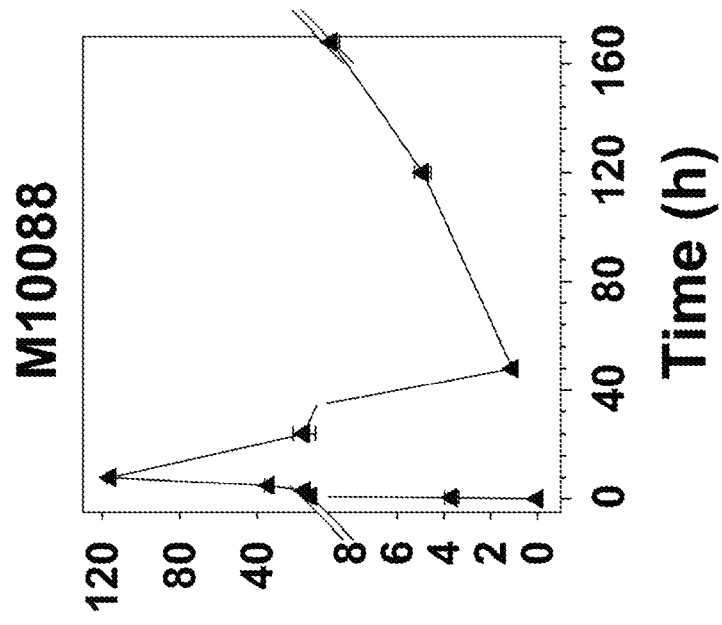
Figure 5C:
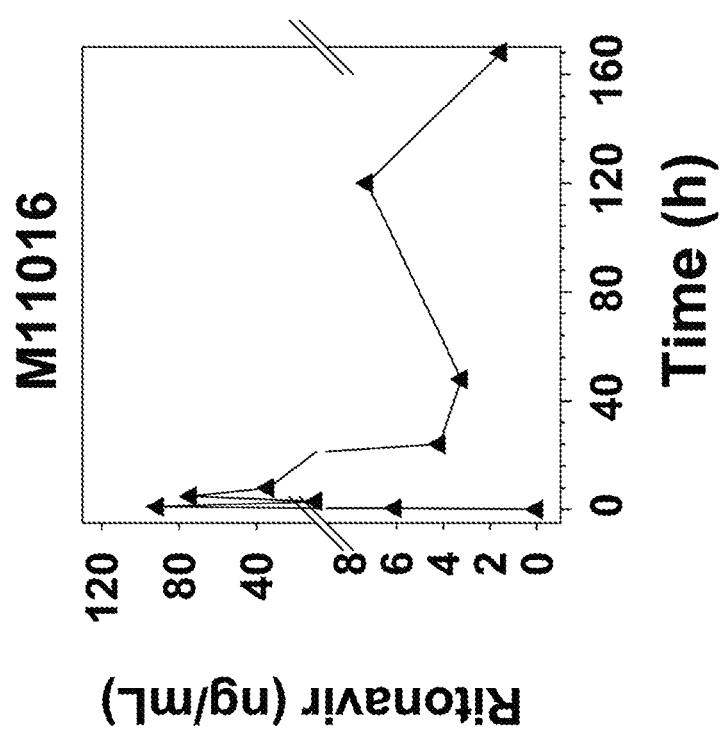
Figure 5F:
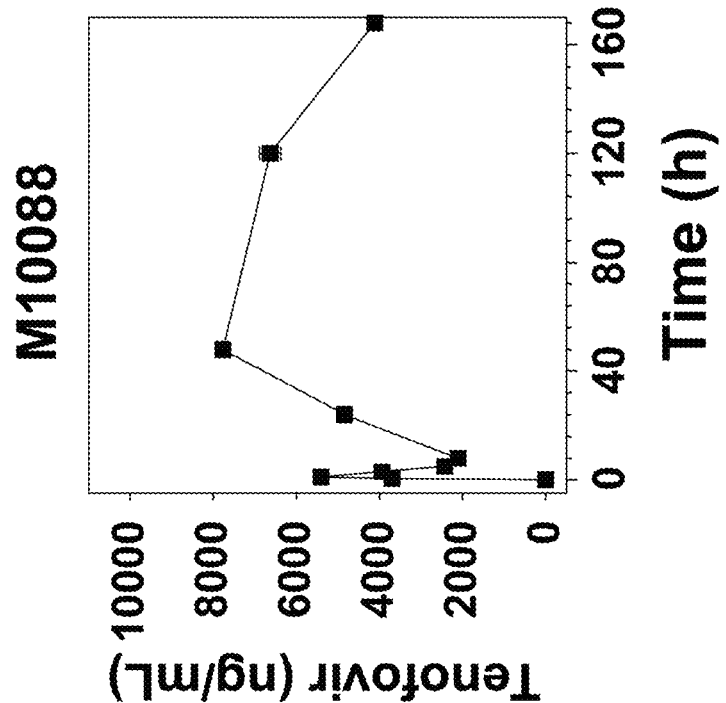
Figure 5E:
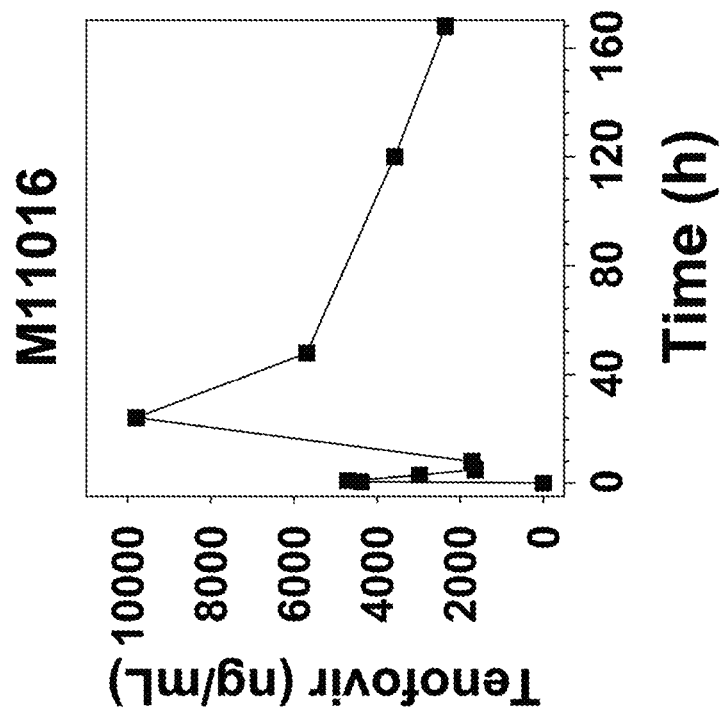

As ATV exhibits pH-dependent lipophilicity, we determined whether a change in pH may induce drug release from ATV-LNPs. To do so, we exposed ATV-LNPs to buffer at different pHs and measured the fraction of ATV released from the lipid-drug nanoparticles. As shown in FIG. 4, after exposing the ATV-LNPs to progressively lower pH at 37° C. for 24 h, about 21.3-26.2% of ATV molecules were released from ATV-LNPs under these conditions. When pH was dropped to 3, almost all ATV molecules were released within 24 h. This behavior was also very similar to pH-dependent ATV release at 25° C. (FIG. 4). Collectively, these data indicate that release of ATV from ATV-LNPs is dependent on pH and to some degree temperature.

Development and Scale Up Preparation of Anti-HIV Drug Combination Lipid Nanoparticles As the lipid drug interaction studies above indicated that ATV (not DRV)-lipid interactions produced stable ATV-LNPs, ATV was chosen to develop anti-HIV drug combination nanoparticles. Following the current clinical guidelines for optimal reduction of virus resistance potential, in addition ATV, this anti-HIV drug combination also includes RTV, a metabolic inhibitor/booster for ATV, plus TFV, a reverse transcriptase inhibitor. Tenofovir (TFV) was chosen for its proven potency as a reverse transcriptase inhibitor and because it is retained intracellularly as a phosphorylated active metabolite for sustained response. Therefore, we prepared three different preparations of laboratory scale (0.2 mL) lipid nanoparticles containing ATV, ATV+RTV, or ATV+RTV+TFV and evaluated their incorporation efficiencies and physical characteristics. As shown in Table 4, addition of RTV or RTV+TFV into ATV-lipid nanoparticles did not alter the ~100% ATV incorporation efficiency. We also found that under those conditions RTV incorporation efficiency was similarly almost 100% (Table 4). As a water soluble drug, TFV incorporation efficiency was about 2.4% and was reproducible from batch to batch. Including all three drugs in lipid nanoparticles did not have any impact on physical characteristics, as no significant change was detected in particle diameter (d=56-62 nm) (Table 4). In a preliminary experiment, we compared ATV versus ATV+RTV lipid nanoparticles in their ability to produce pH-dependent drug release. We found pH-dependent release of ATV and RTV was very similar to that of ATV-LNPs. Therefore, we prepared these anti-HIV drug combination lipid nanoparticles (ATV+RTV+TFV LNPs) in a larger volume for a preliminary primate pharmacokinetical study (described below). As shown in Table 4, the scaled-up preparation (~45 mL) produced under aseptic conditions also provided a particle size, pH, and osmolality comparable to that of the laboratory scale preparations (~0.2 mL). This preclinical scale provided almost complete incorporation of ATV and RTV and consistent TFV incorporation of around 6% in a reproducible manner. Therefore, these anti-HIV LNPs containing the ATV, RTV, and TFV (2:1:3 molar ratio) drug combination were used for primate studies without undergoing removal of the unbound (about 93.9% free) TFV in the preparation.

TABLE 4

Characterization of lipid nanoparticles containing anti-HIV drugs prepared at a pilot or preclinical scale for primate studies

| Drug formulated in lipid nanoparticles[a] | Incorporation efficiency (%)[b] | | | Particle size (nm)[c] | pH | Osmolality (mmol/Kg)[d] |
| --- | --- | --- | --- | --- | --- | --- |
| | Atazanavir (ATV) | Ritonavir (RTV) | Tenofovir (TFV) | | | |
| Laboratory scale | | | | | | |
| ATV | 100.5 ± 8.2 | — | — | 56.3 ± 4.1 | 7.2 ± 0.3 | 327 ± 26.1 |
| ATV + RTV | 93.5 ± 6.6 | 95.2 ± 5.7 | — | 60.2 ± 1.0 | 7.3 ± 0.2 | 235.3 ± 9.1 |
| ATV + RTV + TFV (0.2 mL scale) | 104.2 ± 3.2 | 103.1 ± 5.3 | 2.4 ± 0.1 | 62.4 ± 3.7 | 7.4 ± 0.2 | 278.7 ± 6.4 |
| Preclinical scale | | | | | | |
| ATV + RTV + TFV (45 mL scale) | 85.5 ± 8.2 | 85.1 ± 7.1 | 6.1 ± 0.8 | 63.6 ± 1.1 | 7.4 ± 0.3 | 213.5 ± 0.7 |

[a]Drug formulated in lipid nanoparticles was prepared as described in Materials and Methods. For both pilot (0.2 mL) and preclinical (45 mL) scales, the three-drug combination ATV + RTV + TFV (2:1:3 (mol/mol)) was used as a comparison. In pilot scale, lipid nanoparticles containing ATV or ATV + RTV were also prepared at the lipid-to-drug ratio 8:1 (mol/mol).
[b]Incorporation efficiency was determined as described in Table 2.
[c]Particle diameters of lipid-drug nanoparticles were measured with PCS and expressed as mean ± SD.
[d]Osmolality of lipid-drug nanoparticles were monitored as described in Materials and Methods, and expressed as mean ± SD.

Plasma Time Course of Anti-HIV Drug Combination Lipid Nanoparticles in Primates

To evaluate the plasma time course of ATV, RTV, and TFV, two primates were used in a preliminary study. They were given a subcutaneous single dose of anti-HIV drug combination lipid nanoparticles containing 25 mg/kg ATV, 12.8 mg/kg RTV, and 15.3 mg/kg TFV. Plasma drug concentrations were monitored for 7 days (see FIG. 5A-5F). As shown in FIG. 5A-5F, in both macaques receiving anti-HIV LNPs, plasma drug concentrations persisted at detectable levels over the 7 days (168 h). Two prominent peaks in the plasma TFV concentration time-course profile were detected for both animals. The first peak of TFV appeared to subside at 8 h (FIGS. 5E and 5F), followed by a more prominent and sustained plasma TFV level. Sustained plasma TFV levels was unexpected as this anti-HIV formulation provided only 6.1% of lipid-bound TFV (93.9% in free soluble form). For RTV and ATV, this reflection point appeared to be less prominent and more variable (FIGS. 5A-5D). However, both ATV and RTV were clearly detectable in the plasma at 7 days after a single subcutaneous dose of anti-HIV LNPs composed of the three-drug combination.

We further analyzed the time-course of plasma drug concentration by calculating the plasma drug concentration AUC of each drug to determine plasma drug exposure over time. Our experience with primate subcutaneous dosing of protease inhibitors such as indinavir, LPV, and RTV in solution or suspension, as well as the plasma half-life reported in respective product labels, has indicated that plasma drug concentrations are expected to fall below detection limits by 4-5 h and TFV in solution falls below detection limits by 8 h. Therefore, we analyzed the AUC for early (0-8 h) and late (8-168 h) time courses. While there were some variations between the two animals, it was clear that early (0-8 h) phase AUC was less than 20% of total AUC (0-168 h) for all three drugs, including TFV, after subcutaneous dosing with anti-HIV lipid nanoparticles. The low 2.6% early $AUC_{0-8h}$ fraction for TFV was unexpected as the anti-HIV LNPs contained 93.9% (only 6.1%-associated with LNPs) free TFV. In fact, a majority of the TFV exposure (AUC fraction) was found in the later phase $AUC_{8-168\ h}$. Regardless, these data indicated that anti-HIV LNPs provided sustained plasma drug levels for the three drugs, ATV, RTV, and TFV, in primates and the early phase drug exposure in the plasma was less than 20% of the total drug exposure that lasted over 168 h or 7 days after a single subcutaneous dose.

Discussion

While clinical use of a number of oral anti-HIV drug combinations, including protease inhibitors such as indinavir, LPV, RTV, ATV, and DRV, have been successful in reducing plasma HIV to below detection limits, most oral drug therapies require at least once or more daily dosings. Single or multiple daily dosing of multiple liquid and solid oral formulations often face compliance challenges, particularly in the substance abuse and at-risk populations where the HIV transmission rate is high. Therefore, the healthcare community has placed urgency in developing a once-a-week anti-HIV combination drug regimen that overcomes daily dosing requirements of an oral dosage form, particularly for patients with compliance (e.g., drug abuse population) or practicality (inability to swallow or gastrointestinal discomfort) issues. Taking advantage of the hydrophobicity of ATV and DRV, and their ability to bind and interact with lipids, we have developed lipid nanoparticles containing one (ATZ) of these two drugs and characterized the stability of the lipid-drug interactions. We found that ATV, but not DRV, associated stably with lipids, enabling development of an anti-HIV drug combination lipid nanoparticle composed of ATV, RTV, and TFV, a hydrophilic reverse transcriptase inhibitor. This combination of drugs was chosen considering current clinical HAART recommendations, giving it greater clinical potential. We produced these combination nanoparticles using a simple scale up process that generated reproducible characteristics on a preclinical scale suitable for study in primates.

Previous studies with the HIV protease inhibitor indinavir demonstrated that this compound associates completely with lipids. Additional optimization studies indicated that phospatidycholine lipid with $C_{18}$ fatty acyl chains, (DSPC and a pegylated lipid, $DSPE-mPEG_{2000}$) provided stable drug incorporation and drug accumulation in lymphoid tissues when administered subcutaneously in primates. These reports also showed that the complete drug association in lipid-drug nanoparticles facilitated the ability of drug to localize in lymph nodes throughout the body and produce sustained drug levels in plasma. In this report, we used the same lipid composition to demonstrate that two potent HIV protease inhibitors, ATV and DRV, both of which exhibit a high degree of lipophilicity at neutral pH were able to bind to lipids at a high density (up to 1 drug molecule for every 5 lipid molecules). We were able to produce lipid nanoparticles with diameters of 33.6-68.2 nm that exhibited nearly 100% ATV or DRV incorporation efficiency (Table 2). The lipid insertion of ATV and DRV was apparent in the ability of each drug to lower the lipid phase transition temperature and, to a varying degree, the order of lipid molecular organization within the lipid-drug nanoparticle structure. The impact of drug on lipid packing was detectable as a reduction in anisotropic behaviors of the membrane polarization probe DPH (FIG. 2). While both ATV and DRV appeared to influence the order state of lipid membrane, DRV appeared to have a higher impact than ATV, detected as a greater suppression in lipid phase transition temperature (FIG. 2). In addition, concentration-dependent studies demonstrated that only the apparent size (diameter) of DRV-LNPs, not ATV-LNPs, was affected by dilution. Only DRV-LNPs particle size decreases significantly to the size range of mixed micelles. These data suggest that DRV, but not ATV, induced LNPs to adopt micelle-like behavior upon dilution (Table 3). In contrast, the diameter of ATV-incorporated lipid nanoparticles did not change significantly when lipid concentrations were lowered, indicating that they form stable lipid-drug nanoparticles. This concentration-dependent size behavior was consistent with the much lower drug release rate observed with ATV-LNPs compared to that of DRV-LNPs, and the release rate for ATV-LNPs also appeared to be concentration-independent (FIGS. 3A and 3B).

While the exact mechanism or degree of DRV and ATV insertion into lipid membrane is not clear, it was apparent from the pH-dependent distribution coefficient data that only ATV exhibits a pH-dependent change in lipophilicity. The Log D, a measurement of pH-specific lipophilicity, for ATV increased from 3.40 to 5.77 when the pH was raised from 3 to 7.4, while the Log D of DRV remained comparably unchanged (2.80-2.98) for the same pH range (Table 1). The higher Log P value of ATV, compared to DRV, may have contributed, in part, to a more stable association of ATV-LNPs (Tables 2-3 and FIGS. 3A and 3B). In addition, the pH-dependent lipophilicity of ATV may be related to the ability of ATV to dissociate pH-dependently from lipid-drug nanoparticles between pH 3-7.4 (FIG. 4). Furthermore, pKa of the solute may influence the degree and extent of pH-dependent drug release from lipid-drug nanoparticles. As a chemically stable compound under acidic conditions, when pH is lower than pKa (acidic), the chemical compound will be protonated, and the solubility will be increased. Surroundings at pH 3 are lower than the pKa 4.42 of ATV (acidic, Table 1), which is the reason why at pH 3, about 98.1% of ATV was released from ATV-LNPs. For DRV, pH 3-7.4 are all higher than its pKa 2.39 (acidic, Table 1). In this condition, DRV will be deprotonated, making it more hydrophobic and unable to undergo pH-dependent release. Thus, ATV integrated into lipid nanoparticles can be internalized by cells in lymph nodes and lymphoid tissues and released subsequently in the endosome and lysosome where pH is lowered to 5.5 and 4, respectively. pH-sensitive drug association and dissociation from nanoparticles will be useful to improve intracellular delivery of free drug molecules to lymph nodes and lymphoid tissues. Within these intracellular acidic organelles, the free or unbound drug could be made available to potentiate anti-protease activities and anti-HIV effects. These and other possibilities need further investigation, however, such studies are beyond the scope of this report.

The stability of ATV binding and insertion into lipid membranes and a detailed understanding of lipid-drug interactions, have enabled us to develop a formulation that contains two other clinically-used anti-HIV drugs: RTV and TFV. RTV is a metabolic and exporter inhibitor that is often used in combination with other protease inhibitors such as ATV to decrease their rate of clearance. With nearly complete and reproducible incorporation of ATV and RTV into lipid nanoparticles (Table 4), the scale up process is greatly simplified without the need of removing free protease inhibitors. Thus, a wasteful and potentially cost-prohibitive purification process can be avoided. For example, the requirement for removal of free human growth hormone (hGH) in polymeric particles was proven to be cost-prohibitive and cited as a key reason for discontinuing production of the sustained release hGH after receiving regulatory approval for marketing in the US. The near-complete incorporation of ATV and RTV into lipids described in this report could be considered an important characteristic of these lipid-drug nanoparticles that allowed for sustained drug levels in primates beyond that attainable by oral or subcutaneous dosing of soluble and suspension formulations.

Current clinical guidelines recommend prescribing at least two drugs in combination to suppress viral resistance, or drug combinations that inhibit two HIV targets, such as protease inhibitors and reverse transcriptase. Therefore, we chose a proven reverse transcriptase inhibitor, TFV, which is phosphorylated intracellularly and subsequently retained for an extended time, for incorporation into lipid-drug nanoparticles containing ATV and RTV. However, due to the high water solubility (low lipophilicity), we found a low, but consistent and reproducible degree of TFV incorporation around 6%. We therefore proceeded to primate studies with these three drugs—ATV, RTV, and TFV—in the lipid-drug nanoparticles that contained 93.9% TFV in "free," soluble form. Administration of soluble ATV, RTV, or TFV, have shown that plasma drug levels in primates typically fall below detection levels within 8 h and no drug is detectable in plasma at 24 h. When the same three drugs were formulated together into lipid-drug nanoparticles, we found that all three drugs were still detectable in the plasma of two primates after 7 days. While it was anticipated that ATV and RTV would provide sustained but low levels, to our surprise, water soluble TFV, with only 6.1% bound to particles (93.9% free form), also exhibited a high degree of plasma drug exposure beyond that available during the free-drug release period. One would expect that the AUC ratio of TFV for the early time points (0-8 h) should be higher than later time points because 93.9% of TFV exists as free drug. Free drug would presumably be absorbed directly into the blood from the subcutaneous space, or permeate easily through the lymph nodes and appear in the blood rapidly. Thus, one would anticipate a high plasma drug concentration and a high AUC ratio at early time points (0-8 h). However, we found that only 2.6% of drug exposure ($AUC_{0-8h}$) was detectable for TFV in plasma from 0-8 h, while 97.4% of drug exposure was detectable from 8-168 h (Table 5). These data suggest that TFV (combined with ATV and RTV in the formulation) may interact with the anti-HIV LNPs with a yet-to-be defined mechanism, leading to the extended TFV persistence in plasma. While the exact mechanisms of the observed interaction and plasma TFV time course extension warrant further investigation, the current data point to a possibility of once-a-week dosing of triple ATV+RTV+TFV LNPs to provide sufficient antiviral levels in plasma.

TABLE 5

Analysis of early (0-8 h) versus late (8-168 h) plasma drug exposure for primates subcutaneously administered with anti-HIV nanoparticles containing three drugs with different incorporation efficiencies

| Drug | Drug incorporation (% total) | AUC (ng · h/mL)[a] | | | $AUC_{fraction}$ (% total)[b] | |
|---|---|---|---|---|---|---|
| | | 0-8 h | 8-168 h | 0-168 h | 0-8 h | 8-168 h |
| Atazanavir (ATV) | 85.5 ± 8.2 | 24.3 | 491.1 | 515.4 | 4.7% | 95.3% |
| Ritonavir (RTV) | 85.1 ± 7.1 | 339.1 | 1,390.3 | 1,729.4 | 19.6% | 80.4% |
| Tenofovir (TFV) | 6.1 ± 0.8 | 23,214.8 | 868,653.6 | 891,868.3 | 2.6% | 97.4% |

[a]The average AUC for the two primates (M11016 and M10088) at indicated time-spans (0-8 h, 8-168 h, and 0-168 h) in units of ng · h/mL.
[b]AUC fraction for early (0-8 h) and late (8-168 h) are compared with 0-168 h total plasma exposure. The data were expressed as % AUC for each drug.

If needed, plasma drug levels could be increased with either increasing dose, or increasing frequency of the same dose. Detailed pharmacokinetic studies with more animals are being planned and will be needed to elucidate the predictive pharmacokinetic parameters for defining the dose and frequency necessary to provide an optimal antiviral plasma concentration. Such studies, however, are beyond the scope of this report.

In summary, we have demonstrated that both protease inhibitors ATV and DRV can incorporate almost completely into lipid nanoparticles. However, only ATV, but not DRV, associated stably with lipids and enabled development of anti-HIV drug combination lipid nanoparticles. The triple anti-HIV LNPs containing ATV, RTV, and TFV could be prepared aseptically and scaled to produce consistent particle size, pH, and osmolality characteristics suitable for subcutaneous administration in primates. These anti-HIV drug combination lipid nanoparticles provided sustained plasma drug levels of all three drugs for more than 7 days, even for the hydrophilic drug TFV. Based on the preliminary primate plasma concentration-time data, once-a-week dosing of anti-HIV nanoparticles containing ATV, RTV, and TFV may be feasible.

Example 2

This example describes the design and characterization of additional multi-drug lipid nanoparticles provide long-acting three-drug combination anti-HIV nanoparticles enhance drug exposure in primate plasma and cells within lymph nodes and blood Insufficient HIV drug levels in lymph nodes have been linked to viral persistence. To overcome lymphatic drug insufficiency, we developed and evaluated in primates a lipid-drug nanoparticle containing lopinavir, ritonavir, and tenofovir. These nanoparticles produced over 50-fold higher intracellular lopinavir, ritonavir and tenofovir concentrations in lymph nodes compared to free drug. Plasma and intracellular drug levels in blood were enhanced and sustained for 7 days after a single subcutaneous dose, exceeding that achievable with current oral therapy.

Combined antiretroviral therapy (cART) can clear HIV from the blood; however, residual virus remains in lymph nodes. Oral cART produces lower drug concentrations in lymphoid tissues than in plasma, which is linked to persistent virus in lymph nodes and virus rebound upon therapy cessation. Drug nanoparticles have the potential to overcome lymphatic drug insufficiency. We previously developed and demonstrated in primates a lipid nanoparticle (LNP) containing indinavir (IDV) that enhanced drug levels in all analyzed lymph nodes. Also, IDV in LNPs enhanced intracellular drug concentrations in peripheral blood mononuclear cells (PBMCs), prolonged plasma residence time, reversed CD4$^+$ T-cell decline, and suppressed viral RNA in both plasma and lymph nodes. Building on findings with IDV-LNPs, we have developed an anti-HIV LNP containing two protease inhibitors, lopinavir (LPV) and ritonavir (RTV), and a reverse transcriptase inhibitor, tenofovir (TFV), for simultaneous, triple drug delivery to HIV host cells in blood and lymph. LPV and RTV were chosen for their stability and strong hydrophobic interactions with LNPs. Ritonavir enhances the efficacy of LPV through metabolic and drug transporter interactions. Inclusion of TFV provides a second target of antiviral action to further suppress drug resistance potential, and intracellular retention of phosphorylated TFV prolongs antiviral activity.

We evaluated the characteristics of optimized anti-HIV LNPs for primate studies. The aseptically prepared anti-HIV LNPs exhibited 94, 91 and 12% LPV, RTV and TFV incorporation, respectively, with a mean diameter of 52 nm. The well-defined unbound drug fractions were included for in-vivo studies. Antiviral potency against HIV-1, evaluated at a fixed LPV:RTV:TFV 1:1:0.5 mole ratio, revealed at least a three-fold increase in potency with anti-HIV LNP compared to the drugs in soluble form (LPV, RTV, and TFV $EC_{50}$ 30±0.8, 30±0.8, 15±0.1 nmol/l in LNP form, vs. 98±0.3, 98±0.3, 49±0.2 nmol/l in free form).

Primates dosed subcutaneously with LPV, RTV, and TFV (25.0, 14.3, and 17.1 mg/kg) in anti-HIV LNP form exhibited elevated plasma concentrations of LPV and RTV over 7 days (168 h). In contrast, plasma drug levels after administration of free drug in combination subsided to near or below detection limited by 24 h. The increase in total drug exposure [area under the curve (AUC)] provided by the LNP formulation for LPV, RTV, and TFV was 18, 14, and 7-fold, respectively (paired t test P=<0.05, 0.07, and 0.173) (Table 6). The AUCs for early (0-8 h) versus late drug exposure (8-168 h) were also analyzed. Primates treated with free drug exhibited 92% of total TFV exposure within the first 8 h, whereas those treated with anti-HIV LNPs exhibited only 9.1% in the first 8 h, with the remaining fraction at 8-168 h (Table 6).

Intracellular drug accumulation is pivotal for antiviral effects. Sustained LPV, RTV and TFV in PBMCs were detected for over 7 days in primates treated with anti-HIV LNPs, whereas those on free drug fell near or below the detection limit by 48 h (Table 6). The ratio of anti-HIV LNP to free drug (LNP/free ratio) was used to compare PBMC drug concentrations between the two test groups. This ratio was greater than 1 at all time points beyond 5 h, and greater than 20 at later time points (Table 6). For TFV, with only 12% LNP association, the LNP/free ratio in blood PBMCs was less than 1 at early time points; by 8 h, however, this value increased to over 50. Anti-HIV LNPs also enhanced intracellular drug concentrations in mononuclear cells of lymph nodes (LNMCs). LNMCs isolated from inguinal lymph nodes at 24 h revealed that no LPV and only low levels of RTV were detectable in animals treated with the free drug combination, whereas those treated with anti-HIV LNPs exhibited over 50-fold higher intracellular concentration (Table 6). For TFV, with limited LNP association, the LNP/free ratio was lower and recorded at 0.7; however, the differences between the two groups of macaques were not statistically significant (P=1.0).

TABLE 6

The effect of anti-HIV lipid nanoparticle[a] on intracellular levels of lopinavir, ritonavir, and tenofovir in peripheral blood mononuclear cells and inguinal lymph nodes, as well as overall drug exposure in plasma[b].

| | Lopinavir | | | Ritonavir | | | Tenofovir (TFV) | | |
|---|---|---|---|---|---|---|---|---|---|
| Time (h) | Free drug | LNP | LNP/free ratio[c] | Free drug | LNP | LNP/free ratio[c] | Free drug | LNP | LNP/free ratio[c] |
| Intracellular drug concentration of mononuclear cells in blood (ng/10$^6$ mononuclear cells)[d] | | | | | | | | | |
| 0 | 0.00 ± 0.00 | 0.00 ± 0.00 | 1.0 | 0.00 ± 0.00 | 0.00 ± 0.00 | 1.0 | 0.00 ± 0.00 | 0.00 ± 0.00 | 1.0 |
| 0.5 | 0.67 ± 0.31 | 0.28 ± 0.24 | 0.4 | 0.96 ± 1.67 | 0.41 ± 0.58 | 0.4 | 5.01 ± 5.12 | 1.29 ± 1.83 | 0.3 |
| 1 | 1.93 ± 1.18 | 1.85 ± 1.11 | 1.0 | 2.92 ± 2.62 | 2.57 ± 1.04 | 0.9 | 3.55 ± 4.21 | 1.29 ± 0.93 | 0.4 |

TABLE 6-continued

The effect of anti-HIV lipid nanoparticle[a] on intracellular levels of
lopinavir, ritonavir, and tenofovir in peripheral blood mononuclear cells
and inguinal lymph nodes, as well as overall drug exposure in plasma[b].

Drug concentration

| | Lopinavir | | | Ritonavir | | | Tenofovir (TFV) | | |
|---|---|---|---|---|---|---|---|---|---|
| Time (h) | Free drug | LNP | LNP/free ratio[c] | Free drug | LNP | LNP/free ratio[c] | Free drug | LNP | LNP/free ratio[c] |
| 3 | 0.91 ± 0.53 | 2.39 ± 1.15 | 2.6 | 2.85 ± 1.50 | 3.05 ± 1.06 | 1.1 | 2.57 ± 2.62 | 1.19 ± 0.92 | 0.5 |
| 5 | 0.32 ± 0.28 | 2.59 ± 1.44 | 8.1 | 0.90 ± 0.60 | 2.20 ± 1.43 | 2.4 | 0.27 ± 0.21 | 1.24 ± 1.16 | 4.6 |
| 8 | 0.70 ± 0.86 | 4.23 ± 2.34 | 6.0 | 0.74 ± 0.99 | 4.57 ± 3.04 | 6.2 | 0.01 ± 0.01 | 0.59 ± 0.27 | 59.0 |
| 24 | 0.16 ± 0.28 | 3.26 ± 2.25 | 20.4 | 0.00 ± 0.00 | 4.09 ± 2.90 | >409.0 | 0.01 ± 0.01 | 0.70 ± 0.14 | 70.0 |
| 48[e] | 0.01 ± 0.01 | 0.03 ± 0.00 | 3.0 | 0.00 ± 0.00 | 0.00 ± 0.00 | 1.0 | 0.00 ± 0.00 | 2.27 ± 0 | >227.0 |
| 120[e] | NA | 0.02 ± 0.00 | NA | NA | 1.37 ± 0.00 | NA | NA | 0.64 ± 0 | NA |
| 168 | 0.00 ± 0.00 | 0.08 ± 0.10 | >8.0 | 0.00 ± 0.00 | 1.32 ± 1.14 | >132.0 | 0.00 ± 0.00 | 0.25 ± 0.25 | >25.0 |
| Intracellular drug concentrations in mononuclear cells of inguinal nodes (ng/10⁶ mononuclear cells)[e] | | | | | | | | | |
| 24 | 0.00 ± 0.00 | 4.85 ± 0.04 | >485.0 | 0.13 ± 0.13 | 6.57 ± 0.08 | 50.5 | 1.02 ± 0.13 | 0.76 ± 0.09 | 0.7 |
| Plasma drug exposure analysis (AUC in μg*h/ml)[f] | | | | | | | | | |
| 0-168 | 3.83 ± 4.04 | 69.6 ± 10.7 | 18.2 | 1.39 ± 1.18 | 19.4 ± 12.2 | 14.0 | 56.6 ± 17.04 | 395.0 ± 344.5 | 7.0 |
| 0-8 (%) | 19.6 | 9.9 | | 30.2 | 11.3 | | 91.8 | 9.1 | |
| 8-168 (%) | 80.4 | 90.1 | | 69.8 | 88.7 | | 8.2 | 90.9 | |

LNP, lipid nanoparticle. NA, not available.
[a]Anti-HIV LNPs composed of 1,2-distearol-sn-glycero-3-phosphocholine (DSPC), N-(carbonyl-methoxypolyethyleneglycol-200)-1,2-distearoyl-sn-glycero-3-phosphoethanolamine, sodium salt (MPEG-2000-DSPE), lopinavir, ritonavir, and tenofovir (TFV) were prepared by thin film hydration method, as previously published. All drugs were dried with the lipid film, rehydrated in bicarbonate-buffered saline, and size-reduced by high-pressure homogenization under aseptic conditions to produce drug-lipid nanoparticles with a mean 52 nm diameter. Free drug suspension dosages were prepared in bicarbonate-buffered saline using biocompatible solvent and surfactant to suspend the highly hydrophobic drugs.
[b]Four primates (*Macaca nemestrina*) were administered anti-HIV LNPs and free drug in a cross-over study at a normalized dose of 25 mg/kg LPV, 14.3 mg/kg RTV, and 17.1 mg/kg tenofovir (TFV) subcutaneously. All experiments were done under an approved Institutional Animal Care and Use Committee (IACUC) protocol. Blood and lymph nodes were collected over 7 days at indicated time points and drug concentrations were determined with a validated liquid chromatography-tandem mass spectrometry (LC-MS/MS) published assay. Data are expressed as mean ± SD. Ratios for comparative analysis are shown in bold.
[c]LNP/free ratio is the mean anti-HIV LNP drug concentration divided by mean free drug concentration. In cases where the drug level was below detectable limits, the number was taken as '0.01' to calculate ratio.
[d]PBMCs were isolated from whole blood by density gradient method, and cell pellets of 2 million PBMCs each were analyzed. (n = 4/group; at 48 h and 120 h, n = 2/group).
[e]An inguinal lymph node was collected at 24 h (n = 2/group) and mononuclear cells were isolated by pressing tissue through a 200 μm cell strainer. Pellets of 2 million cells each were analyzed.
[f]Area under the curve (AUC) was calculated from plasma drug concentrations using the trapezoidal rule. The fractional percentage of total AUC in the early phase (0-8 h) and late phase (8-168 h) was calculated from the mean of the total AUC and the mean AUC in the indicated time range. Values are expressed as a percentage of the total AUC (n = 4/group).

While toxicity of anti-HIV LNPs needs further investigation, complete blood count, serum chemistry panel, C-reactive protein, and complement levels revealed no treatment impact. No anti-HIV LNP-treated animals demonstrated an elevation in C-reactive protein, white blood cell count, blood urea nitrogen (BUN), creatinine, or liver enzymes. Total complement levels were highly variable, but variations were not significant. Also, no significant increase in cholesterol levels was noted with anti-HIV LNP administration (162±16.4 vs. 191±14.8 mg/dl). On physical examination of the injection site, naïve animals receiving free drug demonstrated a local reaction consisting of firm, nonerythematous swellings that resolved over the following weeks. Animals treated with anti-HIV LNP demonstrated no local reaction and their platelet counts remained within normal range.

In summary, taking advantage of the high LNP incorporation efficiency of two lipophilic protease inhibitors, LPV and RTV, and the ability to encapsulate hydrophilic TFV, we constructed a combination anti-HIV LNP and analyzed intracellular drug concentrations and plasma kinetics in macaques (*Macaca nemestrina*). Primates administered subcutaneously with anti-HIV LNPs exhibited elevated and extended intracellular drug levels in mononuclear cells of both blood and lymph nodes, indicating the utility of this approach to overcome lymph node drug insufficiency and associated viral persistence in patients on oral cART therapy. The ability of anti-HIV LNP to extend plasma drug levels for over 1 week with higher total drug exposure supports consideration as a long-acting agent to improve patient compliance. Importantly, three drugs packaged together in anti-HIV LNPs could reduce drug resistance potential by consistently and simultaneously delivering all three drugs above therapeutic levels in the same cell. This reduces the likelihood of varying intracellular concentrations for each drug, as achieved when delivered in free form or in separate particles. Therapeutic efficacy of anti-HIV LNPs could be further enhanced by organelle targeting with pH-responsive drug release and expressing CD4+-binding peptide to target HIV host cells. In summary, anti-HIV LNPs show promise for overcoming drug insufficiency in lymphoid tissues and improving patient compliance in search of a cure for AIDS.

Example 3

This example provides further description of anti-HIV drug-combination nanoparticles that enhance plasma drug exposure duration as well as triple-drug combination levels in cells within lymph nodes and blood in primates.

Abstract

HIV patients on combination oral drug therapy experience insufficient drug levels in lymph nodes, which is linked to viral persistence. Following success in enhancing lymph node drug levels and extending plasma residence time of indinavir formulated in lipid nanoparticles, we developed multidrug anti-HIV lipid nanoparticles (anti-HIV LNPs) containing lopinavir (LPV), ritonavir (RTV), and tenofovir (PMPA). These anti-HIV LNPs were prepared, characterized, scaled up, and evaluated in primates with a focus on plasma time course and intracellular drug exposure in blood and lymph nodes. Four macaques were subcutaneously administered anti-HIV LNPs and free drug suspension in a crossover study. The time course of the plasma drug concentration as well as intracellular drug concentrations in blood and inguinal lymph nodes were analyzed to compare the effects of LNP formulation. Anti-HIV LNPs incorporated LPV and RTV with high efficiency and entrapped a reproducible fraction of hydrophilic PMPA. In primates, anti-HIV LNPs produced over 50-fold higher intracellular concentrations of LPV and RTV in lymph nodes compared to free drug. Plasma and intracellular drug levels in blood were enhanced and sustained up to 7 days, beyond that achievable by their free drug counterpart. Thus, multiple antiretroviral agents can be simultaneously incorporated into anti-HIV lipid nanoparticles to enhance intracellular drug concentrations in blood and lymph nodes, where viral replication persists. As these anti-HIV lipid nanoparticles also prolonged plasma drug exposure, they hold promise as a long-acting dosage form for HIV patients in addressing residual virus in cells and tissue.

Introduction

Highly active antiretroviral therapy (HAART), a combination of antiretroviral drugs with different viral targets, can clear virus from the blood and maintain aviremia for several years. However, if daily oral therapy is interrupted, plasma viremia rapidly rebounds. Virus persists in lymph nodes and lymphoid tissues, where viral DNA and RNA remain detectable in patients on HAART even with plasma aviremia. HIV+ patients on HAART have lower drug concentrations in lymphoid tissues relative to concurrent plasma concentrations, which has been linked to persistent lymphatic viral replication. Enhancing and extending drug exposure in lymphoid tissues are essential for clearing residual virus to find a cure for HIV.

We have previously found that lipid nanoparticles (LNPs) containing a protease inhibitor, indinavir (IDV), produced elevated drug levels in lymph nodes throughout the body and extended plasma residence time. In HIV-infected primates, treatment with these IDV-LNPs reversed CD4+ T cell decline and reduced viral RNA in plasma and lymph nodes. These LNPS have been documented to incorporate other protease inhibitors as well as a hydrophilic drug tenofovir (PMPA), a nucleotide analog reverse transcriptase inhibitor (NRTI) and the active drug in Viread. Since monodrug regimens may promote resistance, and combination drug therapies targeted to multiple HIV proteins reduce mortality, multiple drugs formulated in a single particle may enhance therapeutic potency and tissue viral clearance.

Therefore, we developed and evaluated in primates a three-drug combination lipid nanoparticle (anti-HIV LNP) containing lopinavir (LPV), ritonavir (RTV), and PMPA. LPV and RTV were selected due to their acid stability and hydrophobicity, which promotes lipid association. Ritonavir, a metabolic and transport inhibitor, is used clinically to enhance the efficacy of coadministered drugs. PMPA, being an NRTI, provides an additional site of antiviral action, and its phosphorylated form is retained intracellularly, thus prolonging antiviral activity. This combination is clinically relevant and favorable to extending and enhancing intracellular drug exposure. We found that a subcutaneous injection of anti-HIV LNPs in primates produced enhanced intracellular drug concentrations in mononuclear cells of lymph nodes (LNMCs) and peripheral blood (PBMCs) and prolonged residence time in PBMCs and plasma compared to free drug in suspension. Long-acting anti-HIV lipid nanoparticles have the potential to overcome drug insufficiency and the associated viral persistence in lymphoid tissues.

Materials and Methods

Materials and Animals 1,2-Distearoyl-sn-glycero-3-phosphocholine (DSPC) and N-(carbonylmethoxypolyethyleneglycol-2000)-1,2-distearoylsn-glycero-3-phosphoethanolamine, sodium salt (MPEG-2000-DSPE) were purchased from Corden Pharma (Liestal, Switzerland). LPV, RTV, and PMPA ([(2R)-1-(6-aminopurin-9-yl)propan-2-yl]oxymethylphosphonic acid) were purchased from Waterstone Technology (Carmel, Ind.). Other reagents were analytical grade or higher.

Four young adult male macaques (*Macaca nemestrina*, 2.9-4.0 kg) were housed and cared for by the Washington National Primate Research Center (WaNPRC) under an approved Institutional Animal Care and Use Committee protocol. One animal developed an unrelated illness that necessitated discarding that individual's second round PBMC data.

Lipid nanoparticle preparation and in vitro characterization LNPs composed of DSPC:MPEG-2000-DSPE (8:2 or 9:1 molar ratio), LPV, RTV, and PMPA (115:10:5:15 lipid:LPV:RTV:PMPA molar ratio) were prepared aseptically according to previously established methods. Kinman L, Brodie S J, Tsai C C, et al.: Lipid-drug association enhanced HIV-1 protease inhibitor indinavir localization in lymphoid tissues and viral load reduction: A proof of concept study in HIV-2287-infected macaques. *J Acquir Immune Defic Syndr* 2003; 34(4):387-397, incorporated herein by reference in its entirety. Briefly, lipids and protease inhibitors were dissolved in chloroform:ethanol (3:1 v/v) and PMPA was added from a stock solution of 30 mg/ml in aqueous 150 mM NaHCO$_3$. Solvent was removed by rotary evaporation and vacuum desiccation. The dry film was rehydrated to 200 mM lipid in 0.4% NaCl with 20 mM NaHCO$_3$ buffer at 60° C. Particle size was reduced at 60° C. by bath sonication (laboratory scale) or high-pressure homogenization using an Emulsiflex-05 (Avestin, Ottawa, Canada) (clinical scale). LNPs were maintained at 60° C. to anneal for 30 min prior to cooling and stored at 4° C. Particle size was determined by photon correlation spectroscopy using a NICOMP 380 ZLS (Particle Sizing Systems, Santa Barbara, Calif.). Osmolality (Vapro 5520 osmometer; Wescor, Logan, Utah) and pH (Hydrion paper) were assessed.

The anti-HIV LNP formulations contain both unbound drug and drugs bound to lipid nanoparticles. To determine drug incorporation/encapsulation efficiencies, anti-HIV LNPs were dialyzed (MWCO 6,000-8,000) at room temperature against 1,000× volume bicarbonate-buffered saline for 4 h to remove unbound drug. Drugs were quantified by LC-MS/MS using acetonitrile precipitation. Encapsulation efficiency (EE) was calculated as follows:

$$EE = \frac{\text{Drug concentration in anti-}HIV\ LNPs\ \text{after dialysis}}{\text{Drug concentration in anti-}HIV\ LNPs\ \text{before dialysis}} \times 100$$

The antiviral activity of the three-drug combination in soluble or LNP form was evaluated in HIV-infected CEM-174 cells as described previously. Kinman L, Brodie S J, Tsai C C, et al.: Lipid-drug association enhanced HIV-1 protease inhibitor indinavir localization in lymphoid tissues and viral load reduction: A proof of concept study in HIV-2287-infected macaques. *J Acquir Immune Defic Syndr* 2003; 34(4):387-397, incorporated herein by reference in its entirety. After 4 days of incubation with drug, cells were observed for syncytia, and viral infection was confirmed by ELISA detection of HIV-2 p27. The ratio of LPV, RTV, and PMPA was fixed at 1:1:0.5 (m/m/m) for antiviral activity evaluation. The dose of drugs added to cells represents the sum of bound and unbound drugs in these anti-HIV LNP formulations.

Preparation of Free Drug Suspension for Primate Study

Two free drug suspensions were prepared at the same molar ratios as for anti-HIV LNPs (LPV:RTV:PMPA 2:1:3, m/m/m). The vehicle for the first suspension was bicarbonate-buffered saline with 3% ethanol and 0.2% bovine serum albumin. The vehicle for the second suspension was bicarbonate-buffered saline with 8% DMSO and 0.1% Tween 20.

Sterility of Preparations for Injection

All preparations for injection were prepared using injection-grade aqueous solutions and an aseptic technique. Non-sterile aqueous components were sterilized by passage through a 0.22-lm cellulose acetate filter. Sterility was verified by a blood agar culture test for 7 days at 37° C.

Subcutaneous Administration of Free and Lipid-Associated Drug Combination to Macaques Four macaques were divided into two treatment groups (two animals per group). Each animal received both free drug and anti-HIV LNPs (bound and free drug mixture) in a crossover study with a washout period of over 12 weeks between experiments. Anti-HIV LNPs were dosed at 25.0, 14.3, and 17.1 mg/kg of LPV, RTV, and PMPA, respectively, in 20 ml delivered subcutaneously on the back. Free drug suspension was dosed slightly lower (20.0, 11.5, and 13.7 mg/kg LPV, RTV, and PMPA, respectively) in the same volume due to limited solubility. Data were normalized to the anti-HIV LNP dose for comparative analysis.

Blood and Tissue Sample Collection and Processing

Blood samples were collected in EDTA by femoral venous puncture at 0, 0.5, 1, 3, 5, 8, 24, and 168 h, plus 48 h (both groups) and 120 h (anti-HIV LNP group) in the second round of the study. Plasma was removed, PBMCs were isolated by the density gradient method, and cells were aliquoted into pellets of approximately 2 million PBMCs each. An inguinal lymph node was surgically excised 24 h after drug administration (n=2 per treatment), LNMCs were isolated by passage through a 100-lm nylon cell strainer (Corning, Tewksbury, Mass.), and cells were aliquoted into pellets of approximately 1-2 million LNMCs each. All samples were stored at −80° C. prior to drug analysis.

Determination of Drug Concentrations in Plasma and Cells

Plasma concentrations of all three drugs were analyzed simultaneously by liquid chromatography-tandem mass spectrometry using a recently published method. Koehn J and Ho R J, Novel liquid chromatography-tandem mass spectrometry method for simultaneous detection of anti-HIV drugs lopinavir, ritonavir, and tenofovir in plasma. *Antimicrob Agents Chemother* 2014; 58(5):2675-2680, incorporated herein by reference in its entirety. PBMC and LNMC pellets were lysed using 200 µl water/methanol (1:1 v/v), sonicated for 10 min, and then extracted and analyzed using the same method as cited above. Intracellular concentrations were converted to ng/ml with the assumption that each cell has a volume of $4 \times 10^{-9}$ ml. Alberts B, Johnson A, Lewis J, et al. *Molecular Biology of the Cell*, 4 ed. Garland Science, New York, 2002, incorporated herein by reference in its entirety.

Determination of Plasma Drug Exposure

Area under the curve (AUC) was calculated for the total evaluated time period (0-168 h) as well as from 0 to 24 and 24 to 168 h using the trapezoidal rule. Data were analyzed by paired two-tailed Student's t-test with $p<0.05$ considered statistically significant.

Assessment of Immunological and Inflammatory Response

Blood was collected at least 1 week prior to and exactly 7 days after drug administration for analysis of complete blood count, serum chemistry, C-reactive protein, and total complement. Reference values for *Macaca nemestrina* were provided by the WaNPRC. Human reference values were used for C-reactive protein and total complement due to limited primate data. Animals were observed daily for physical or behavioral changes.

Results

Physicochemical properties and antiviral activity of anti-HIV nanoparticles composed of lopinavir, ritonavir, and tenofovir In preparation for primate studies, anti-HIV LNPs containing LPV, RTV, and PMPA were optimized on a laboratory scale (0.1-0.4 ml) and scaled up to clinical scale (14-40 ml) using equipment capable of multiliter capacity. Protease inhibitor incorporation efficiency was reproducibly high, with clinical scale batches showing over 90% LPV and RTV incorporation (Table 7). PMPA association was consistent and reproducible (Table 7). High-pressure homogenization resulted in slightly smaller particles (~50 nm diameter) compared to those produced by sonication (~70 nm diameter). The pH and osmolality of the anti-HIV LNP preparations were physiologically compatible, and a culture test verified sterility suitable for primate studies.

TABLE 7

Physicochemical Characteristics of Anti-HIV Lipid Nanoparticles Produced on a Laboratory or Clinical Scale

| | Degree of incorporation (% total) | | | Particle | | |
|---|---|---|---|---|---|---|
| | Lopinavir | Ritonavir | Tenofovir | diameter (nm)[a] | pH | Osmolality |
| Laboratory scale[b] (0.1-0.4 ml) | 74.2 ± 7.3 | 74.2 ± 8.4 | 11.8 ± 5.1 | 68.3 ± 14.0 | 7.0 ± 0.3 | 334 ± 39 |
| Clinical scale[c] (15-40 ml) | 93.6 ± 5.5 | 90.7 ± 7.4 | 11.9 ± 3.0 | 52.4 ± 9.1 | 7.0 ± 0.5 | 266 ± 31 |

[a]Particle size was determined by Nicomp intensity-weighted analysis.
[b]Anti-HIV LNPs were reproduced in 0.1-0.4 ml batches, with values expressed as mean ± standard deviation of five batches.
[c]Anti-HIV LNPs were reproduced in 15-40 ml batches, with values expressed as mean ± standard deviation of three batches.
Anti-HIV LNPs were prepared at a lipid:LPV:RTV:PMPA molar ratio of 115:10:5:15 and a final lipid concentration of 200 mM. The degree of drug incorporation in the three drugs-LPV:RTV:PMPA (2:1:3 mole ratio)-was determined as described in Materials and Methods for reproducibility and other characteristics. The anti-HIV LNPs contain both free and bound drugs in a well-defined fraction. LNP, lipid nanoparticle; LPV, lopinavir; RTV, ritonavir; PMPA, tenofovir.

The antiviral potency of LNP-associated LPV, RTV, and PMPA was evaluated in HIV-infected CEM-174 cells and compared to soluble free drugs combined in equivalent ratios or used individually. At a 1:1:0.5 (m/m/m) drug ratio, respectively, anti-HIV LNPs exhibited a 30-fold increase in potency over the drugs combined in soluble form (LPV, RTV, and PMPA EC$_{50}$ 3.0±0.8, 3.0±0.8, and 1.5±0.1 nM in LNP form vs. 98±0.3, 98±0.3, and 49±0.2 nM in free form). Single agent EC$_{50}$ values for LPV, RTV, and PMPA were 600±0.04, 530±0.2, and 1150±0.7 nM, respectively. Control lipid nanoparticles exhibited no antiviral effects.

multiple drug lipid nanoparticle formulated dose to provide a therapeutic effect. Furthermore, a reduction in total dose, along with anticipated lower plasma peak levels of tenofovir can be readily optimized to lead to a safer, yet more effective product.

TABLE 8

Effects of Anti-HIV Lipid Nanoparticles on Plasma Drug Exposure in Primates Treated With Lopinavir, Ritonavir, and Tenofovir in Combination

| | AUC (μg · h · ml$^{-1}$)[a] | | | AUC$_{fraction}$ (% of total)[b] | | | |
|---|---|---|---|---|---|---|---|
| | Free drug | Anti-HIV LNP | LNP/free | Free drug | | Anti-HIV LNP | |
| Drug | 0-168 h | 0-168 h | ratio | 0-24 h | 24-168 h | 0-24 h | 24-168 h |
| Lopinavir (LPV) | 3.83 ± 4.04 | 69.6 ± 10.7 | 18.2 | 56.6 ± 9.4 | 43.5 ± 9.4 | 37.2 ± 9.9 | 62.8 ± 9.9 |
| Ritonavir (RTV) | 1.39 ± 1.18 | 19.4 ± 12.2 | 14.0 | 84.1 ± 18.9 | 15.9 ± 18.9 | 43.0 ± 12.5 | 57.0 ± 12.5 |
| Tenofovir (PMPA) | 56.6 ± 17.04 | 395.0 ± 344.5 | 7.0 | 99.9 ± 0.2 | 0.1 ± 0.2 | 48.8 ± 33.7 | 51.2 ± 33.7 |

[a]Four animals were treated with lopinavir (25 mg/kg), ritonavir (14.3 mg/kg), and tenofovir (17.1 mg/kg) administered subcutaneously in either free or LNP form. Plasma drug concentrations were measured and area under the curve (AUC) was calculated using the trapezoidal rule. Data are expressed as mean ± standard deviation for four animals over a 168-h period.
[b]AUC was analyzed from 0 to 24 h, which represents the standard dosing period for current HAART, and from 24 to 168 h to demonstrate the extended plasma exposure provided by anti-HIV LNPs. Values are expressed as a percent of the total AUC, mean ± standard deviation.

Effects of LNP Association on Plasma Time Course and Total Drug Exposure

Figure 6A:
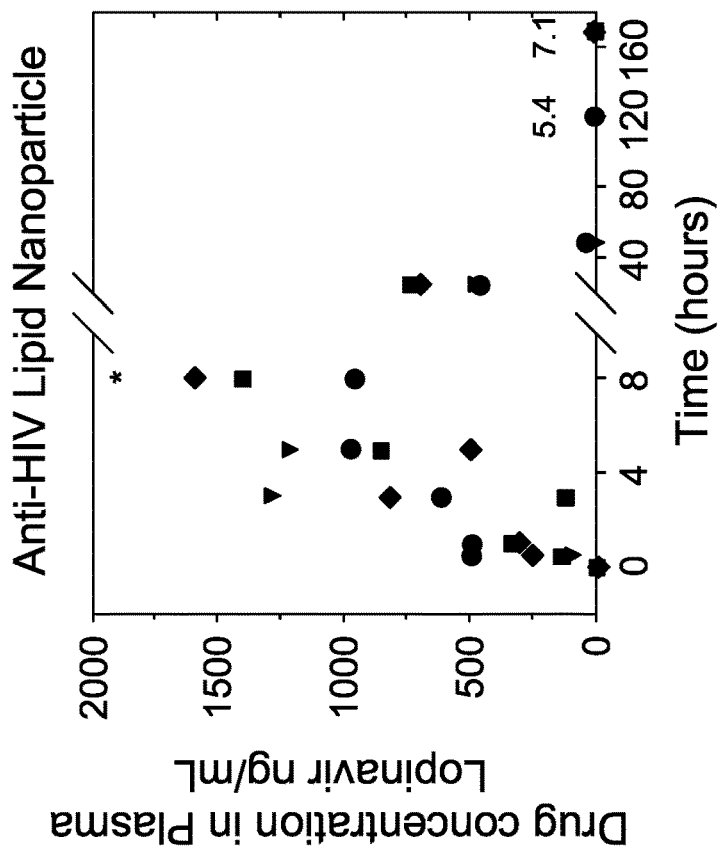
FIGS. 6A-6F graphically illustrate the plasma concentration of lopinavir (LPV), ritonavir (RTV), and tenofovir (PMPA) over time after subcutaneous administration in either free (FIGS. 6A, 6C, 6E) or lipid nanoparticle (FIGS. 6B, 6D, 6F) formulation at a normalized dose of 25 mg/kg LPV, 14.3 mg/kg RTV, and 17.1 mg/kg PMPA. Data points represent individual animals (circle, M10066; triangle, M10068; square, R10142; diamond, Z11084; open, free drug; solid, LNP). Time points with a mean value of less than 10 ng/ml are annotated. *Outlier omitted: 3285.76 ng/ml at 8 h for animal M10068.
Figure 6B:
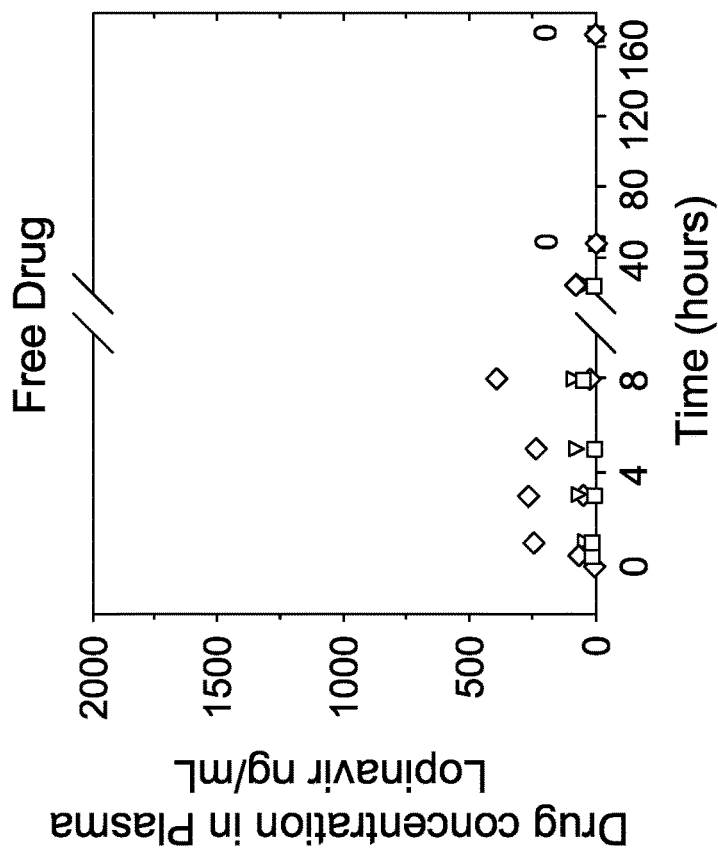
Figure 6D:
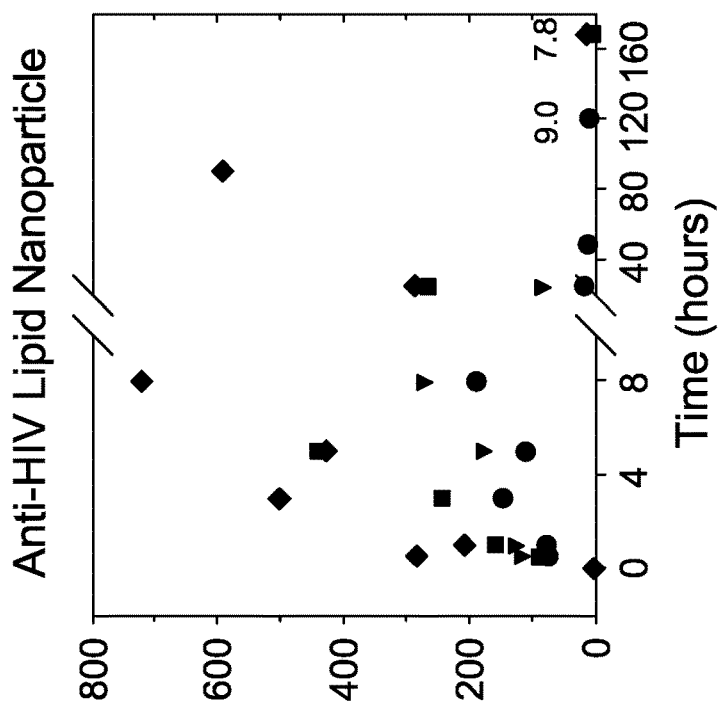
Figure 6C:
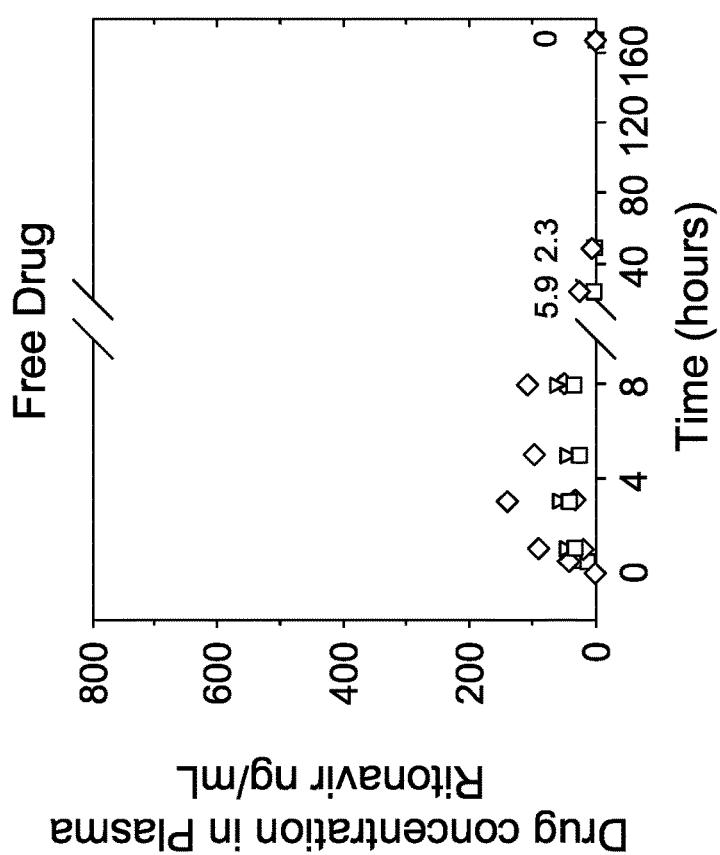
Figure 6F:
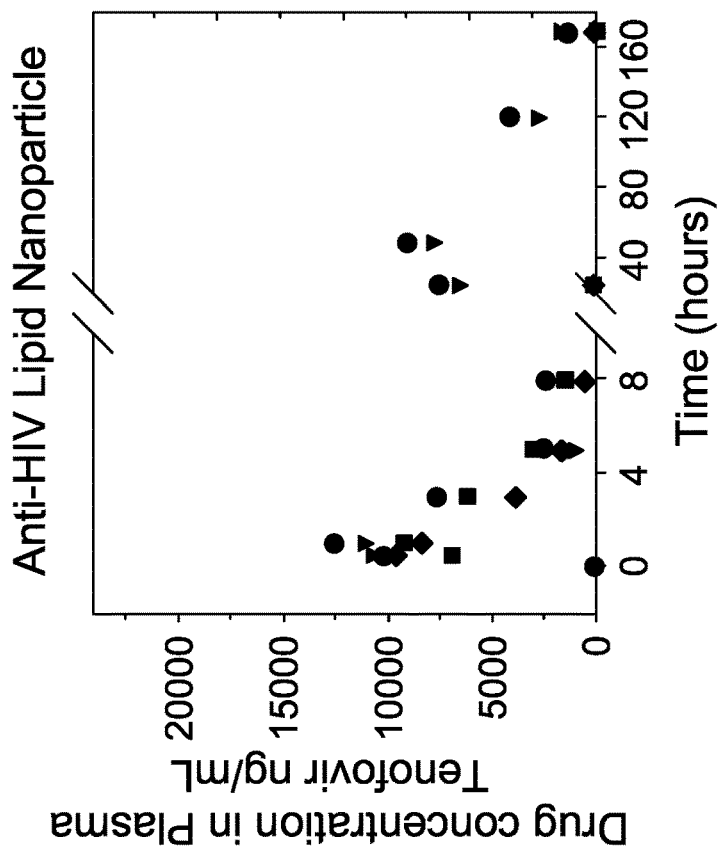
Figure 6E:
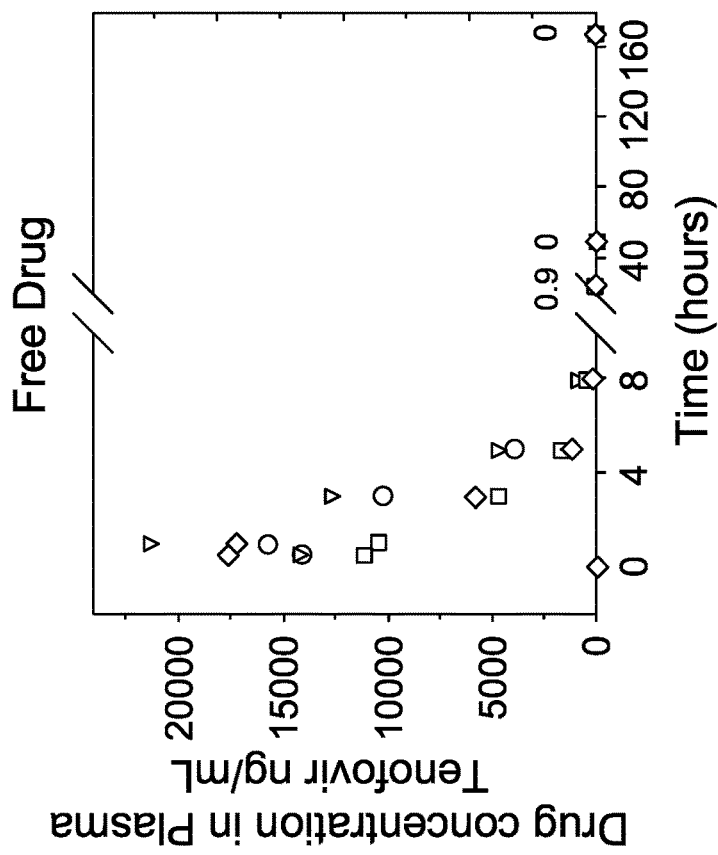

Primates received a single subcutaneous dose of LPV, RTV, and PMPA in either anti-HIV LNPs or free suspension form. Following free drug administration, plasma concentrations peaked within 8 h and dropped to low or undetectable levels by 24 h (FIGS. 6A-6F). In contrast, macaques treated with anti-HIV LNPs demonstrated elevated plasma concentrations of LPV and RTV at all time points evaluated and higher peak plasma concentrations of LPV and RTV (p<0.05), and all three drugs remained detectable in plasma at 7 days (168 h) post-administration at levels within the effective virucidal concentrations (even without further optimization). LNP-associated PMPA demonstrated two peaks: the first peak was similar to that seen after free drug administration, while the second peak was not seen with free drug (FIGS. 6E and 6F).

Figure 7A:
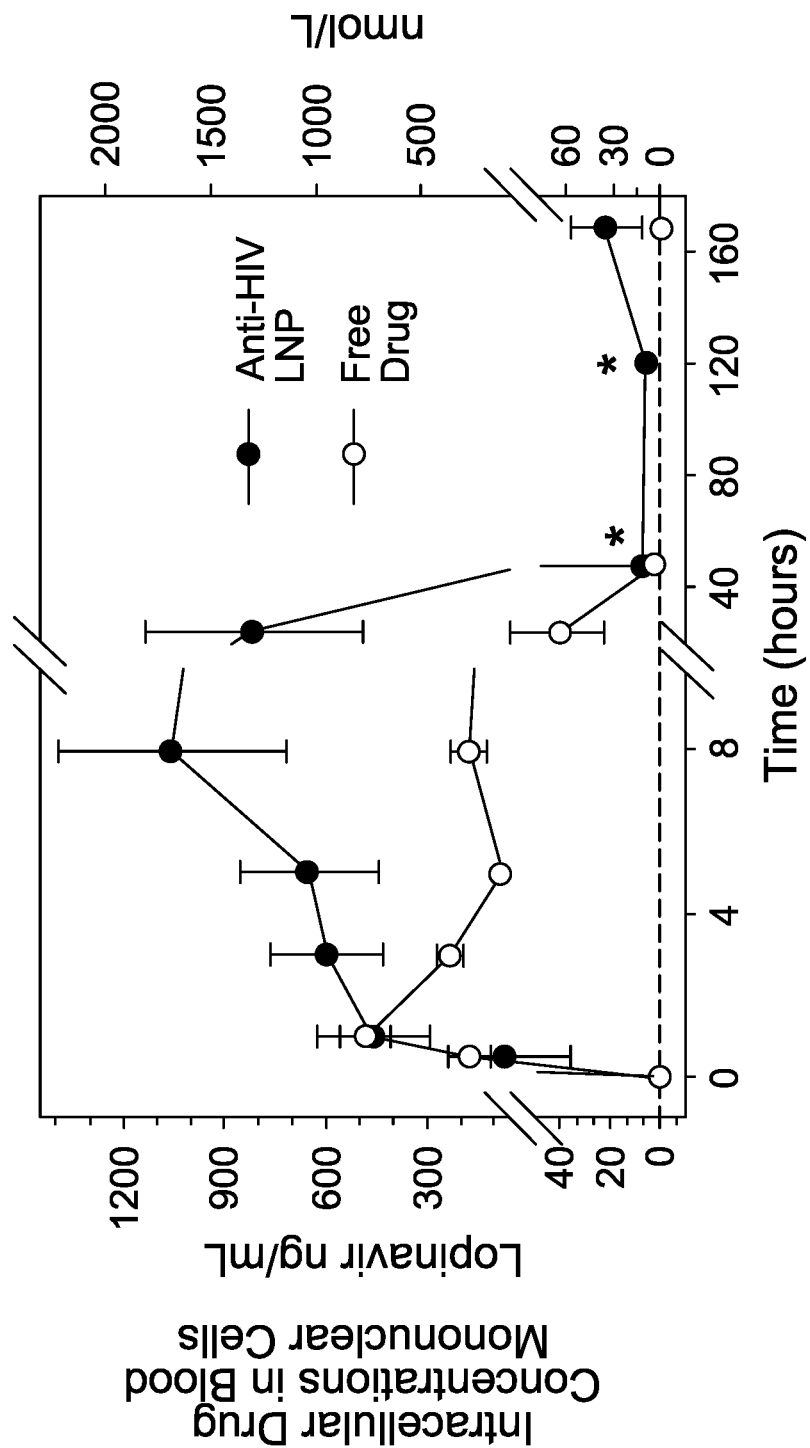
FIGS. 7A-7C graphically illustrate the mean intracellular concentration of lopinavir (LPV) (FIG. 7A), ritonavir (RTV) (FIG. 7B), and tenofovir (PMPA) (FIG. 7C) in peripheral blood mononuclear cells (PBMCs) over time after subcutaneous administration in either free (open symbols) or lipid nanoparticle (solid symbols) formulation at a normalized dose of 25 mg/kg LPV, 14.3 mg/kg RTV, and 17.1 mg/kg PMPA. Concentrations are expressed as ng/ml (left y axis) and nmol/liter (right y axis). Error bars show standard error of the mean (SEM). For free drug, n=4 except at 48 h and 120 h n=2. For anti-HIV LNP, n=3, except at 48 h and 120 h n=1. *Cannot calculate SEM for anti-HIV LNPs at 48 h and 120 h time points due to n of 1.
Figure 7B:
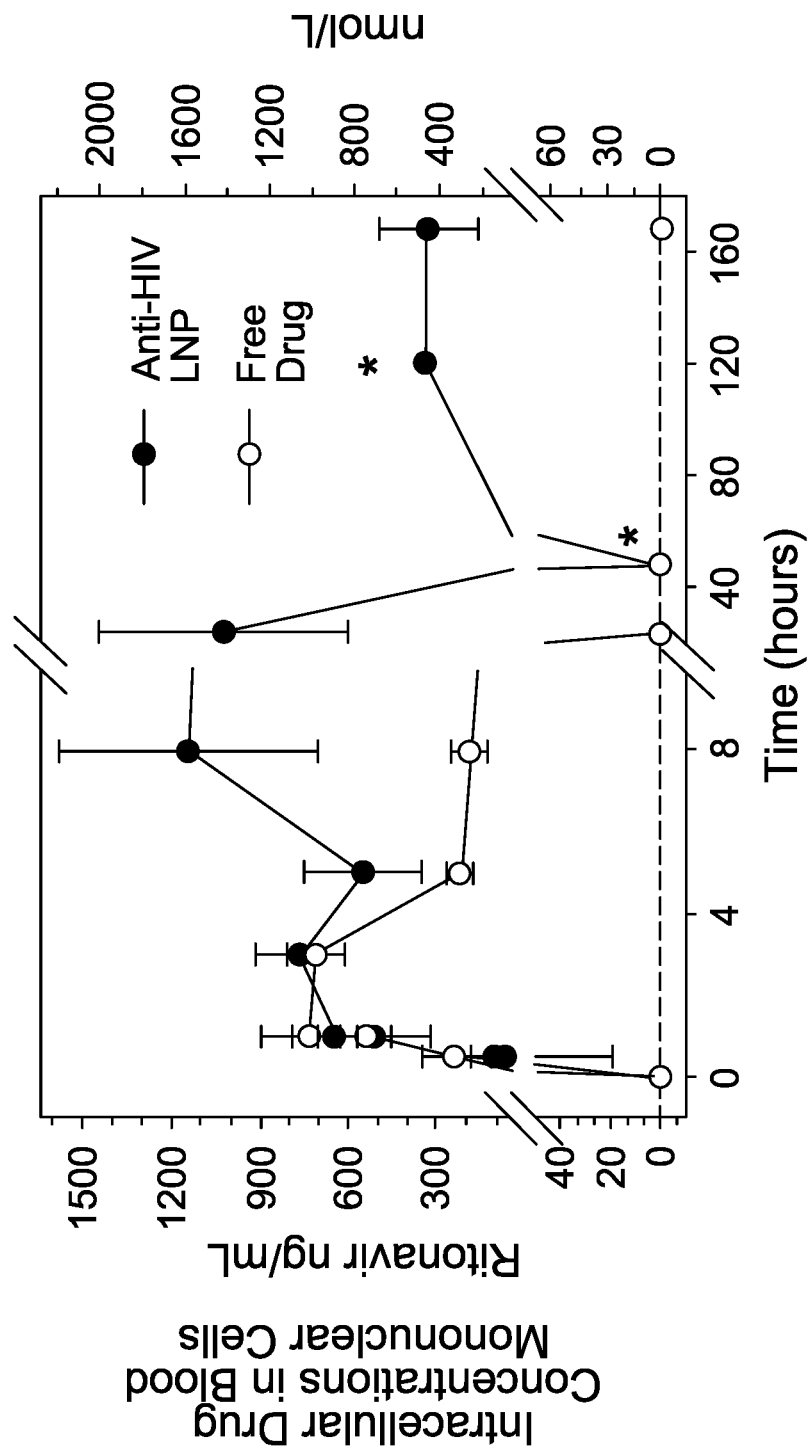
Figure 7C:
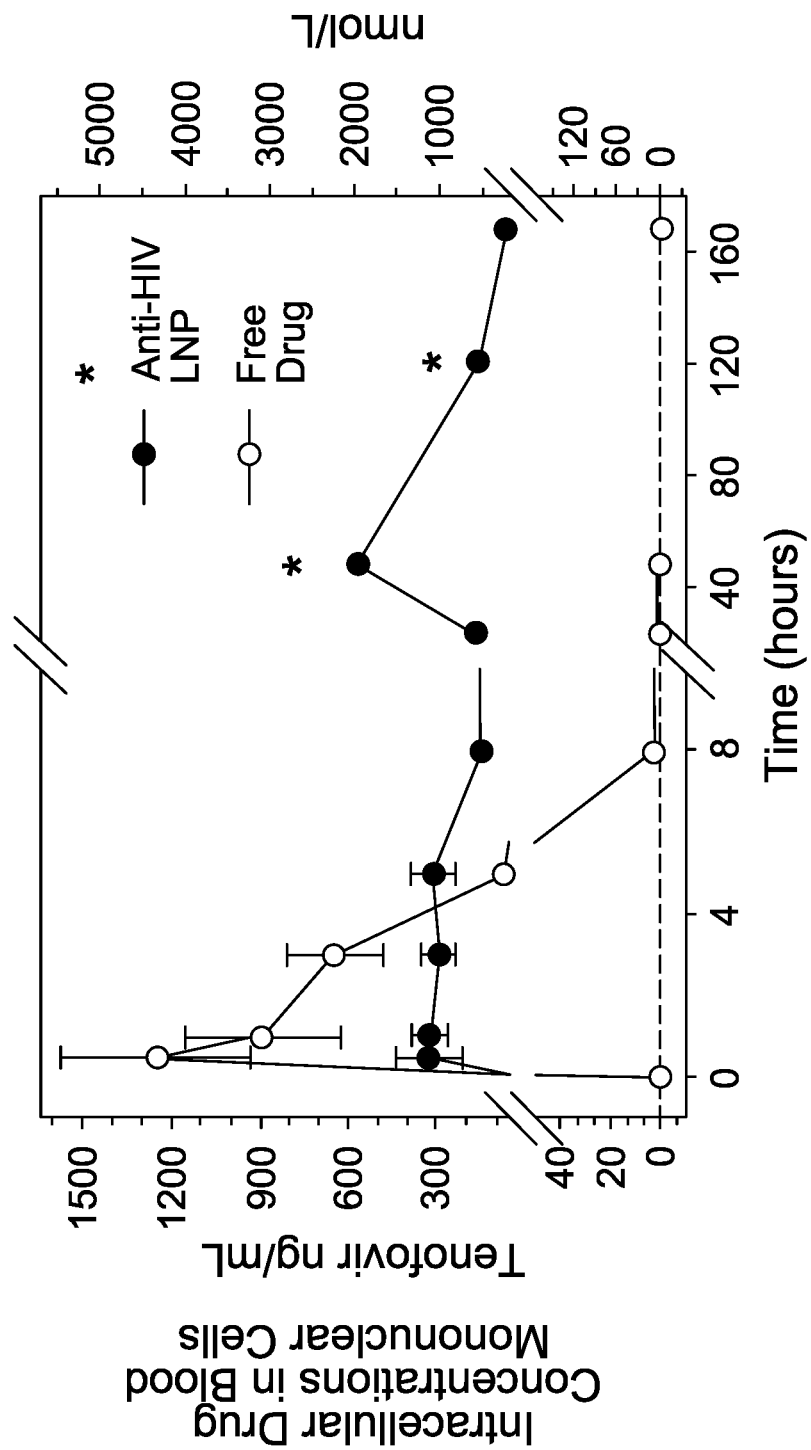

Total drug exposure was assessed by calculating the area under the plasma drug concentration curve (AUC). As shown in Table 8, anti-HIV LNPs provided a 7-fold or greater increase in total drug exposure for all three drugs when compared to free drug suspension (≤0.05, 0.07, and 0.173 for LPV, RTV, and PMPA, respectively). Additionally, the percentage of total drug exposure that occurred after the first 24 h was increased for all three drugs with anti-HIV LNPs. This shift was most dramatic for hydrophilic PMPA (0.1% with free drug, 51.2% with anti-HIV LNPs) (Table 8). These data indicate that the LNP formulation provides enhanced and extended plasma drug exposure for all three drugs, including water-soluble PMPA with only 12% drug association. It is noted that the initial peak plasma concentration of tenofovir (PMPA or TFV) occurring in the first 24 hr is reduced significantly. Such a reduction in peak plasma concentration for tenofovir could reduce the untoward effects related to high peak plasma concentration of that drug. It is also interesting to note that the overall plasma drug exposure with lipid nanoparticle formulated drug combination is within the extended period from 24-168 hr for the seven-day study (right column in Table 8). Considering that the 7- to 18-fold total exposure enhancement and the free drug dose chosen for this study is equivalent to the therapeutic primate SHIV treatment dose (e.g., 20 mg PAMA and 50 mg/kg FTC SC daily), it follows that the equivalent of seven daily free-drug doses can be provided using only one Effect of LNP Association on Intracellular LPV, RTV, and PMPA Concentrations in Blood and Lymph Node Mononuclear Cells While plasma drug levels indicate sustained drug exposure, intracellular levels are essential for inhibition of viral replication. Thus, mononuclear cells in blood (PBMCs) were isolated and intracellular concentrations of LPV, RTV, and PMPA were determined. As illustrated in FIGS. 7A-7C, macaques treated with anti-HIV LNPs had detectable intracellular drug levels at 7 days post-administration that exceeded the experimental EC$_{50}$ reported above. In contrast, intracellular drug levels after free drug administration generally fell below detection by 48 h (FIGS. 7A-7C). LPV and RTV concentrations after anti-HIV LNP administration were comparable to free drug at early time points and up to 20-fold greater at later time points. Water-soluble PMPA exhibited lower intracellular drug levels for the first five time points with anti-HIV LNPs; however, by 8 h post-administration, intracellular PMPA concentrations were over 50-fold higher in LNP-treated animals (FIGS. 7A-7C).

To determine the effect of LNP association on intracellular drug concentrations in LNMCs, an inguinal lymph node was collected 24 h after drug administration. LNMCs were isolated and intracellular drug concentrations were compared between test groups (LNP-to-free ratio) and to concurrent plasma drug concentrations (Table 9). LPV and RTV concentrations were low or undetectable in LNMCs of animals treated with free drug combination, and comparable to plasma concentrations. In contrast, concentrations of LPV and RTV in LNMCs after anti-HIV LNP administration were 2-fold and 10-fold higher, respectively, than concurrent plasma concentrations and over 50-fold higher than LNMC concentrations after free drug administration (p<0.05). Additionally, plasma concentrations of LPV and RTV at 24 h were approximately 25-fold higher with anti-HIV LNPs compared to free drug (Table 9). PMPA, while consistently detectable in LNMCs, showed no significant difference in intracellular lymph node concentrations between the two test groups (p=1.0). Intracellular drug levels in PBMCs and LNMCs at 24 h were comparable. Taken together, anti-HIV LNPs containing LPV, RTV, and PMPA enhanced and prolonged intracellular levels of all three drugs in blood as well as in lymph nodes, and produced greater concentrations of LPV and RTV in LNMCs than in plasma at 24 h post-administration.

TABLE 9

The Effect of Anti-HIV Lipid Nanoparticles on the Intracellular Concentrations of Lopinavir,
Ritonavir, and Tenofovir in Lymph Nodes Compared to Plasma Concentrations at 24 h

|  | Mean drug concentration (ng/ml) | | | | | | Ratio comparison between treatments | |
| --- | --- | --- | --- | --- | --- | --- | --- | --- |
|  | Free drug treatment[a] | | | Anti-HIV LNP treatment[a] | | | (LNP/free)[b] | |
| Drug | Lymph node | Plasma | LN/plasma ratio[c] | Lymph node | Plasma | LN/plasma ratio[c] | Lymph node | Plasma |
| Lopinavir | 0.0 ± 0.0 | 24.5 ± 26.3 | <0.1 | 1212.3 ± 9.8 | 596 ± 122.7 | 2.0 | >1212.3 | 24.4 |
| Ritonavir | 32.6 ± 32.6 | 5.9 ± 9.3 | 5.5 | 1641.8 ± 19.0 | 163.6 ± 115.6 | 10.0 | 50.3 | 27.9 |
| Tenofovir | 255.7 ± 31.5 | 0.9 ± 1.1 | 284.1 | 189.9 ± 22.8 | 3598.9 ± 3508.5 | 0.1 | 0.7 | 3992.8 |

[a]Animals were administered anti-HIV LNPs or free drug at a normalized dose of 25 mg/kg LPV, 14.3 mg/kg RTV, and 17.1 mg/kg PMPA subcutaneously. A blood sample and inguinal lymph node were collected 24 h after drug administration and lymph node mononuclear cells were isolated for drug analysis. Intracellular drug concentrations were calculated as described in Materials and Methods. Drug concentrations are reported as mean ± standard deviation (n = 2).
[b]Mean anti-HIV LNP drug concentration divided by mean free drug concentration. In cases where the drug level was below detectable limits, the number was taken as "1" to calculate the ratio.
[c]Mean lymph node intracellular drug concentration divided by mean plasma drug concentration. In cases where the drug level was below detectable limits, the number was taken as "1" to calculate the ratio.

Safety Evaluation of Immunological and Inflammatory Response

To evaluate safety, primate blood samples taken before and after drug administration were analyzed for complete blood count, serum chemistry panel, C-reactive protein, and total complement. Relevant values are summarized in Table 10. Indicators of renal and hepatic function (blood urea nitrogen, creatinine, liver enzymes) stayed within normal limits. No animals demonstrated increased C-reactive protein or white blood cell count to a value outside of the reference range. Total complement, while highly variable, showed no significant changes. A slight cholesterol level variation with anti-HIV LNP treatment was not statistically significant (p=0.07). Naive animals receiving free drug demonstrated a local reaction consisting of firm, nonerythematous swellings that resolved over the following weeks along with mildly increased platelet counts. Naive animals that received anti-HIV LNPs demonstrated no local reaction and their platelet counts remained within normal limits.

TABLE 10

Changes in Selected Inflammatory Indicators and Cholesterol After Subcutaneous Administration of Lopinavir, Ritonavir, and Tenofovir in Free or Anti-HIV Lipid Nanoparticle Form[a]

|  | Baseline[b] | After free drug[c] | p-value[d] | After LNP[c] | p-value[d] |
| --- | --- | --- | --- | --- | --- |
| WBC (thousands/μl) | 10.1 ± 4.3 | 8.6 ± 1.9 | 0.92 | 11.7 ± 3.6 | 0.93 |
| Platelet (thousands/μl) | 496 ± 102 | 576 ± 125 | 0.04 | 636 ± 117 | 0.10 |
| Total complement (U/ml) | 129 ± 73 | 146 ± 76 | 0.31 | 139 ± 59 | 0.76 |
| C-Reactive protein (mg/liter) | 0.2 ± 0.0 | <0.2 ± 0.0 | 1.00 | <0.2 ± 0.0 | 0.39 |
| Cholesterol (mg/dl) | 162 ± 16 | 162 ± 24 | 0.80 | 191 ± 15 | 0.07 |

[a]Venous blood samples were analyzed for complete blood count, serum chemistry, total complement, and C-reactive protein. Values are expressed as mean ± standard deviation. No parameters excluded from this table showed a post-administration increase to a value outside of the reference range in any primates (n = 4).
[b]To establish a baseline, blood was collected at least 7 days prior to drug administration.
[c]Blood was collected 7 days after drug administration.
[d]p-value was determined by paired two-tailed Student's t-test.

Discussion

Capitalizing on the ability of lipid nanoparticles to efficiently incorporate two lipophilic protease inhibitors, LPV and RTV, and simultaneously encapsulate a significant fraction of PMPA, we constructed a drug combination anti-HIV LNP and analyzed intracellular drug concentrations and plasma kinetics in macaques (*M. nemestrina*). Primates dosed subcutaneously with anti-HIV LNPs exhibited extended plasma drug levels (FIGS. 6A-6F), had higher total drug exposure (Table 8), and sustained intracellular concentrations of LPV, RTV, and PMPA in blood (FIGS. 7A-7C). Importantly, drugs in anti-HIV LNPs provided much higher intracellular levels of LPV and RTV in lymph nodes, beyond those achieved with free drug (Table 9). These findings indicate that lipid nanoparticles may overcome the drug insufficiency reported with HIV-infected patients on oral HAART.

Employing a simple, reproducible, and scalable production method, these nanoparticles stably incorporate LPV and RTV with >90% efficiency while simultaneously encapsulating a hydrophilic reverse transcriptase inhibitor, PMPA (Table 7). The PMPA association was consistent and well-defined, and unassociated PMPA was left in the solution as free drug, reducing drug wastage and the risk of contamination as well as eliminating the need for costly and time-consuming purification. Due to space limitations, additional details on optimization and in vitro characterization of anti-HIV LNPs are beyond the scope of this report and will be reported separately.

A subcutaneously administered three-drug combination of anti-HIV LNPs increased peak plasma concentrations, prolonged plasma residence time, and increased plasma drug exposure as evidenced by an increase in AUC (FIGS. 7A-7C and Table 8). Considering the 12% encapsulation efficiency of PMPA, these findings indicate that limited encapsulation of hydrophilic PMPA still makes a marked impact on drug distribution and/or metabolism. Enhanced stability and reduced renal and hepatic drug clearance provided by the LNPs may contribute to these findings, although the behavior and form of anti-HIV LNPs in vivo remain to be explored.

Intracellular drug exposure is a vital consideration if a drug is to maximally suppress viral replication in cells. For all three drugs, a lipid-drug association enhanced intracellular drug concentrations in PBMCs and LNMCs, suggesting that LNPs are internalized and retained in mononuclear cells (FIGS. 7A-7C and Table 9). While this nonterminal study allowed analysis of only a single peripheral lymph node, previous work with indinavir-containing LNPs has shown elevated indinavir concentrations in lymph nodes throughout the body (including mesenteric, tonsillar, bronchial, and others). Thus, a widespread lymphatic distribution of drug-containing LNPs is achievable. Therefore, anti-HIV LNPs hold promise as a vehicle for simultaneous widespread lymphatic distribution of multiple anti-HIV drugs, overcoming lymphatic drug insufficiency in sites of viral persistence.

Presenting multiple drugs with different viral targets within a single particle is important for improving antiviral efficacy and reducing the risk of viral resistance. While a number of efforts have been made to develop single-drug nanoparticles to be combined at the time of administration, this approach may result in heterogeneity of intracellular drug concentrations and potentially harbor drug-resistant virus. Solid polymeric particles 100-600 nm in diameter containing multiple crystalline drugs have been synthesized, but these are much larger than anti-HIV LNPs and may not be suitable for lymphatic uptake. While the mechanisms of drug action in anti-HIV LNPs remain to be elucidated, cellular uptake of intact nanoparticles followed by pH- or phospholipase-dependent release of active drug likely leads to enhanced intracellular levels. This mechanism, using acid-stable drugs in combination, provides a concerted antiviral effect compared to drugs in free form or separate nanoparticles. Further studies are planned to evaluate the therapeutic efficacy of multidrug anti-HIV LNPs in an HIV-infected macaque model.

With daily oral HAART therapy, treatment interruption is often correlated with adverse side effects or drug abuse. Gastrointestinal side effects cause patients to skip doses, and patients with a history of drug abuse are three times more likely to discontinue treatment, leading to rapid viral rebound. The elevated and sustained plasma and intracellular drug exposures achieved with a single dose of anti-HIV LNPs indicate the feasibility of less frequent (e.g., once weekly) dosing, reducing the likelihood of treatment interruption. While dose-ranging and multiple-dose studies are needed to optimize dose and dosing frequency, our predictive model indicates that once weekly dosing with anti-HIV LNPs is feasible. Studies evaluating intracellular drug levels in lymph nodes throughout the body and lipid-particle distribution using gadolinium tracers are planned, but are beyond the scope of this report.

In addition to presenting multiple antiviral compounds, the anti-HIV LNP platform offers the possibility of cell and organelle targeting with pH-dependent drug release, expression of a CD4-binding peptide, or other surface modifications. Eliciting little or no local or systemic inflammatory reaction, these anti-HIV lipid nanoparticles hold promise for delivery of HIV drugs such as LPV, RTV, and PMPA to the sites of viral persistence in blood and lymphoid tissues.

Example 4

This example describes additional studies to expand the characterization of multiple drug-lipid nanoparticle formulations and their long term stability.

As described in Example 3, we developed multi-drug anti-HIV lipid nanoparticles containing the hydrophobic protease inhibitors lopinavir (LPV) and ritonavir (RTV) (marketed together as Kaletra®), and hydrophilic TFV (active drug in Viread®). With greater than 90% association of LPV and RTV, and approximately 12% association of TFV, these lipid-stabilized drug particles enhanced and prolonged plasma and intracellular drug exposure of all three drugs compared to free drug in primates. This LNP method design and the resulting in vivo pharmacokinetic data indicate that this new method is scalable and clinically relevant for production of multi-drug therapeutics for the treatment of HIV, cancer, and other diseases.

The described lipid-stabilized drug-combination nanoparticle compositions and the related production method are broadly applicable and capable of simultaneously incorporating both hydrophobic and hydrophilic drug at levels not achievable with traditional liposomes. To further demonstrate the applicability of the described methods and resulting nanoparticle formulations, we evaluated this method with additional different drug combinations. Each combination tested high and reproducible association of both hydrophobic drugs as well as stable association of an acceptable and reproducible fraction of hydrophilic drug (Table 11).

TABLE 11

Drug combinations that have been simultaneously associated into lipid-drug nanoparticles and produced on a large scale (15-60 mL volume).[a] Lipid-drug association efficiency[b] (mean ± standard deviation) is displayed in parentheses.

| | Hydrophobic Drugs (% particle-bound) | | Hydrophilic Drug (% particle-bound) |
|---|---|---|---|
| Combination 1 | Lopinavir (86.4 ± 0.9) | Ritonavir (83.4 ± 1.4) | Tenofovir (9.9 ± 2.9) |
| Combination 2 | Atazanavir (91.9 ± 6.8) | Ritonavir (88.5 ± 3.1) | Tenofovir (7.9 ± 1.8) |
| Combination 3 | Efavirenz (78.7) | Lopinavir (76.6) | Tenofovir (7.9) |
| Mean Association | 84.3 ± 5.3 | | 8.6 ± 0.9 |

[a]All compositions were formulated with DSPC:DSPE-mPEG2000 at an optimized molar ratio of 9:1. Lipid:drug molar ratios were as follows: Combination 1 lipid:LPV:RTV:TFV 115:10:5:15, Combination 2 lipid:ATZ:RTV:TFV 115:10:5:15, Combination 3 lipid:LPV:EFV:TFV 200:26.6:20:40.
[b]Lipid-drug association efficiency was determined by dialysis of the drug-lipid particle product against at least 1000x volume of iso-osmolar bicarbonate-buffered saline at physiologic pH for 4 hours at room temperature. Drug concentration after dialysis (determined by LC-MS/MS method) was compared to drug concentration before dialysis to determine percent of drug stably associated with lipid.

To test the long-term stability, the multi-drug nanoparticles were stored under refrigeration at 4° C. and were tested for stability after a prolonged period. The lipid-drug combination particles are stable as determined by both particle size and degree of drug association (Table 12). This is a critical factor when evaluating the clinical potential of pharmaceutical products, which must demonstrate an acceptable shelf life in order to be clinically viable. Even the hydrophilic compound, which readily diffuses out of most lipid particles in a number of hours, loses a remarkably low fraction of the associated drug after 8, 12, and 17 months in storage. This exceptional stability provides a substantial advantage for translation to clinical application.

TABLE 12

Storage stability of the fractions of drug bound to drug combination nanoparticle admixture[a]

| Drug/Time | Fraction of drug bound in multi-drug nanoparticles (% total) | | | |
|---|---|---|---|---|
|  | 0 months | 8 months | 12 months | 17 months |
| Liponavir (LPV) | 82.70 ± 7.00 | 95.33 ± 7.53 | 94.62 ± 11.86 | 92.89 |
| Ritonavir (RTV) | 88.30 ± 7.38 | 93.01 ± 7.70 | 94.91 ± 13.66 | 90.50 |
| Tenofovir (PMPA/TFV) | 9.32 ± 3.79 | 7.72 ± 2.95 | 8.79 ± 0.92 | 7.30 |

[a]Storage stability of LPV/RTV/PMPA 3-4 preparations were stored at 4° C. under aseptic conditions at 150 mg/mL lipid containing lopinavir/ritonavir/PMPA in multi-drug lipid nanoparticles admixture. The fraction of drug bound to multi-drug nanoparticles are determined after removal of free drugs from the preparation by dialysis method at indicated storage time points (0-17 months). Data expressed were mean and SD. At 17 months, only one batch of the preparation was available for stability analysis.
C = centigrade,
LPV = lopinavir,
mg = milligram,
mL = milliliter,
PMPA/TNF = tenofovir,
RTV = ritonavir,
SD = standard deviation.

As described above, we established the pH-dependent association of various drugs to lipids at neutral pH and the consequent release of the drugs when pH is lowered. Also described above, this stable integration and pH-dependent release of drugs from the multiple drug lipid nanoparticles was consistent for both lipophilic and water soluble compounds. To confirm the pH dependent release of the individual drugs from the multiple drug combination lipid nanoparticles, LPV/RTV/PMPA(TFV) lipid nanoparticles, assembled as described above, were subjected to different pH environments, and the free drug component of the supernatant was assayed to determine the amount of release. Consistent with the results reported in the Examples above, the different drugs exhibited a pH dependent release from the multiple drug combination lipid nanoparticles. See Table 13. This confirmed pH-responsive attribute demonstrated in Table 13 illustrates an added benefit to the disclosed multiple drug combination lipid nanoparticles. When a lipid nanoparticle is localized in tissues and taken up by HIV-infected cells, the incorporated antiretroviral drugs are then released inside the cell organelles (such as endosome and lysosomes) when the pH is lowered. With chemical stability of the proposed drugs in acidic conditions (where most drugs are extracted to measure plasma drug levels for LC-MS analysis), this attribute can enhance antiviral potency by providing a more stable, prolonged, and effective mode of drug delivery.

TABLE 13 pH dependent drug release from nanoparticles comprising lipid nanoparticles associated with lopinavir (LPV), ritonavir (RTV), and tenofovir (PMPA/TFV). The fraction of drug release at 37° C. over 2 hrs is expressed as mean ± SD %.

| pH | % Drug released from anti-HIV nanoparticles | | |
|---|---|---|---|
|  | Lopinavir (LPV) | Ritonavir (RTV) | Tenofovir (PMPA/TFV)) |
| 7.4 | 1 ± 0.6 | 2 ± 1 | 0 ± 2 |
| 6.5 | 3.9 ± 2.7 | 3.2 ± 4.9 | 15.9 ± 5.4 |
| 5.5 | 28.9 ± 1.4 | 29.0 ± 11.6 | 11.2 ± 1.5 |
| 4.0 | 93.7 ± 1.2 | 94.9 ± 0.7 | 28.7 ± 0.9 |

The enhancement of antiviral potency of the HIV drug combinations as presented in the disclosed multiple drug-lipid nanoparticle composition, specifically incorporating a combination of LPV, RTV, and PMPA(TFV) was assessed. The efficacy of the multiple drug-lipid nanoparticle composition was evaluated in HIV-infected CEM-174 cells and compared to soluble free drugs combined in equivalent ratios or used individually. At a 1:1:0.5 (m/m/m) drug ratio, respectively, LPV, RTV, and PMPA in the multiple drug-lipid nanoparticle formulation enhanced the individual drug potency as well as the equivalent fixed combination in soluble form (Table 14). Control lipid particles exhibited no antiviral effects. The multiple drug-lipid nanoparticle-formulated drugs exhibited about a 30-fold enhancement in the in vitro 50% inhibitory measure ($EC_{50}$). The exact enhancement will vary depending on the strain of virus, but this data experience indicates a 3- to 30-fold enhancement in antiviral potency attributed to multiple drug-lipid nanoparticle formulation.

TABLE 14

Effects of multiple drug lipid nanoparticle formulation containing lopinavir, ritonavir, and PMPA in HIV-2(287) replication (data expressed as 50% inhibitory drug concentration (nM) against viral replication). For combination treatments, the ratio of lopinavir, ritonavir and PMPA in the formulation was fixed at 1:1:0.5 (m/m/m).

| Treatment | $EC_{50}$ (nM) | | |
|---|---|---|---|
|  | Lopinavir (LPV) | Ritonavir (RTV) | Tenofovir (PMPA/TFV) |
| Drug combinations |  |  |  |
| Soluble 3 drug combination | 98 ± 0.3 | 98 ± 0.3 | 49 ± 0.2 |
| Drug-lipid nanoparticles with 3 drug combination | 3 ± 0.8 | 3.0 ± 0.8 | 1.5 ± 0.1 |
| Single agent controls |  |  |  |
| Lopinavir (LPV) | 102 |  |  |
| Ritonavir (RTV) |  | 1044 |  |
| Tenofovir (PMPA/TFV) |  |  | 100-6000 |

All three of the lipid-drug combinations of Table 11 have been evaluated in vivo and initial pharmacokinetic data from a subset of these combinations is described in Examples 1-3 above. Lipid-drug particle mixtures produced using the disclosed large-scale production method consistently demonstrate sustained plasma drug levels for over 7 days, enhanced plasma drug exposure, and higher intracellular drug concentrations in lymph nodes and blood compared to the same combinations in free form. Total plasma drug exposure after administration of lipid-stabilized drug, evaluated as area under the plasma time course curve (AUC), is generally significantly higher than that achieved by free drug and consistently shifted toward later drug exposure (Table 15). This is most remarkable for TFV, with only 8-10% stable lipid association, which consistently demonstrates a 10- to 20-fold increase in plasma exposure as well as a dramatic shift in AUC toward later time points. Primates treated with free drug exhibited ~90% of total TFV exposure within the first 8 hours, whereas those treated with lipid-stabilized drug particles exhibited ~95% of total TFV exposure after 8 hours, regardless of drug combination (Table 15). Lipid-drug particles also enhance and prolong intracellular drug exposure in peripheral blood mononuclear cells (PBMCs), providing detectable intracellular drug levels for over 7 days whereas free drug levels fall near or below detection limits by 24 hours (Table 16). Bloodwork and physical examination have revealed no significant adverse effects associated with subcutaneous administration of lipid-drug combination particles, indicating an acceptable degree of safety.

disclosure focuses on anti-HIV drugs and related therapies, it will be apparent that the disclosed approach can be applied for the production and administration of therapeutic agents

TABLE 15

The effect of lipid stabilization on plasma drug exposure. Three different optimized multi-drug lipid formulations were studied to determine the change in area under the plasma curve (AUC) compared to the same drugs in free form.[a] Drugs used include lopinavir (LPV), ritonavir (RTV), tenofovir (TFV), atazanavir (ATZ), and efavirenz (EFV).

| | AUC (µg · hr · mL−1) | | | $AUC_{fraction}$ (% of total)[b] | | | |
|---|---|---|---|---|---|---|---|
| | Free Drug | Lipid Drug | Lipid/Free | Free Drug | | Lipid Drug | |
| rug | 0-168 h | 0-168 h | Ratio[c] | 0-8 h | 8-168 h | 0-8 h | 8-168 h |
| LPV | 3.8 ± 4.0 | 63.6 ± 12.5 | 16.7 | 19.7 ± 2.2 | 80.3 ± 2.2 | 13.0 ± 1.4 | 87.0 ± 1.4 |
| RTV | 1.4 ± 1.2 | 7.5 ± 3.4 | 5.4 | 36.1 ± 7.6 | 63.9 ± 7.6 | 19.1 ± 4.9 | 80.9 ± 4.9 |
| TFV | 56.6 ± 17.0 | 738.8 ± 31.0 | 13.1 | 92.2 ± 2.6 | 7.8 ± 2.6 | 5.3 ± 0.7 | 94.7 ± 0.7 |
| ATZ | 1.9 ± 0.8 | 0.4 ± 0.1 | 0.2 | 58.7 ± 22.6 | 41.3 ± 22.6 | 11.3 ± 7.2 | 88.6 ± 7.2 |
| RTV | 5.0 ± 1.5 | 2.4 ± 0.7 | 0.5 | 33.9 ± 8.6 | 66.1 ± 8.6 | 22.3 ± 4.7 | 77.7 ± 4.7 |
| TFV | 26.3 ± 3.9 | 662.0 ± 249.0 | 25.2 | 91.7 ± 1.4 | 8.3 ± 1.4 | 4.4 ± 1.8 | 95.6 ± 1.8 |
| LPV | n/a | 21.4 ± 0.1 | n/a | n/a | n/a | 24.6 ± 4.2 | 75.4 ± 4.2 |
| EFV | n/a | 31.2 ± 2.7 | n/a | n/a | n/a | 18.1 ± 0.2 | 81.9 ± 0.2 |
| TFV | n/a | 1612.0 ± 13.2 | n/a | n/a | n/a | 3.8 ± 0.6 | 96.2 ± 0.6 |

[a]Primates were administered lipid-drug particles and free drug (except in the case of LPV/EFV/PMPA) in a cross-over study. Plasma concentration was determined by LC-MS/MS method, and AUC was calculated using the trapezoidal rule. Data expressed as mean ± standard deviation (n = 2 or 4 per group).
[b]Fractional AUC was calculated by dividing the AUC for the indicated time frame by the total AUC.
[c]Lipid/Free Ratio is the mean total AUC produced by lipid-drug mixture divided by mean total AUC produced by free drug.

TABLE 16

The effect of lipid association on intracellular levels of lopinavir, ritonavir, and tenofovir in peripheral blood mononuclear cells (PBMCs) after subcutaneous drug administration.[a]

| | Drug Concentration (ng/106 mononuclear cells) | | | | | | | | |
|---|---|---|---|---|---|---|---|---|---|
| | Lopinavir | | | Ritonavir | | | Tenofovir | | |
| Time (h) | Free Drug | Lipid-Drug Particles | Lipid/Free Ratio[b] | Free Drug | Lipid-Drug Particles | Lipid/Free Ratio[b] | Free Drug | Lipid-Drug Particles | Lipid/Free Ratio[b] |
| 0 | 0.00 ± 0.00 | 0.00 ± 0.00 | 1 | 0.00 ± 0.00 | 0.00 ± 0.00 | 1 | 0.00 ± 0.00 | 0.00 ± 0.00 | 1 |
| 0.5 | 0.67 ± 0.31 | 0.28 ± 0.24 | 0.4 | 0.96 ± 1.67 | 0.41 ± 0.58 | 0.4 | 5.01 ± 5.12 | 1.29 ± 1.83 | 0.3 |
| 1 | 1.93 ± 1.18 | 1.85 ± 1.11 | 1 | 2.92 ± 2.62 | 2.57 ± 1.04 | 0.9 | 3.55 ± 4.21 | 1.29 ± 0.93 | 0.4 |
| 5 | 0.32 ± 0.28 | 2.59 ± 1.44 | 8.1 | 0.90 ± 0.60 | 2.20 ± 1.43 | 2.4 | 0.27 ± 0.21 | 1.24 ± 1.16 | 4.6 |
| 24 | 0.16 ± 0.28 | 3.26 ± 2.25 | 20.4 | 0.00 ± 0.00 | 4.09 ± 2.90 | >409.0 | 0.01 ± 0.01 | 0.70 ± 0.14 | 70 |
| 168 | 0.00 ± 0.00 | 0.08 ± 0.10 | >8.0 | 0.00 ± 0.00 | 1.32 ± 1.14 | >132.0 | 0.00 ± 0.00 | 0.25 ± 0.25 | >25.0 |

[a]Four primates (M. nemestrina) were administered lopinavir (LPV), ritonavir (RTV), and tenofovir (TFV) subcutaneously in combination in lipid-drug particle form and free drug form in a cross-over study at a normalized dose of 25 mg/kg LPV, 14.3 mg/kg RTV, and 17.1 mg/kg TFV. PBMCs were isolated from whole blood by density gradient method, and cell pellets of 2 million PBMCs each were analyzed. Data expressed as mean ± standard deviation.
[b]Lipid/Free Ratio is the mean drug concentration after administration of lipid-drug particle mixture, divided by the mean drug concentration after administration of free drug. In cases where the drug level was below detectable limits, the number was taken as "0.01" to calculate ratio.

These results provide a further demonstration that the association of multiple drugs with lipid excipients in nanoparticle aggregations substantially enhances the performance of delivery and sustained release/availability of the drugs. Specifically, the association of drug combinations with lipid excipients in the disclosed nanoparticles results in significantly enhanced plasma and intracellular drug concentrations for prolonged periods of time. This permits a much more effective treatment for diseases, such as HIV, where administration of multiple drugs attacking distinct targets is necessary for clearance of the virus. This approach provides an exciting opportunity to overcome drawbacks of prior strategies where multiple drugs might be administered separately, which failed to provide high levels of all administered drugs in the same target tissues and cells and, thus, failed to lead to full clearance of viruses. While the present disclosure focuses on anti-HIV drugs and related therapies, it will be apparent that the disclosed approach can be applied for the production and administration of therapeutic agents for other diseases and/or infections that involve small molecule agents that can similarly associate with particle-forming lipid excipients.

Example 5

Examples 1-4 above describe multiple drug lipid nanoparticles assembled in a process that permits the co-incorporation of both hydrophilic and hydrophobic drug agents into stable lipid nanoparticles using a mixed dual solvent approach. As described, the drug agents are separately dissolved in either an organic solvent or aqueous solvent, after which the solvents are combined in a proportion that permits mixing without formation of multiple phases (referred to herein as "mixed dual solvent" approach). This allows for stable formulations that provide significantly enhanced and prolonged delivery of multiple drugs, each with different physical characteristics, e.g., varying hydrophilicity/hydrophobicity, and potentially addressing distinct disease targets. Having a single formulation that can flexibly address multiple disease targets makes the formulation useful to address diseases, such as HIV/AIDS, while avoiding potential resistance to single target therapies. To this specific goal, exemplary anti-HIV drugs that are approved by the FDA, and their respective targets/mode of action, are provided in Table 17.

This example describes the successful assembly of multiple drug lipid nanoparticles that incorporate selected anti-HIV drugs using an illustrative alternative assembly methodology. This alternative assembly methodology was designed to ensure or enhance the complete dissolution and mixture of the hydrophilic and hydrophobic components (i.e., small molecule agents and excipient components) together in a final, homogenous composition. This alternative methodology involved fully solubilizing all ingredients, namely the hydrophobic small molecule agents, the hydrophilic small molecule agents, and the excipient components, in a single miscible solvent. This was followed by controlled removal of solvent to form a dry product, which was rehydrated to form the multi-drug lipid nanoparticles. In certain aspects, this illustrative alternative methodology resulted in multiple drug lipid nanoparticles with enhanced or optimized characteristics, including a higher degree of stability and hydrophilic drug association.

TABLE 17

The list of FDA approved HIV drugs and their viral target protein

| HIV target protein | FDA approved drug | MW g/mol |
|---|---|---|
| Reverse transcriptase | Efavirenz[a] | 315.68 |
|  | Rilpivirine[a] | 402.88 |
|  | Emtricitabine (FTC)[b] | 247.2 |
|  | Lamivudine (3TC)[b] | 229.26 |
|  | Tenofovir (TFV)[b] | 287.2 |
| Protease | Lopinavir | 628.8 |
|  | Ritonavir | 720.95 |
|  | Atazanavir | 704.9 |
|  | Darunavir | 547.7 |
|  | Indinavir | 613.79 |

TABLE 17-continued

The list of FDA approved HIV drugs and their viral target protein

| HIV target protein | FDA approved drug | MW g/mol |
|---|---|---|
| Integrase | Raltegravir | 402.88 |
|  | Dolutegravir | 419.38 |

[a]Non-nucleoside reverse transcriptase inhibitor (NNRTI)
[b]Nucleoside analogue derivatives that inhibit HIV reverse transcriptase (NRTI)

As described above, some organic solvents such as alcohols (e.g., methanol, ethanol, propanol, hexanol, and the like) can be mixed with a small fraction of water to form a water-saturated single-phase miscible solvent without the creation of an emulsion. This can even be combined with other organic solvents such as chloroform ($CHCl_3$) that, individually, would be water immiscible while maintaining the single phase so long as the entire mixture does not contain water beyond its saturation capacity of the water-miscible organic solvent. Here, a single phase, fully miscible solvent capable of solvating all ingredients, namely the hydrophilic and hydrophobic drug agents and excipient components, was created to permit full dissolution and mixing of the drug agents and excipients for maximum interaction. In some embodiments, the organic component of the miscible solvent can be a combination of different organic molecules and aqueous solution or buffer. For example, chloroform can be mixed with an alcohol. In the present examples, chloroform was mixed with ethanol at a ratio of 65:35 (vol/vol). In some embodiments, the ethanol can be replaced by methanol, propanol, hexanol, and the like. The presence of some water insoluble organic component, such as chloroform, was believed to assist in the drying of the mixture.

The selected lipophilic (hydrophobic/water insoluble) small molecule agent(s), hydrophilic (water soluble/lipid insoluble) small molecule agent(s), lipid excipient, and excipient containing a large hydrophilic domain are solubilized fully in the miscible solvent. For purposes of this illustrative example, the lipophilic small molecule agents (also referred to as "Class 1") were selected from Table 18 and hydrophilic small molecule agents (also referred to as "Class 2") were selected from Table 19, each of which provides structure and physical characteristics regarding each illustrative small molecule agent.

TABLE 18

Illustrative lipophilic (hydrophobic; also referred to as "Class 1") small molecule agents for HIV treatment suitable for incorporation in the disclosed lipid nanoparticles.

| Name | Structure | LogP | H donor | Acceptor | Formal Net Charge* | Water solubility @ 25° C. | MW |
|---|---|---|---|---|---|---|---|
| Efavirenz | [structure] | 4 | 1 | 5 | 0 | 0.000093 mg/L | 315.67 |

TABLE 18-continued

Illustrative lipophilic (hydrophobic; also referred to as "Class 1") small molecule agents for HIV treatment suitable for incorporation in the disclosed lipid nanoparticles.

| Name | Structure | LogP | H donor | Acceptor | Formal Net Charge* | Water solubility @ 25° C. | MW |
|---|---|---|---|---|---|---|---|
| Lopinavir | 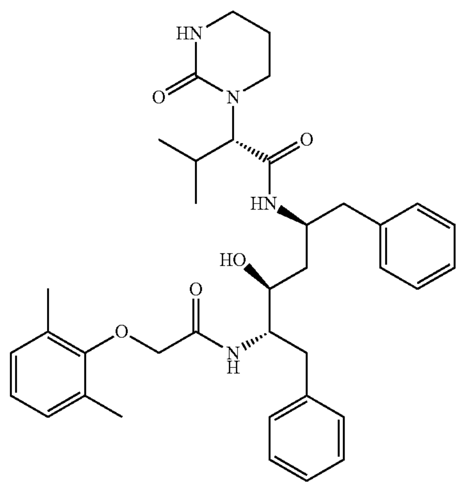 [SMILES: Cc1cccc(C)c1OCC(=O)N[C@@H](Cc1ccccc1)[C@@H](O)C[C@H](Cc1ccccc1)NC(=O)[C@H](C(C)C)N1CCCNC1=O] | 5.9 | 4 | 5 | 0 | 0.0000077 g/L | 628.80 |
| Ritonavir | 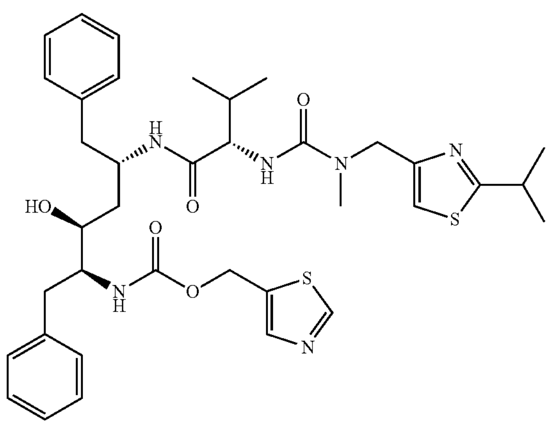 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1] | 6 | 5 | 9 | 0 | <0.0001 g/L | 720.94 |
| Indinavir | 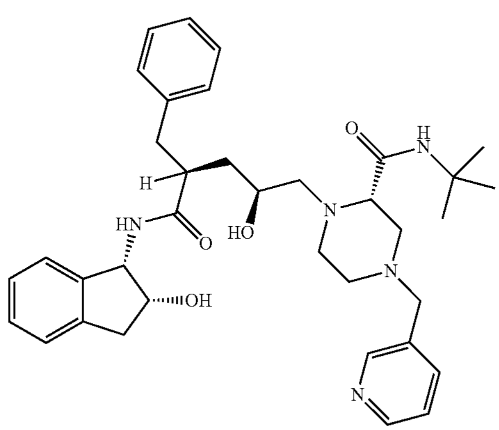 [SMILES: CC(C)(C)NC(=O)[C@@H]1CN(Cc2cccnc2)CCN1C[C@@H](O)C[C@@H](Cc1ccccc1)C(=O)N[C@H]1c2ccccc2C[C@H]1O] | 2.3 | 4 | 7 | 0 | 0.015 g/L | 613.80 |

TABLE 18-continued

Illustrative lipophilic (hydrophobic; also referred to as "Class 1") small molecule agents for HIV treatment suitable for incorporation in the disclosed lipid nanoparticles.

| Name | Structure | LogP | H donor | Acceptor | Formal Net Charge* | Water solubility @ 25° C. | MW |
|---|---|---|---|---|---|---|---|
| Atazanavir | 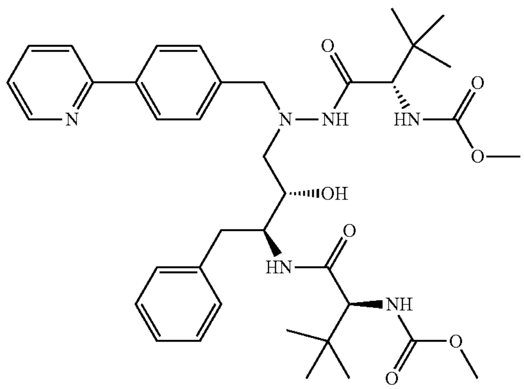 [SMILES: COC(=O)N[C@H](C(=O)N[C@@H](Cc1ccccc1)[C@@H](O)CN(Cc1ccc(-c2ccccn2)cc1)NC(=O)[C@@H](NC(=O)OC)C(C)(C)C)C(C)(C)C] | 5.6 | 5 | 9 | 0 | 0.00011 g/L | 704.86 |
| Rilpivirine | 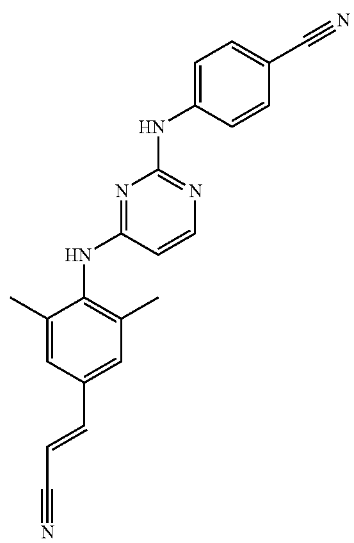 [SMILES: Cc1cc(/C=C/C#N)cc(C)c1Nc1ccnc(Nc2ccc(C#N)cc2)n1] | 4.5 | 2 | 6 | 0 | 0.000094 g/L | 366.41 |
| Dolutegravir | 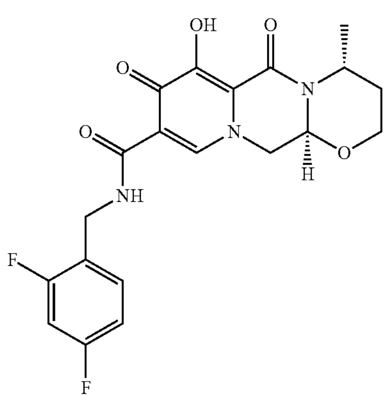 [SMILES: C[C@@H]1CCO[C@H]2Cn3cc(C(=O)NCc4ccc(F)cc4F)c(=O)c(O)c3C(=O)N12] | 2.4 | 2 | 8 | 0 | .095 g/L | 419.38 |

*Net formal charge at neutral pH

TABLE 19

Illustrative hydrophilic (also referred to as "Class 2") small molecule agents for HIV treatment suitable for incorporation in the disclosed lipid nanoparticles.

| Name | Structure | LogP | H donor | Acceptor | Formal Net Charge* | Water solubility @ 25° C. | MW |
|---|---|---|---|---|---|---|---|
| Tenofovir | 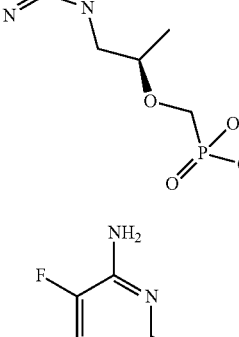 | −1.6 | 3 | 8 | Negative charge (2) | 13.3 g/L | 287.21 |
| Emtricitabine | 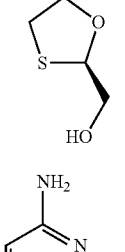 | −2.4 | 2 | 5 | Positive charge (1) | 112 g/L | 247.25 |
| Lamivudine | 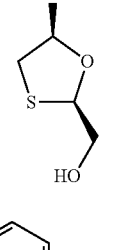 | −1.4 | 2 | 4 | Positive charge (1) | 70 g/L | 229.26 |
| Raltegravir | 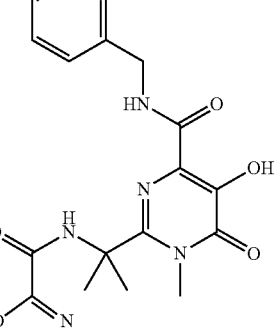 | −0.39 | 3 | 9 | 0 | 0.1 g/L* | 444.41 |

*Net formal charge at neutral pH

This example describes further studies that characterize multiple drug lipid nanoparticles that were assembled in the single, miscible solvent method described above. The illustrative multiple drug lipid nanoparticles incorporated lopinavir (LPN), ritonavir (RTV), and tenofovir (TFV) and were subjected to in vivo pharmacokinetic studies in primates establishing an extended presence in plasma. Additionally, to investigate the surprisingly high and sustained levels of hydrophilic drug, tenofovir upon administration of the lipid nanoparticles, a sucrose gradient test was performed, establishing a high level of drug association in the nanoparticles, even in the context of the sheer force applied in the gradient test.

Multiple drug lipid nanoparticles incorporated lopinavir (LPN), ritonavir (RTV), and tenofovir (TFV) were assembled according to the following general approach:

1. Select one or two drugs hydrophobic and water insoluble (Class 1) drugs in Table 18 (for example, lopinavir and ritonavir).
2. Select one or two drugs hydrophilic and water soluble (Class 2) drugs listed in Table 19 (for example, tenofovir and/or emtricitabine and/or lamivudine).
3. Select the excipient combination (for example, 9 parts DSPC and 1 part PEG-DSPE).
4. Prepare a single-phase miscible solvent that enables full solubilization of the chosen water-insoluble Class 1 drugs and water soluble Class 2 drugs plus the excipients from step 3. Examples include $CHCl_3$:Methanol:Water (65:35:4); $CHCl_3$:Ethanol:Water (65:35:4); $CHCl_3$:Propanol:Water (65:35:4); and $CHCl_3$:Hexanol:Water (65:35:4).
5. The components in Steps 1, 2 and 3 are solubilized with the miscible solvent in step 4.
6. The drugs (steps 1 and 2) as well as excipients (step 3) and the miscible solvent (step 4) are dried under reduced pressure with assistance of a combination of heat, reduced pressure and/or aerosolization to provide for uniformity and efficiency of drying.
7. The dehydrated composition is heated above gel-to-liquid phase transition temperature of the excipient mixture (e.g., 50° C.).
8. A buffered saline solution is prepared and the temperature is equilibrated to the same temperature as dehydrated composition.
9. The buffered saline solution and dehydrated composition are gradually combined and maintained at the defined (e.g., 50° C.) for 3 hr.
10. The resulting hydrated multi-drug lipid nanoparticles are size-reduced by sheering or forcing through small orifice or pressurized filter apparatus while maintaining at the defined temperature (in liquid phase of lipidic excipients). Typically, about 10-15 passes provide a defined size of 60-120 nm in diameter.

The drug to excipient molar ratios is typically high and can be achieved up to 1 drug molecule (i.e., the drugs in steps 1 and 2, above) in the combination for every 3 molecule of excipient (i.e., described in step 3). The final product mixture contain over 70-90% of drugs—from those listed in Table 18 (lipid soluble; Class 1) and Table 19 (water soluble; Class 2), that are associated with the multi-drug lipid nanoparticles. Thus, the low fraction of free drugs is permissible for therapeutic application as a loading dose to saturate the non-specific distribution and adsorption into tissues.

With the use of miscible solvent and rehydration control procedure, which is referred to as single, miscible solvent method, additional fraction of Class 2 water soluble agents are associated with the resulting lipid nanoparticle. The improvement of Class 2 agent association can be noted in Table 21 below. These data reflecting association of the hydrophobic (Class 1) and hydrophilic (Class 2) drug agents are provided below in Tables 20 and 21. These tables also provide comparative data for the multi-drug lipid nanoparticles produced from the dual solvent method as well as with traditional liposome drug formulation.

TABLE 20

Percent association of hydrophobic HIV drugs in formed lipid nanoparticles.

| | | | % Drug Association to Particles | | |
|---|---|---|---|---|---|
| FDA approved HIV drug | MW | Hydro- phobicity (Log P) | LNPs from single, miscible solvent method | LNPs from mixture of dual solvent method | Liposomes[a] |
| Efavirenz[b] | 315.67 | 4 | 80-90 | 76 | 80 |
| Rilpivirine[b] | 366.41 | 4.5 | 90-100 | 75-76 | 14 |
| Atazanavir[c] | 704.9 | 5.6 | 90-100 | 90-100 | |
| Darunavir[c] | 547.7 | 1.8 | | 97 | |
| Lopinavir[c] | 628.8 | 5.9 | 90-100 | 80-100 | |
| Ritonavir[c] | 720.95 | 6 | 90-100 | 80-100 | |

[a]Reported values
[b]Non-nucleoside reverse transcriptase inhibitor (NNRTI) targeting the reverse transcriptase
[c]HIV target: Protease

TABLE 21

Percent association of hydrophilic HIV drugs in formed lipid nanoparticles.

| | | | % Drug Association to Particles | | |
|---|---|---|---|---|---|
| FDA approved HIV drug | MW | Hydro- phobicity (Log P) | LNPs from single, miscible solvent method | LNPs from mixture of dual solvent method | Liposomes[a] |
| Emtricitabine[b] | 247.2 | −1.4 | 78-80 | 3-10 | 1-2 |
| Lamivudine[b] | 229.26 | −1.4 | 85 | 10-30 | 4-5 |
| Tenofovir[b] | 287.2 | −1.6 | 78-85 | 7-30 | 5 |
| Raltegravir[c] | 444.41 | −0.39 | 75-89 | 9-25 | 1-2 |

Figure 10:
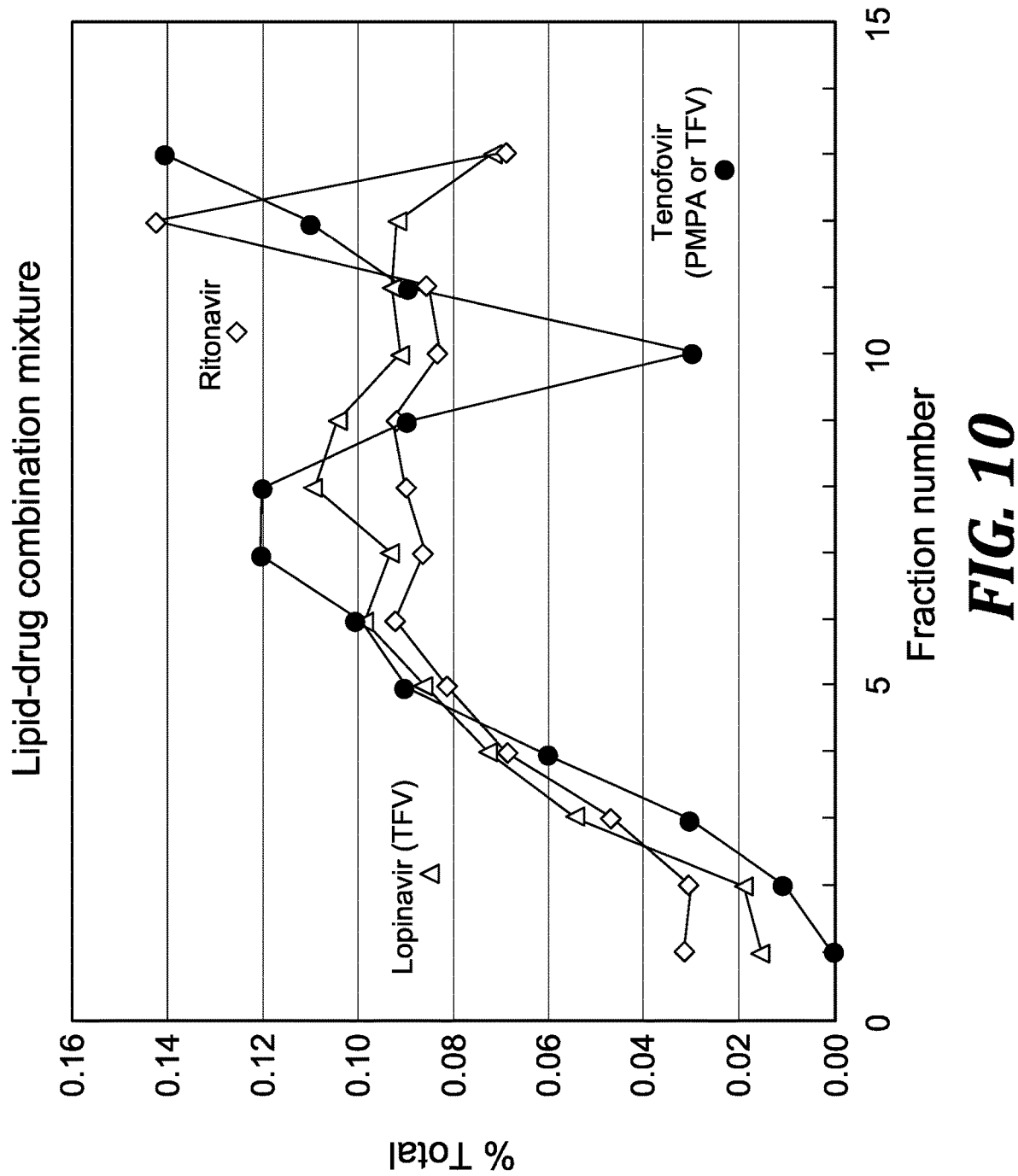
FIG. 10 graphically illustrates the separation of three drugs, lopinavir (LPV), ritonavir (RTV), and tenofovir (TFV or PMPA), formulated in lipid-drug particle. The lipid-drug combination mixtures were subjected to 5-20% sucrose gradient centrifugation to separate bound from free fraction of the three drugs. Fractions 2-10 were used as bound fractions while fractions 11-14 (top with low sucrose density) were used as the free fraction. The results indicated the following % association to lipid-drug particles: Lopinavir (LPV)=81.8%; Ritonavir (RTV)=76%; Tenofovir (TFV or PMPA)=75.5%.

[a]Reported values
[b]Nucleoside reverse transcriptase inhibitor (NRTI) targeting the reverse transcriptase
[c]HIV target: Integrase To evaluate the degree of stable Class 2 drug association in reported Table 21, we subjected LNPs composed of Lopinavir (LPV), ritonavir (RTV), and Tenofovir (TFV) to sucrose gradient test. The sucrose gradient test centrifugation test separates any unbound drugs from multi-drug lipid nanoparticles by sedimentation of lipid-drug particles through a sucrose gradient with increasing density to strip off unbound drugs. Under these conditions, all the free drugs in solution remained at (or floated to) the top of gradient where the sucrose density is low. Specifically, using a continuous gradient of 5-20% (with 65% cushion) sucrose, the lipid-drug particle mixture was subjected to centrifugal force at 200,000 g for 4 hr. Through this process, we were able to separate bound and unbound drug fractions. As shown in FIG. 10, most of the water-soluble drug, TFV, was found to co-sediment with lipophilic LPV and RTV (i.e., with the stable lipid nanoparticles). The data indicate that these particles are stable under the sheer force as it traversed through the sucrose gradient. We estimated the bound fraction of hydrophilic drug TFV found in particles to be around 75.5%, far exceeding 7-30% TFV association with LNPs prepared by mixed-solvent or even lower number achieved with liposomes (~5%) (Table 21). The data indicate that multi drug lipid nanoparticles are very stable under the sheer force as it traversed through the sucrose gradient and that the associated drugs, including the hydrophilic drugs, maintain a strong association with the nanoparticles. It is noted that the observed percentage of multi drug lipid nanoparticle association for the other two drugs (LPV and RTV) are consistent with data in Table 11.

Considering the data in FIG. 10 and Table 21, there is clear distinction between drug loading and drug association between lipid-drug particles and liposomes. Drug loading is a measure of the fraction of lipids to stabilize the drug which by itself is unable to remain in solution and suspension. Drug association is a measure of fraction of the total drug in the mixture found to be absorbed or associated with the particles. In both of these assessment, liposomes provide much lower capacity of drug loading and fraction of hydrophilic drug associated in the final lipid-drug particle formulations.

Multi-drug lipid nanoparticles prepared under this single, miscible solvent method are thus distinctly more stable and provide higher degree of hydrophilic drug association. Without being bound to any particular theory, this effect is likely due to the removal of bound water on the amphipathic lipid corona of the nanoparticles. This allows the hydrophilic drug to become trapped within this unstirred layer at the surface of lipid nanoparticle structure, which is mainly formed by the hydrophobic drug and excipient components. Such trapping is unlikely to occur post-formation of the lipid nanoparticles. As a result, both hydrophilic drugs and hydrophobic drugs remain with a high degree of association to the stable lipid nanoparticle.

These results demonstrate that both assembly methods produce lipid nanoparticles with a high degree of association of hydrophobic drug agents. However, the single, miscible solvent method described in this example resulted in a much higher association rate of hydrophilic drugs. Ultimately, lipid nanoparticles assembled with the single, miscible solvent method exhibited lipid to total drug mole ratios of about 3:1, with a high percentage of the initial solubilized drugs (hydrophobic or hydrophilic) associating with the formed lipid nanoparticles. The lipid nanoparticles assembled with the mixed dual solvent method, described above, exhibited a lipid to total drug mole ratio ranging from about 3:1 to about 8:1, indicating a tendency to retain less overall drug, which is most likely attributable to the lower degree of hydrophilic drug association as compared to the lipid nanoparticles developed in the single, miscible solvent approach.

In any event, the lipid nanoparticles assembled with either the single, miscible solvent method or the mixed dual solvent method exhibited a much higher association of especially hydrophilic drug agents as compared to liposomes, which can only encapsulate a limited amount of the water soluble drug that is initially combined with the component lipids. In this regard, liposomes typically only have a lipid to total drug ratio of more than 10:1, indicating that the ultimate liposome particle is predominantly lipid, which is necessary to form a stable bilayer structure, with limited encapsulation. Liposomes are simply not capable of forming at the low lipid to drug ratios (high drug to lipid ratios) obtained with the disclosed lipid nanoparticles because of the sheer number of lipid molecules required to form a large, stable bilayer membrane. Furthermore, as explained in more detail below, liposomes are particularly poor at stably retaining significant levels of hydrophilic (Class 2) drug molecules. Thus, there is clear distinction between drug loading and drug association between lipid-drug particles and liposomes. "Drug loading" is a measure of fraction of lipids to stabilize the drug particles, which are unable to remain alone in solution and suspension. "Drug association" is a measure of fraction of the total drug in the mixture found to be absorbed or associated with the particles. In both of these assessment, liposomes provide much lower capacity of drug loading and fraction of hydrophilic drug associated in the final lipid-drug particle formulations. Ultimately, the combination of different types (e.g., hydrophilic and hydrophobic) drug agents in the same liposome formulation has not been accomplished and cannot provide the advantages apparent in the disclosed lipid nanoparticles.

Figure 9A:
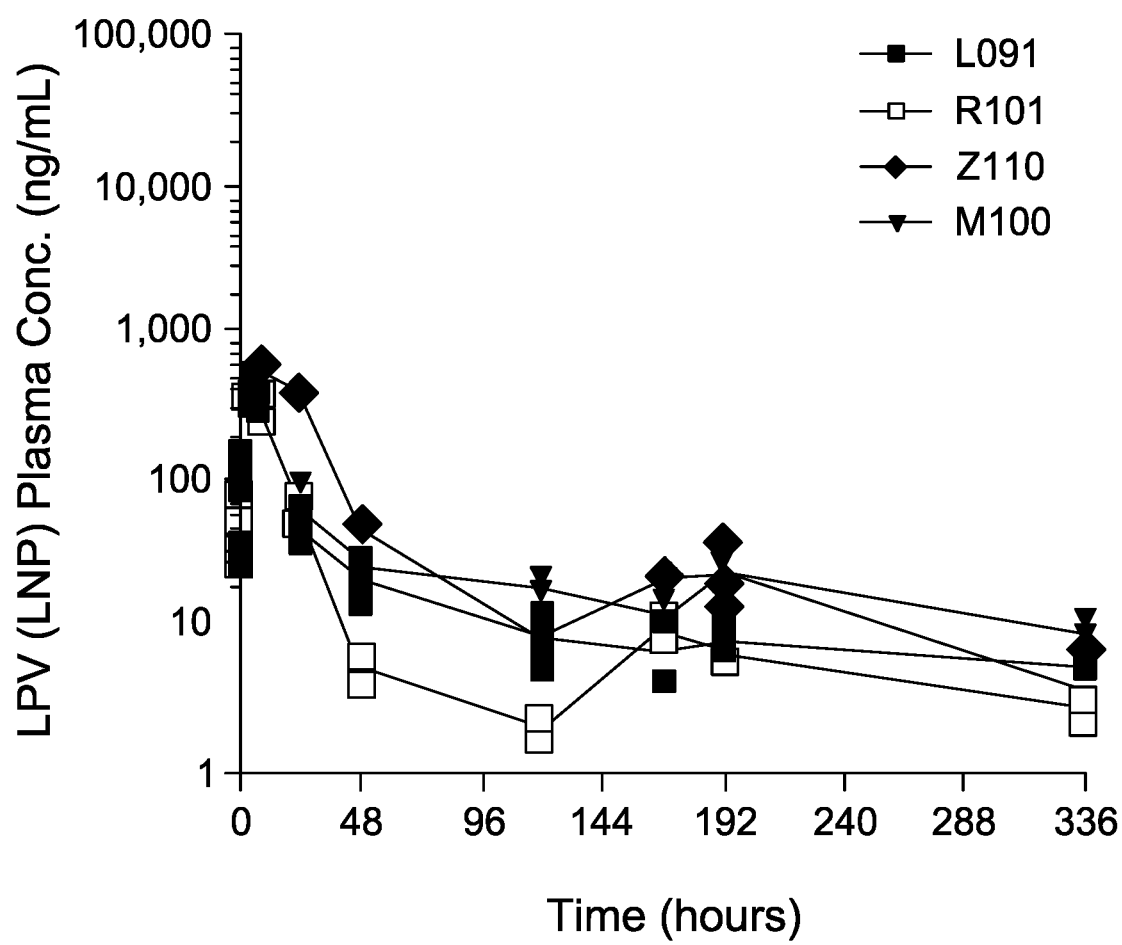
FIGS. 9A-9C graphically illustrate the time-course of individual drug concentrations in four primate macaques (*M. nemestrina*) after administration of multiple drug lipid nanoparticles containing lopinavir (FIG. 9A), ritonavir (FIG. 9B), and tenofovir (FIG. 9C) (2:1:3 mole ratio). Further analysis indicates that over 90% of drugs in the plasma could be attributed to lipid-drug particle associated form. In contrast, as demonstrated previously, after administration of unformulated free drug, each drug falls below detectable levels in the plasma by 24 hrs.
Figure 9B:
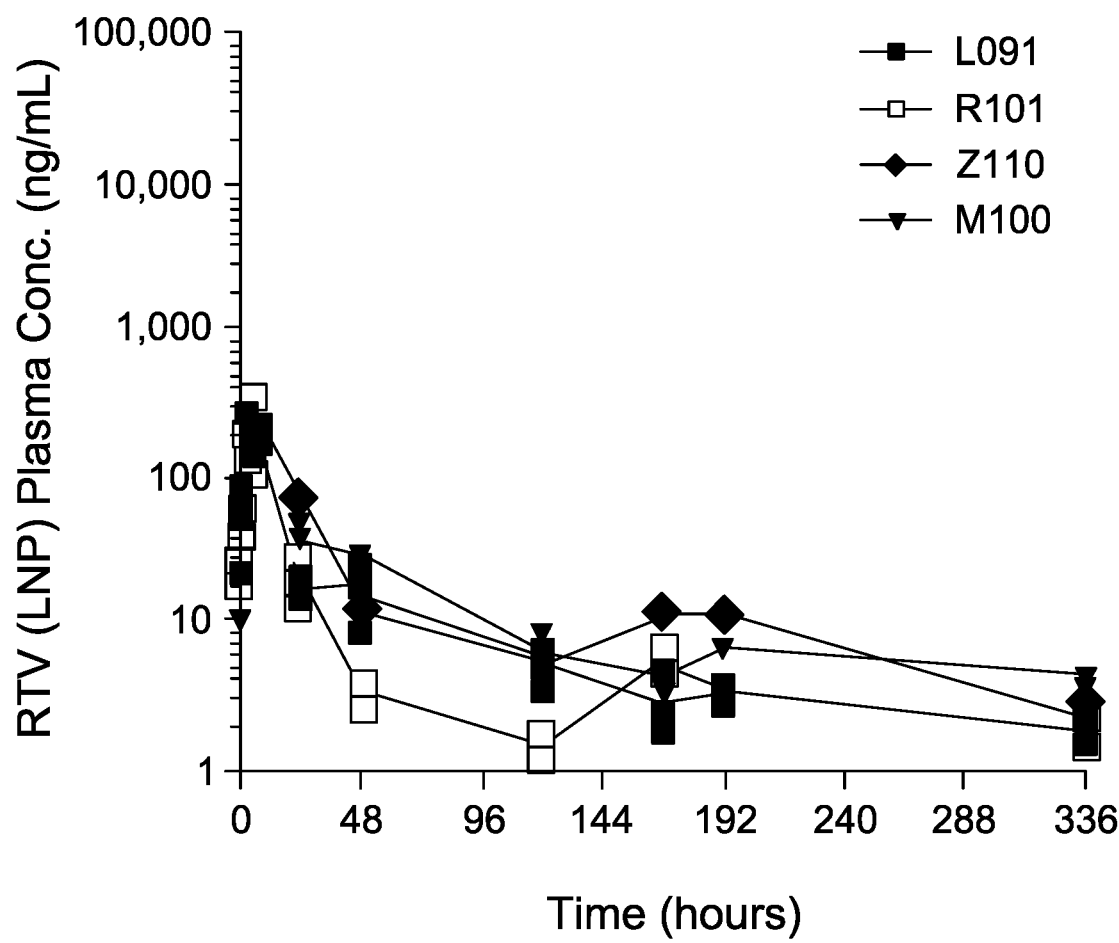
Figure 9C:
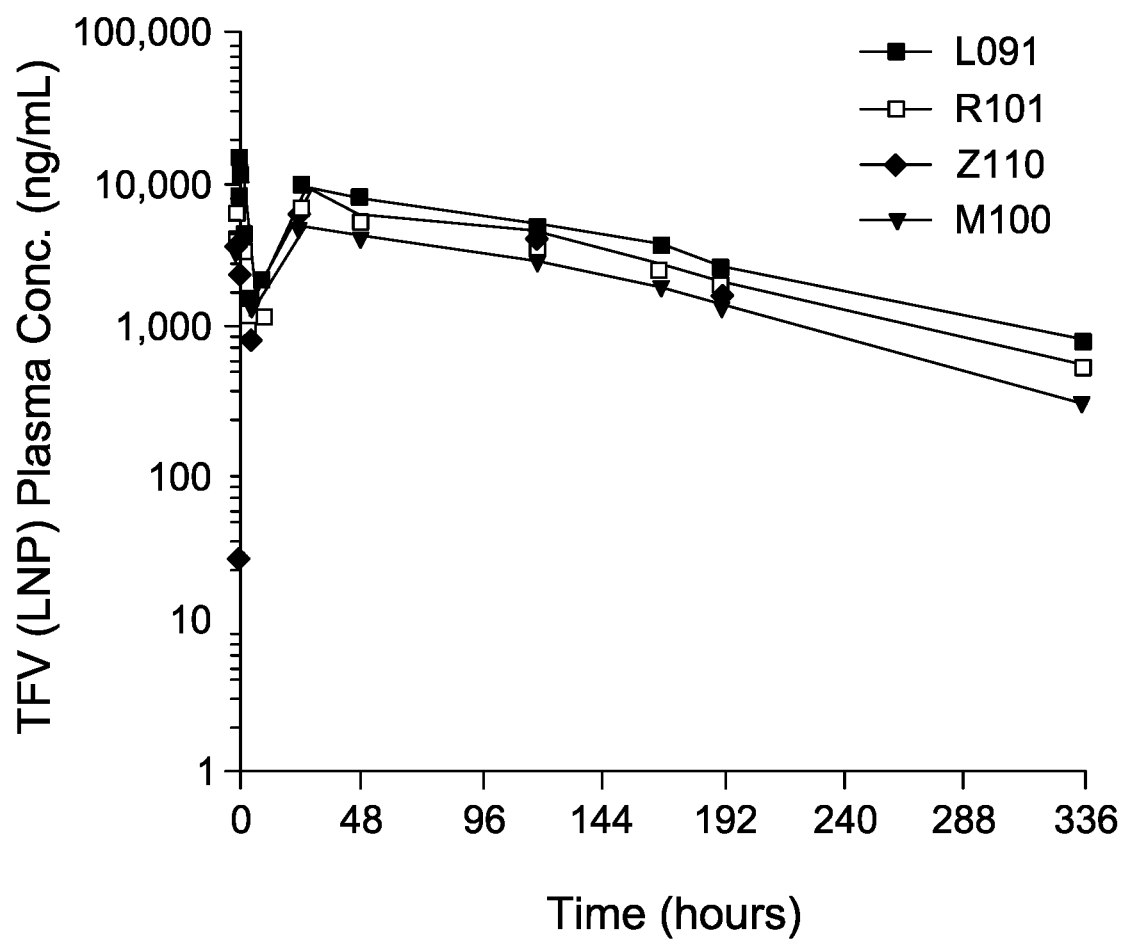

These multiple drug lipid nanoparticles were also characterized for physical characteristics, stability, and pharmacokinetic parameters in primates (*M. nemestrina*) accordingly to methodologies described in more detail in the above examples. Briefly, four primate macaques (*M. nemestrina*) were administered subcutaneously with 25 mg/kg of the multi-drug nanoparticles that were constructed with lopinavir, ritonavir and tenofovir at a 2:1:3 mole ratio using the single, miscible solvent method. The concentration of each individual drug was monitored over time. As demonstrated previously, for all three drugs the free (unformulated) drug in solution falls below detectable levels within 24 hrs. However, as illustrated in FIGS. 9A and 9B, we found that both hydrophobic drugs such as lopinavir and ritonavir provided sustained and prolonged plasma time course as expected. In fact, the duration of sustained plasma drug levels from nanoparticles assembled in the single, miscible solvent technique was further extended to at least two weeks instead of one week, as observed in the original studies of the mixed dual solvent LNPs described above in Examples 1-4. Moreover, as shown in FIG. 9C, we found that hydrophilic tenofovir (TFV) unexpectedly exhibited over 90% of sustained plasma drug concentrations for two weeks. This is surprising considering that previous equilibrium dialysis assays on the multi-drug lipid nanoparticles (produced from the mixed dual solvent method described above in Examples 1-4) indicated about a 9-10% bound fraction.

To illustrate the enhanced performance and stability in vivo, the primate study results for these lipid nanoparticles (produced from the single, miscible solvent method) were compared against the similar multiple drug lipid nanoparticles assembled in the combined dual solvent method and miscible solve method described in the above examples. See Table 22. It is notable that the single, miscible solvent method resulted in additional presence of the drugs in the plasma, from 1 week to 2 weeks sustained plasma drug levels, reflecting a plasma half-life extension for all three drugs, TFV, LPV and RTV. Particularly noticeable drug exposure and time extension difference in pharmacokinetic for two methodologies are parallel with increased fraction of TFV associated with LNPs.

TABLE 22

Comparison of physical characteristics and primate pharmacokinetic profile for an anti-HIV (3) drug combination, lopinavir (LPV), ritonavir (RTV) and tenofovir (TFV), as produced using single, miscible solvent or dual solvent methods.

| | (LPV/RTV/TFV) LNPs from single, miscible solvent method | (LPV/RTV/TFV) LNPs from mixture of dual solvent method |
|---|---|---|
| Physical Characteristics | | |
| Lipophilic LPV/RTV association | Similar (90-100%) | Similar (80-100%) |
| Hydrophobic TFV association | 78-85% | 7-30% |
| Stability | More stable | Less stable |
| Pharmacokinetic parameters in primates (*M. nemestrina*) | | |
| Sustained plasma 3 drug levels | 2 weeks | 1 week |
| Apparent terminal half-life of drug | | |
| LPV | 100-138 h | 22-78 h |
| RTV | 74-120 h | 35-72 h |
| TFV | 70-80 h | 6-45 h |
| Drug exposure per dose | | |
| LPV (25 mg/kg dose) | 44,000-76,000 (µg · h/L) | 18,000-69,600 (µg · h/L) |
| RTV (13 mg/kg dose) | 20,000-26,514 (µg · h/L) | 6,000-19,400 (µg · h/L) |
| TFV (15 mg/kg dose) | 722,000-1,312,689 (µg · h/L) | 9,000-485,159 (µg · h/L) |

The multiple drug-lipid nanoparticles prepared according to the single, miscible solvent method are distinctly more stable and provide higher degree of hydrophilic drug association, even when incorporating additional distinct (hydrophobic) drug agents. Without being bound to any particular theory, this is believed to be the result of the removal of bound water from the hydrophilic corona region around the formed lipid nanoparticles. The hydrophilic corona is established by the substantial hydrophilic domains provided by some of the nanoparticle excipients, which are positioned on the exterior surface. During the assembly of the lipid nanoparticles, these hydrophilic domains provide a refuge for the water soluble drugs present in the solution at that time. The hydrophilic drugs are believed to become trapped in high quantities within this corona region at the surface of lipid-drug particles, whereas the structure of the nanoparticle is mainly provided by hydrophobic drug and lipid excipient. As a result, both hydrophilic drug and hydrophobic drug remained associated with high degree to the multiple drug loaded to drug-combination nanoparticle stabilized by lipids. Typical nanoparticle assembly methodologies cannot achieve this result because similar corona regions, while hydrophilic, are typically "unstirred", indicating that due to structural constraints, very little infiltration of preformed corona regions occurs from the outside environment, even by small hydrophilic molecules. Thus, once assembled, lipid nanoparticles harboring hydrophobic small molecule agents cannot have hydrophobic agents further loaded into a corona region.

To illustrate the structural distinction between the disclosed multiple drug nanoparticles and typical liposomal formulations, FIGS. 8A-8C schematically depict the structures of the multiple drug nanoparticles assembled by both the single, miscible solvent (FIG. 8A) and the mixed dual solvent (FIG. 8B) approaches, and liposomes (FIG. 8C). In the illustrated formulations, the nanoparticles and liposomes are constructed with phosphatidylcholine (PC) lipid as the lipid excipient and pegylated (PEG)-lipid and the excipient with a significant hydrophilic domain. The particles are not represented to scale and the liposome is not depicted with the lamellar bilayer, but this is understood as part of the structure thereof. The excipients containing polyethyleneglycol (PEG-lipid) on particle surface retain the hydrophilic drugs within the unstirred corona and simultaneously repel additional agents (hydrophilic or otherwise) from entering after assembly. The ability to retain the hydrophilic drugs in the corona regions require that the hydrophilic and hydrophobic drugs are mixed with lipids and dehydrated, prior to nanoparticle assembly during rehydration, as described herein. The use of mixed dual solvents, as described in Examples 1-4, results in the assembly of nanoparticles that retain significant amount of the hydrophilic drug agents, which is a significant enhancement over liposomes, which do not similarly retain hydrophilic agents. Instead, liposomes can encapsulate a small amount of hydrophilic molecules within the center. However, this typically does not provide stable retention of significant amounts. Furthermore, liposomes have known stability issues when administered in vivo. The lipid nanoparticles generated from the single, miscible solvent method have a higher degree of association of hydrophilic agents within the unstirred corona, resulting in drug retention rates approaching that observed for hydrophobic agents. Furthermore, these particles appear to be conferred with enhanced stability, as illustrated by sucrose gradients (see Example 6 below), where the nanoparticles are able to retain up to ~85% of the hydrophilic agents under the sheer force of sucrose gradient centrifugation. The lipid nanoparticles assembled in the mixed dual solvent method, retain about 7-20% of the hydrophilic drug in similar conditions, and liposomes retain only about around 3-5% association. Ultimately, both types of lipid nanoparticles significantly outperform standard liposomes for integration and retained association of hydrophilic drug agents to due to liposomes' comparatively limited ability to encapsulate hydrophilic drug and the repulsion of the unstirred corona.

Collectively, these data indicate at least that (1) the lipid-drug particle formulation are capable of not only high degree of drug loading but also high levels of stable drug association to particle; (2) the high levels of association removes the requirement that unincorporated drugs need to be removed from the formulation prior to administration, thus simplifying the manufacturing process; (3) the unique formulation provides ability to co-formulate drugs with extreme physical characteristics, i.e., lipophilic and hydrophilic molecules, so that both can be reliably and effectively delivered together to the target site; (4) the flexible and physically stable lipid-drug association provide long-acting behavior, which is important for medical use; and (5) the platform with highly loaded drug in lipid-drug mixture is novel and clearly advantageous over any liposome of lipid vesicle formulation or micellar preparation reported in the literature.

While illustrative embodiments have been illustrated and described, it will be appreciated that various changes can be made therein without departing from the spirit and scope of the invention.

The invention claimed is:

1. A multi-drug nanoparticle, comprising:
   a first small molecule agent with a log P at 25° C. greater than 1;
   a second small molecule agent with a log P at 25° C. less than 0;
   a first amphiphilic excipient, wherein the first amphiphilic excipient is a lipid comprising a hydrophilic domain with a molecular weight less than 300 grams/mol; and
   a second amphiphilic excipient comprising a hydrophilic domain with a molecular weight greater than 500 grams/mol.

2. The multi-drug nanoparticle of claim 1, wherein the nanoparticle has a mole ratio of small molecule agents to lipid excipients of at least 1:10.

3. The multi-drug nanoparticle of claim 1, wherein the first small molecule agent is selected from the group consisting of rilpivirine (RPV) or a prodrug thereof, efavirenz (EFV) or a prodrug thereof, dolutegravir (DTG) or a prodrug thereof, indinavir (IDV) or a prodrug thereof, atazanavir (ATV) or a prodrug thereof, ritonavir (RTV) or a prodrug thereof, and lopinavir (LPV) or a prodrug thereof.

4. The multi-drug nanoparticle of claim 1, wherein the second small molecule agent is selected from the group consisting of tenofovir (TFV) or a prodrug thereof, emtricitabine (FTC) or a prodrug thereof, lamivudine (3TC) or a prodrug thereof, raltegravir (RAL) or a prodrug thereof, and zidovudine or a prodrug thereof.

5. The multi-drug nanoparticle of claim 1, where the nanoparticle has a mole ratio of first small molecule agent to second small molecule agent between about 1:20 to about 20:1.

6. The multi-drug nanoparticle of claim 1, wherein the first amphiphilic excipient is selected from the group consisting of phospholipids, sphingolipids, cholesterol and steroid derivatives, bile acids and derivatives, cardilipin, acylglycerides and derivatives, glycolipids, acyl-peptides, and fatty acids.

7. The multi-drug nanoparticle of claim 6, wherein the phospholipid is selected from the group consisting of distearoyl phosphatidylcholine (DSPC); dipalmitoyl phosphatidylcholine; dimysristoyl phosphatidylcholine; dioleoyl phosphatidylcholine; trans-esterified phospholipid derived from eggs, soybean, and flaxseed; phosphatidylethanolamine; phosphatidylglycerol; phosphatidylserine; and phosphatidic acid.

8. The multi-drug nanoparticle of claim 1, wherein the first amphiphilic excipient is a phospholipid comprising a fatty acid tail with at least 14 carbons.

9. The multi-drug nanoparticle of claim 1, wherein the first amphiphilic excipient is a phospholipid comprising two fatty acid tails, wherein each fatty acid tail has one or no carbon to carbon double bonds.

10. The multi-drug nanoparticle of claim 1, wherein the second amphiphilic excipient is a glycoprotein, a glycolipid, a polyalkylene oxide-containing polymer, or a polyalkylene oxide-containing lipid.

11. The multi-drug nanoparticle of claim 10, wherein the polyalkylene oxide-containing lipid is selected from the group consisting of polyoxyethylene-containing lipids and polyoxypropylene-containing lipids.

12. The multi-drug nanoparticle of claim 11, wherein the polyoxyethylene-containing lipid is a phospholipid functionalized with polyethylene glycol, wherein the polyethylene glycol has a number average molecular weight from about 500 to about 20,000 g/mol.

13. The multi-drug nanoparticle of claim 12, wherein the phospholipid functionalized with polyethylene glycol is N-(carbonyl-methoxypolyethyleneglycol-2000)-1,2-distearoyl-sn-glycero-3-phosphoethanolamine (mPEG-2000-DSPE).

14. The multi-drug nanoparticle of claim 10, wherein the polyalkylene oxide-containing lipid is a phospholipid comprising a fatty acid tail with at least 14 carbons.

15. The multi-drug nanoparticle of claim 1, wherein the nanoparticle has a mole ratio of the first amphiphilic excipient to the second amphiphilic excipient of about 2:1 to about 20:1.

16. The multi-drug nanoparticle of claim 1, wherein the nanoparticle has a diameter of about 20 nm to about 200 nm.

17. The multi-drug nanoparticle of claim 1, wherein the nanoparticle comprises a hydrophilic corona with a thickness of about 2 nm to about 15 nm when in isotonic buffer at physiological pH and 25° C.

18. The multi-drug nanoparticle of claim 1, wherein the nanoparticle does not have a lipid-bilayer membrane structure.

19. A pharmaceutical composition comprising:
   a plurality of multi-drug nanoparticles as recited in claim 1.

20. A method of preparing a multi-drug nanoparticle, comprising:
   dissolving in an organic solvent a first small molecule agent with a log P at 25° C. greater than 1, a first amphiphilic excipient wherein the first amphiphilic excipient is a lipid comprising a hydrophilic domain with a molecular weight less than 300 grams/mol, and second amphiphilic excipient comprising a hydrophilic domain with a molecular weight greater than 500 grams/mol, to provide an organic solvent solution, wherein the organic solvent comprises a subcomponent that is miscible with water;
   dissolving in an aqueous solvent a second small molecule agent with a log P at 25° C. less than 0 to provide an aqueous solvent solution;
   mixing the organic solvent solution and the aqueous solvent solution to provide a mixed solvent solution;
   removing the mixed solvents from the mixed solvent solution to provide a solid multi-drug product comprising the first small molecule agent, the first amphiphilic excipient, the second amphiphilic excipient, and the second small molecule agent; and
   rehydrating the solid product in an aqueous solution to provide a solution with multi-drug nanoparticles.

21. A method of preparing a multi-drug nanoparticle, comprising:
   dissolving in a miscible solvent comprising an organic component and an aqueous component at a ratio of between about 20:1 and about 40:1 (v/v):

a first small molecule agent with a log P at 25° C. greater than 1, a second small molecule agent with a log P at 25° C. less than 0, a first amphiphilic excipient wherein the first amphiphilic excipient is a lipid comprising a hydrophilic domain with a molecular weight less than 300 grams/mol, and a second amphiphilic excipient comprising a hydrophilic domain with a molecular weight greater than 500 grams/mol, removing the miscible solvent to provide a solid multi-drug product comprising the first small molecule agent, the second small molecule agent, the first amphiphilic excipient, and the second amphiphilic excipient;

heating the solid multi-drug product to a first temperature that is at least 3° C. above a gel-to-liquid phase transition temperature of the amphiphilic excipients; and rehydrating the solid multi-drug product in an aqueous solution to provide a solution with multi-drug nanoparticles.

* * * * *

UNITED STATES PATENT AND TRADEMARK OFFICE
CERTIFICATE OF CORRECTION

PATENT NO. : 10,799,456 B2  
APPLICATION NO. : 15/735118  
DATED : October 13, 2020  
INVENTOR(S) : R. Ho et al.

Page 1 of 1

It is certified that error appears in the above-identified patent and that said Letters Patent is hereby corrected as shown below:

On the Title Page

| Column | Line | |
|---|---|---|
| 2, Item (57), Abstract | 4 | change "same, The" to -- same. The -- |

In the Claims

| Column | Line | |
|---|---|---|
| 67 | 43 | change "where the" to -- wherein the -- |

Signed and Sealed this  
Eighth Day of March, 2022

Drew Hirshfeld  
*Performing the Functions and Duties of the  
Under Secretary of Commerce for Intellectual Property and  
Director of the United States Patent and Trademark Office*